(12) United States Patent
Kleinstiver et al.

(10) Patent No.: US 12,264,341 B2
(45) Date of Patent: Apr. 1, 2025

(54) CRISPR-Cas ENZYMES WITH ENHANCED ON-TARGET ACTIVITY

(71) Applicant: The General Hospital Corporation, Boston, MA (US)

(72) Inventors: Benjamin Kleinstiver, Medford, MA (US); Russell T. Walton, Waban, MA (US)

(73) Assignee: The General Hospital Corporation, Boston, MA (US)

( * ) Notice: Subject to any disclaimer, the term of this patent is extended or adjusted under 35 U.S.C. 154(b) by 482 days.

(21) Appl. No.: 17/157,805

(22) Filed: Jan. 25, 2021

(65) Prior Publication Data

US 2021/0261932 A1 Aug. 26, 2021

Related U.S. Application Data

(60) Provisional application No. 62/965,671, filed on Jan. 24, 2020.

(51) Int. Cl.
| | | |
|---|---|---|
| *C12N 9/22* | (2006.01) | |
| *C12N 9/10* | (2006.01) | |
| *C12N 9/78* | (2006.01) | |
| *C12N 15/90* | (2006.01) | |

(52) U.S. Cl.
CPC ............ *C12N 9/22* (2013.01); *C12N 9/1007* (2013.01); *C12N 9/78* (2013.01); *C12N 15/907* (2013.01); *C07K 2319/71* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 8,697,359 B1 | 4/2014 | Zhang |
| 9,322,037 B2 | 4/2016 | Liu et al. |
| 9,512,446 B1 | 12/2016 | Joung et al. |
| 9,752,132 B2 | 9/2017 | Joung et al. |
| 9,926,546 B2 | 3/2018 | Joung et al. |
| 10,093,910 B2 | 10/2018 | Joung et al. |
| 10,266,850 B2 | 4/2019 | Doudna et al. |
| 10,526,591 B2 | 1/2020 | Joung et al. |
| 10,633,642 B2 | 4/2020 | Joung et al. |
| 2010/0076057 A1 | 3/2010 | Sontheimer et al. |
| 2011/0189776 A1 | 8/2011 | Terns et al. |
| 2011/0223638 A1 | 9/2011 | Wiedenheft et al. |
| 2013/0130248 A1 | 5/2013 | Haurwitz et al. |
| 2014/0068797 A1 | 3/2014 | Doudna et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0201857 A1 | 7/2014 | Fahrenkrug et al. |
| 2014/0212869 A1 | 7/2014 | Sampas et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0271987 A1 | 9/2014 | Manoury et al. |
| 2014/0273226 A1 | 9/2014 | Wu |
| 2014/0273230 A1 | 9/2014 | Chen et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0294773 A1 | 10/2014 | Brouns et al. |
| 2014/0295556 A1 | 10/2014 | Joung et al. |
| 2014/0298547 A1 | 10/2014 | Sastry-Dent et al. |
| 2014/0304853 A1 | 10/2014 | Ainley et al. |
| 2014/0309487 A1 | 10/2014 | Lee et al. |
| 2014/0310828 A1 | 10/2014 | Lee et al. |
| 2014/0310830 A1 | 10/2014 | Zhang et al. |
| 2014/0315985 A1 | 10/2014 | May et al. |
| 2014/0335063 A1 | 11/2014 | Cannon et al. |
| 2014/0335620 A1 | 11/2014 | Zhang et al. |
| 2014/0349400 A1 | 11/2014 | Jakimo et al. |
| 2014/0357530 A1 | 12/2014 | Zhang et al. |
| 2014/0377868 A1 | 12/2014 | Joung et al. |

(Continued)

FOREIGN PATENT DOCUMENTS

| | | |
|---|---|---|
| CA | 3069296 | 1/2019 |
| CN | 104854241 | 8/2015 |

(Continued)

OTHER PUBLICATIONS

Kleinstiver et al., "Supplementary Materials: Engineered CRISPR-Cas9 nucleases with altered PAM specificities," Nature, Jul. 2015, 523(7561):481-497, 289 pages.
International Preliminary Report on Patentability in International Appln. No. PCT/US2021/014933, mailed on Aug. 4, 2022, 8 pages.
U.S. Appl. No. 61/652,086, filed May 25, 2012, Jinek et al.
Abudayyeh et al., "A Cytosine Deaminase for Programmable Single-base RNA Editing," Science, Jul. 26, 2019, 365(6451):382-386.
Al-Attar et al, "Clustered Regularly Interspaced Short Palindromic Repeats (CRISPRs): The Hallmark of an Ingenious Antiviral Defense Mechanism in Prokaryotes," Biol Chem. 2011, 392(4):277-289.
Anders et al., "4un3: Crystal structure of Cas9 bound to PAM-containing DNA target," RCSB Protein Data Bank, May 25, 2014, retrieved on May 6, 2016, retrieved from URL <http://www.rcsb.org/pdb/explore/explore.do?structureId=4U>, 3 pages.
Anders et al., "Structural basis of PAM-dependent target DNA recognition by the Cas9 endonuclease," Nature, 2014, 513:569-573.

(Continued)

*Primary Examiner* — Celine X Qian
*Assistant Examiner* — Tiffany Nicole Grooms
(74) *Attorney, Agent, or Firm* — Fish & Richardson P.C.

(57) ABSTRACT

Engineered versions of *Streptococcus pyogenes* Cas9 (SpCas9) and SpCas9 variants that have improved on-target editing capabilities, and methods of use thereof.

35 Claims, 30 Drawing Sheets

Specification includes a Sequence Listing.

(56) References Cited

U.S. PATENT DOCUMENTS

| | | |
|---|---|---|
| 2015/0024500 A1 | 1/2015 | Yu et al. |
| 2015/0031134 A1 | 1/2015 | Zhang et al. |
| 2015/0045546 A1 | 2/2015 | Siksnys et al. |
| 2015/0050699 A1 | 2/2015 | Siksnys et al. |
| 2015/0071899 A1 | 3/2015 | Liu et al. |
| 2016/0208243 A1 | 7/2016 | Zhang et al. |
| 2016/0312199 A1* | 10/2016 | Joung .................... C12N 15/111 |
| 2017/0058271 A1 | 3/2017 | Joung et al. |
| 2017/0081650 A1 | 3/2017 | Joung et al. |
| 2017/0233756 A1 | 8/2017 | Begemann et al. |
| 2018/0100148 A1 | 4/2018 | Vakulskas et al. |
| 2018/0216088 A1 | 8/2018 | Joung et al. |
| 2018/0282714 A1 | 10/2018 | Joung et al. |
| 2018/0320201 A1* | 11/2018 | Vakulskas .............. C12N 15/88 |
| 2019/0071657 A1 | 3/2019 | Joung et al. |
| 2019/0106687 A1 | 4/2019 | Joung |
| 2019/0177710 A1 | 6/2019 | Lee |
| 2019/0382775 A1 | 12/2019 | Tan et al. |
| 2020/0140835 A1 | 5/2020 | Joung et al. |
| 2020/0149024 A1 | 5/2020 | Joung et al. |
| 2020/0277586 A1* | 9/2020 | Nureki ...................... C12N 9/22 |
| 2021/0284978 A1 | 9/2021 | Kleinstiver et al. |
| 2021/0355465 A1 | 11/2021 | Joung et al. |
| 2021/0380955 A1* | 12/2021 | Bryson ...................... A61P 3/00 |

FOREIGN PATENT DOCUMENTS

| | | | |
|---|---|---|---|
| CN | 105543195 | 5/2016 | |
| CN | 106062197 | 10/2016 | |
| WO | WO 2008/108989 | 9/2008 | |
| WO | WO 2010/054108 | 5/2010 | |
| WO | WO 2012/164565 | 12/2012 | |
| WO | WO 2013/098244 | 7/2013 | |
| WO | WO 2013/176772 | 11/2013 | |
| WO | WO-2013176772 A1 * | 11/2013 | ........... C12N 15/102 |
| WO | WO 2014/124284 | 8/2014 | |
| WO | WO 2014/144288 | 9/2014 | |
| WO | WO 2014/144592 | 9/2014 | |
| WO | WO 2014/152432 | 9/2014 | |
| WO | WO-2014152432 A2 * | 9/2014 | ........... C12N 9/0071 |
| WO | WO 2014/191521 | 12/2014 | |
| WO | WO 2014/204724 | 12/2014 | |
| WO | WO 2014/204725 | 12/2014 | |
| WO | WO 2015/089364 | 6/2015 | |
| WO | WO 2015/089473 | 6/2015 | |
| WO | WO 2015/089486 | 6/2015 | |
| WO | WO 2015/200378 | 12/2015 | |
| WO | WO 2016/115179 | 7/2016 | |
| WO | WO 2016/115355 | 7/2016 | |
| WO | WO 2016/141224 | 9/2016 | |
| WO | WO 2016/205613 | 12/2016 | |
| WO | WO 2017/015015 | 1/2017 | |
| WO | WO 2017/040348 | 3/2017 | |
| WO | WO 2017/070633 | 4/2017 | |
| WO | WO-2017070633 A2 * | 4/2017 | .............. A61P 31/18 |
| WO | WO 2017/081288 | 5/2017 | |
| WO | WO 2017/184768 | 10/2017 | |
| WO | WO 2018/119359 | 6/2018 | |
| WO | WO 2019/009682 | 1/2019 | |
| WO | WO 2019/040650 | 2/2019 | |
| WO | WO 2019/079347 | 4/2019 | |
| WO | WO 2019/092042 | 5/2019 | |
| WO | WO 2019/217941 | 11/2019 | |
| WO | WO 2019/217942 | 11/2019 | |
| WO | WO 2019/217943 | 11/2019 | |
| WO | WO 2019/217944 | 11/2019 | |
| WO | WO 2020/041751 | 2/2020 | |
| WO | WO 2021/042047 | 3/2021 | |

OTHER PUBLICATIONS

Anders et al., "Structural Plasticity of PAM Recognition by Engineered Variants of the RNA-Guided Endonuclease Cas9," Molecular Cell, Mar. 17, 2016, 61(6):895-902.

Balemans et al., "Increased bone density in sclerosteosis is due to the deficiency of a novel secreted protein (SOST)," Hum Mol Genet., 2001, 10(5):537-543.

Barrangou & May, "Unraveling the potential of CRISPR-Cas9 for gene therapy," Expert Opin. Biol. Ther., 2014, 15:311-314.

Bisaria et al., "Lessons from Enzyme Kinetics Reveal Specificity Principles for RNA-Guided Nucleases in RNA Interference and CRISPR-Based Genome Editing," Cell Syst., Jan. 2017, 4(1):21-29.

Canela et al., "DNA Breaks and End Resection Measured Genomewide by End Sequencing," Molecular Cell, 2016, 63: 1-14.

Canver et al., "BCL11A enhancer dissection by Cas9-mediated in situ saturating mutagenesis," Nature., 2015, 527(7577), 192-7.

Carroll, "A CRISPR Approach to Gene Targeting," Molecular Therapy, Sep. 2012, 20:(9)1658-1660.

Casini et al., "A highly specific SpCas9 variant is identified by in vivo screening in yeast," Nat. Biotechnol., 2018, 36(3):265-271.

Cencic et al., "Protospacer Adjacent Motif (PAM)-Distal Sequences Engage CRISPR Cas9 DNA Target Cleavage," Oct. 2014, PLOS One, 9(10):e109213, 13 pages.

Chen & Zhao, "A highly sensitive selection method for directed evolution of homing endonucleases," Nucleic Acids Res., 2005, 33(18):e154, 7 pages.

Chen et al., "Enhanced proofreading governs CRISPR-Cas9 targeting accuracy," Nature, Oct. 2017, 550(7676):407-410.

Choi & Meyerson, "Targeted genomic rearrangements using CRISPR/Cas technology," Nat Commun., Apr. 24, 2014, 5:3728, 9 pages.

Chu et al., "Rationally Designed Base Editors for Precise Editing of the Sickle Cell Disease Mutation," The CRISPR Journal, Apr. 20, 2021, 4(2):169-177.

Chylinski et al., "The tracrRNA and Cas9 families of type II CRISPR-Cas immunity systems," RNA Biol., May 2013, 10:726-737.

Clement et al., "CRISPResso2 provides accurate and rapid genome editing sequence analysis," Nature Biotechnology, Feb. 2019, 37:224-226.

Cong et al., "Multiplex genome engineering using CRISPR/Cas systems," Science, 2013, 339:819-823 (Author Manuscript).

Courtney et al., "CRISPR/Cas9 DNA cleavage at SNP-derived PAM enables both in vitro and in vivo KRT12 mutation-specific targeting," Gene Ther., 2016, 23(1):108-12.

Cox et al., "Congenital insensitivity to pain: novel SCN9A missense and in-frame deletion mutations," Hum Mutat., 2010, 31:E1670-86.

Crosetto et al, "Nucleotide-resolution DNA double-strand break mapping by next-generation sequencing," Apr. 2013, Nat Methods 10(4): 361-365.

Dagdas et al., "A Conformational Checkpoint Between DNA Binding and Cleavage by CRISPR-Cas9," Science Advances, Aug. 2017, 3(8): eaao0027.

Deltcheva et al., "CRISPR RNA maturation by trans-encoded small RNA and host factor RNase III," Nature, 2011, 471(7340):602-607 (Author Manuscript).

Deveau et al., "Phage response to CRISPR-encoded resistance in Streptococcus thermophilus," J Bacteriol., 2008, 190(4):1390-400.

DiCarlo et al., "Genome engineering in Saccharomyces cerevisiae using CRISPR-Cas systems," Nucleic Acids Res, 2013, 1-8.

Ding et al., "Enhanced efficiency of human pluripotent stem cell genome editing through replacing TALENs with CRISPRs," Cell Stem Cell., Apr. 4, 2013, 12(4):393-4 (Author Manuscript).

Doench et al., "Optimized sgRNA design to maximize activity and minimize off-target effects of CRISPR-Cas9," Nature Biotechnology, Jan. 18, 2016, 34:184-191, 12 pages.

Dong et al., "The crystal structure of Cpf1 in complex with CRISPR RNA," Nature, 2016, 532(7600):522-526.

Doudna & Charpentier, "The new frontier of genome engineering with CRISPR-Cas9," Science, Nov. 2014, 346(6213):1258096, 10 pages.

Doyon et al., "Directed evolution and substrate specificity profile of homing endonuclease I-SceI," J. Am. Chem. Soc., 2006, 128:2477-2484.

Duan et al., "Genome-wide identification of CRISPR/Cas9 off-targets in human genome," Cell Res, 2014, 24(8):1009-1012.

Elliott et al., "Gene Conversion Tracts from Double-Strand Break Repair in Mammalian Cells," Mol Cell Biol., 1998, 18:93-101.

(56) References Cited

OTHER PUBLICATIONS

Esvelt et al., "Orthogonal Cas9 proteins for RNA-guided gene regulation and editing," Nat. Methods, 2013, 10:1116-1121.
Findlay et al., "Saturation editing of genomic regions by multiplex homology-directed repair," Nature, 2014, 513:120-3.
Flannick et al., "Loss-of-function mutations in SLC30A8 protect against type 2 diabetes," Nat Genet., 2014, 46:357-63.
Fonfara et al., "Phylogeny of Cas9 determines functional exchangeability of dual-RNA and Cas9 among orthologous type II CRISPR-Cas systems." Nucleic Acids Res., 2014, 42(4): 2577-2590.
Fu et al., "High-frequency off-target mutagenesis induced by CRISPR-Cas nucleases in human cells," Nat Biotechnol., 2013, 31:822-826 (Author Manuscript).
Fu et al., "Improving CRISPR-Cas nuclease specificity using truncated guide RNAs," Nat. Biotechnol, Mar. 2014, 32(3):279-284.
Gabriel et al., "An unbiased genome-wide analysis of zinc-finger nuclease specificity," Nat Biotechnol., 2011, 29:816-823.
Gagnon et al., "Efficient mutagenesis by Cas9 protein-mediated oligonucleotide insertion and large-scale assessment of single-guide RNAs," PLoS One, 2014, 9, e98186.
Gaj et al., "ZFN, TALEN and CRISPR/Cas-based methods for genome engineering," Trends Biotechnol,, Jul. 2013, 31(7):397-405.
Gao et al., "Engineered Cpf1 variants with altered PAM specificities," Nat Biotechnol., 2017, 35:789-792.
Gasiunas et al., "Cas9-crRNA ribonucleoprotein complex mediates specific DNA cleavage for adaptive immunity in bacteria," Proc Natl Acad Sci USA, 2012, 109(39):E2579-E2586.
Gaudelli et al., "Programmable base editing of A•T to G•C in genomic DNA without DNA cleavage," Nature, Nov. 23, 2017, 551:464-471.
Gehrke et al., "An APOBEC3A-Cas9 base editor with minimized bystander and off-target activities," Nature Biotechnology, Nov. 2018, 36(10):977-982, 8 pages.
GenBank Accession No. AKS40380.1, "Cas9 [Synthetic plasmid pFC330]," Aug. 2, 2015, 1 page.
GenBank Accession No. EOS46485.1, "The Genome Sequence of Lachnospiraceae bacterium COE1," May 29, 2013, 2 pages.
GenBank Accession No. NP_472073, "hypothetical protein lin2744 [listeria innocua Clip11262]," Dec. 17, 2014, 2 pages.
GenBank Accession No. WP_010922251.1, "type II CR.ISPR RNA-guided endonuclease Cas9 [*Streptococcus pyogenes*]," Oct. 7, 2015, 2 pages.
Grünewald et al., "CRISPR DNA Base Editors with Reduced RNA off-Target and Self-Editing Activities," Nature Biotechnology, Sep. 2, 2019, 37(9):1041-1048, 10 pages.
Grünewald et al., "Transcriptome-wide off-target RNA editing induced by CRISPR-guided DNA base editors," Nature, May 16, 2019, 569(7756):433-437, 18 pages.
Guilinger et al., "Fusion of Catalytically Inactive Cas9 to FokI Nuclease Improves the Specificity of Genome Modification," Nat Biotechnol., Apr. 2014, 32:577-582.
Guo et al., "Structural insights into a high fidelity variant of SpCas9," Cell Res., 2019, 29:183-192.
Hale et al., "Essential Features and Rational Design of CRISPR RNAs That Function With the Cas RAMP Module Complex to Cleave RNAs," Mol Cell., Feb. 2012, 45(3):292-302.
Harper et al., "Protective alleles and modifier variants in human health and disease," Nat Rev Genetics, 2015, 16:689-701.
Heigwer et al., "E-CRISP: fast CRISPR target site identification," Nat Methods, Feb. 2014, 11:122-123.
Heler et al., "Cas9 specifies functional viral targets during CRISPR-Cas adaptation," Nature, 2015, 519:199-202.
Hirano et al., "Structural Basis for the Altered PAM Specificities of Engineered CRISPR-Cas9," Mol Cell, Mar. 2017, 61:886-94.
Horvath et al., "Diversity, activity, and evolution of CRISPR loci in *Streptococcus thermophilus*," J. Bacteriol., Feb. 2008, 190:1401-1412.

Hou et al, "Efficient genome engineering in human pluripotent stem cells using Cas9 from Neisseria meningitidis," Proc. Natl. Acad. Sci. USA, Sep. 2013, 110(39):15644-15649.
Hsu et al., "Development and Applications of CRISPR-Cas9 for Genome Engineering," Cell, 2014, 157(6):1262-1278.
Hsu et al., "DNA targeting specificity of RNA-guided Cas9 nucleases," Nat Biotechnol., 2013, 31:827-832.
Hu et al., "Evolved Cas9 variants with broad PAM compatibility and high DNA specificity," Nature, 2018, 556:57-63.
Hwang et al., "Efficient In Vivo Genome Editing Using RNA-Guided Nucleases," Nat Biotechnol., 2013, 31:227-229 (Author Manuscript).
Iyer et al., "Prediction of novel families of enzymes involved in oxidative and other complex modifications of bases in nucleic acids," Cell Cycle, 2009, 8(11):1698-710.
Jiang et al., "A Cas9-guide RNA complex preorganized for target DNA recognition," Science, Jun. 2015, 348(6242):1477-1481.
Jiang et al., "CRISPR-assisted editing of bacterial genomes," Nat Biotechnol., 2013, 31:233-239 (Author Manuscript).
Jiang et al., "Structures of a CRISPR-Cas9 R-loop complex primed for DNA cleavage," Science, Feb. 2016, 351(6275):867-871.
Jinek et al., "A programmable dual-RNA-guided DNA endonuclease in adaptive bacterial immunity," Science, 2012, 337:816-821.
Jinek et al., "RNA-programmed genome editing in human cells," Elife, 2013, 2:e00471, 9 pages.
Jinek et al., "Structures of Cas9 endonucleases reveal RNA-mediated conformational activation," Science, Mar. 2014, 343(6176):1247997, 13 pages.
Kan et al., "Mechanisms of precise genome editing using oligonucleotide donors," Genome Res., 2017, 27:1099-1111.
Karvelis et al., "Rapid characterization of CRISPR-Cas9 protospacer adjacent motif sequence elements," Genome Biol., 2015, 16:253, 13 pages.
Keegan et al., "ADAR RNA editing below the backbone," RNA, Sep. 2017, 23(9):1317-1328.
Kim et al., "Deep learning improves prediction of CRISPR-Cpf1 guide RNA activity," Nature Biotechnology, Jan. 29, 2018, 36:239-241, 6 pages.
Kim et al., "SpCas9 activity prediction by DeepSpCas9, a deep learning-based model with high generalization performance," Science Advances, Nov. 6, 2019, 5(11):eaax9249, 9 pages.
Kim et al., "Genome-wide target specificities of CRISPR-Cas9 nucleases revealed by multiplex Digenome-seq," Genome Res, 2016, 26: 406-415.
Kleinstiver et al., "A unified genetic, computational and experimental framework identifies functionally relevant residues of the homing endonuclease I-BmoI," Nucleic Acids Res., 2010, 38(7):2411-2427.
Kleinstiver et al., "Engineered CRISPR-Cas12a variants with increased activities and improved targeting ranges for gene, epigenetic and base editing," Nat Biotechnol., Feb. 11, 2019, 37:276-282.
Kleinstiver et al., "High-fidelity CRISPR-Cas9 nucleases with no detectable genome-wide offtarget effects," Nature, Jan. 2016, 529:490-495.
Kleinstiver et al., "Broadening the targeting range of Staphylococcus aureus CRISPR-Cas9 by modifying PAM recognition," Nature Biotechnology, Dec. 2015, 33(12):1293-1298.
Kleinstiver et al., "Engineered CRISPR-Cas9 nucleases with altered PAM specificities," Nature, 2015, 523(7561):481-485.
Koblan et al., "Improving cytidine and adenine base editors by expression optimization and ancestral reconstruction," Nat Biotechnol., Oct. 2018, 36:843-846.
Komor et al., "Improved base excision repair inhibition and bacteriophage Mu Gam protein yields C:G-to-T:A base editors with higher efficiency and product purity," Sci. Adv., Aug. 2017, 3:eaao4774, 9 pages.
Komor et al., "CRISPR-Based Technologies for the Manipulation of Eukaryotic Genomes," Cell, Jan. 12, 2017, 168(1-2):20-36.
Komor et al., "Programmable editing of a target base in genomic DNA without double-stranded DNA cleavage," Nature, May 2016, 533(7603):420-424.

(56) References Cited

OTHER PUBLICATIONS

Lin et al., "CRISPR/Cas9 systems have off-target activity with insertions or deletions between target DNA and guide RNA sequences," Nucleic Acids Res., 2014, 42:7473-7485.
Lindahl et al., "DNA N-glycosidases: properties of uracil-DNA glycosidase from *Escherichia coli*," J. Biol. Chem., May 1977, 252:3286-3294.
Makarova et al., "Evolution and classification of the CRISPR-Cas systems," Nat. Rev. Microbiol., 2011, 9(6):467-77.
Mali et al., "Cas9 as a versatile tool for engineering biology," Nature Methods, 2013, 10(10):957-963.
Mali et al., "RNA-guided human genome engineering via Cas9," Science, Feb. 2013, 339:823-826 (Author Manuscript).
Mali et al., "CAS9 transcriptional activators for target specificity screening and paired nickases for cooperative genome engineering," Nat Biotechnol, Sep. 2013, 31(9): 833-838.
McShan et al., "Genome sequence of a nephritogenic and highly transformable M49 strain of *Streptococcus pyogenes*," J. Bacteriol., 2008, 190:7773-7785.
Melamede et al., "Isolation and characterization of endonuclease VIII from *Escherichia coli*," Biochemistry, Feb. 1994, 33:1255-1264.
Mojica et al., "Short motif sequences determine the targets of the prokaryotic CRISPR defence system," Microbiology, Jan. 2009, 155:733-740.
Nishida et al, "Targeted nucleotide editing using hybrid prokaryotic and vertebrate adaptive immune systems," Science, Sep. 2016, 53(6305), 14 pages.
Nishimasu et al., "Crystal structure of Cas9 in complex with guide RNA and target DNA," Cell, 2014, 156:935-949.
Nishimasu et al., "Engineered CRISPR-Cas9 nuclease with expanded targeting space," Science, Sep. 21, 2018, 361(6408):1259-1262.
PCT International Preliminary Report on Patentability in International Appln. No. PCT/US2016/020756, dated Sep. 14, 2017.
PCT International Preliminary Report on Patentability in International Appln. No. PCT/US2016/049147, dated Mar. 6, 2018, 8 pages.
PCT International Preliminary Report on Patentability in International Appln. No. PCT/US2018/036293, dated Dec. 10, 2019, 8 pages.
PCT International Preliminary Report on Patentability in International Appln. No. PCT/US2018/047577, dated Feb. 25, 2020, 8 pages.
PCT International Search Report and Written Opinion in International Appln. No. PCT/US2016/020756, dated Jul. 26, 2016, 12 pages.
PCT International Search Report and Written Opinion in International Appln. No. PCT/US2016/049147, dated Dec. 23, 2016, 12 pages.
PCT International Search Report and Written Opinion in International Appln. No. PCT/US2017/043753, dated Dec. 28, 2017, 18 pages.
PCT International Search Report and Written Opinion in International Appln. No. PCT/US2018/028919, dated Oct. 1, 2018, 17 pages.
PCT International Search Report and Written Opinion in International Appln. No. PCT/US2018/036293, dated Nov. 8, 2018, 13 pages.
PCT International Search Report and Written Opinion in International Appln. No. PCT/US2021/014900, dated Jul. 21, 2021, 12 pages.
PCT International Search Report and Written Opinion in International Appln. No. PCT/US2021/014933, dated Jul. 20, 2021, 12 pages.
PCT Invitation to Pay Additional Fees in International Appln. No. PCT/US2016/049147, dated Oct. 31, 2016, 2 pages.
Perez-Pinera et al., "RNA-guided gene activation by CRISPR-Case9-based transcription factors," Nat Methods, 2013, 10(10):973-976.

Pinello et al, "Analyzing CRISPR genome-editing experiments with CRISPResso," Nat. Biotechnol., Jul. 2016, 34(7): 695-697.
Ran et al., "Double Nicking by RNA-Guided CRISPR Cas9 for Enhanced Genome Editing Specificity," Cell, 2013, 154(6):1380-1389.
Ran et al., "In vivo genome editing using *Staphylococcus aureus* Cas9," Nature, 2015, 520:186-191.
Rees et al., "Base editing: precision chemistry on the genome and transcriptome of living cells," Nat. Rev. Genet., Dec. 2018, 19(12):770-788.
Reyon et al, "FLASH assembly of TALENs for high-throughput genome editing," Nat. Biotechnol., May 2012, 30(5):460-465.
Rohland et al., "Cost-effective, high-throughput DNA sequencing libraries for multiplexed target capture," Genome Research, Jan. 2012, 22:939-946.
Rutkauskas et al., "Directional R-Loop Formation by the CRISPR-Cas Surveillance Complex Cascade Provides Efficient off-Target Site Rejection," Cell Rep., Mar. 2015, 10(9):1534-1543.
Sander et al., "CRISPR-Cas systems for editing, regulating and targeting genomes," Nat Biotechnol., Apr. 2014, 32(4):347-55.
Sang, "Prospects for transgenesis in the chick," Mechanisms of Development, Sep. 2004, 121:1179-1186.
Sapranauskas et al, "The *Streptococcus thermophilus* CRISPR/Cas system provides immunity in *Escherichia coli*," Nucleic Acids Res., Aug. 2011, 39(21):9275-9282.
Savva et al., "The ADAR protein family," Genome Biol., Dec. 2012, 13(12):252, 10 pages.
Schuelke et al., "Myostatin Mutation Associated with Gross Muscle Hypertrophy in a Child," New Engl J Med., 2004, 350:2682-2688.
Shah et al, "Protospacer recognition motifs," RNA Biol., Feb. 2013, 10(5):891-899.
Shi et al., "Discovery of cancer drug targets by CRISPR-Cas9 screening of protein domains," Nat Biotechnol., 2015, 33:661-7.
Slaymaker et al, "Rationally engineered Cas9 nucleases with improved specificity," Science, Jan. 2016, 351(6268):84-88.
Spencer et al., "Deep mutational scanning of S. pyogenes Cas9 reveals important functional domains," Scientific Reports, Dec. 4, 2017, 7(16836), 14 pages.
Sternberg et al., "Conformational control of DNA target cleavage by CRISPR-Cas9" Nature, 2015, 527:110-113.
Sternberg et al., "DNA interrogation by the CRISPR RNA-guided endonuclease Cas9," Nature, Jan. 2014, 507(7490):62-67.
Suzuki et al., "In vivo genome editing via CRISPR/Cas9 mediated homology-independent targeted integration," Nature, 2016, 540:144-149.
Szczelkun et al., "Direct observation of R-loop formation by single RNA-guided Cas9 and Cascade effector complexes," Proc. Natl. Acad. Sci. USA., 111(27):9798-9803.
TG and HDL Working Group of the Exome Sequencing Project, National Heart, Lung, and Blood Institute, "Loss-of-function mutations in APOC3, triglycerides, and coronary disease," New Engl J Med., 2014, 371:22-31.
The Myocardial Infarction Genetics Consortium Investigators, "Inactivating mutations in NPCIL1 and protection from coronary heart disease," New Engl J Med., 2014, 371:2072-82.
Tsai & Joung., "Defining and improving the genome-wide specificities of CRISPR-Cas9 nucleases," Nat. Rev. Genet., 2016, 17(5):300-312.
Tsai et al., "Dimeric CRISPR RNA-guided FokI nucleases for highly specific genome editing," Nat. Biotechnol., 2014, 32(6):569-576.
Tsai et al., "GUIDE-Seq enables genome-wide profiling of off-target cleavage by CRISPR-Cas nucleases," Nat Biotechnol, Feb. 2015, 33:187-197.
UniProt Database Accession No. USULJ7, "Full=Csn1 family CRISPR-associated protein," Jan. 22, 2014, 1 page.
Vakulskas et al, "A high-fidelity Cas9 mutant delivered as a ribonucleoprotein complex enables efficient gene editing in human haematopoietic stem and progenitor cells," Nature Medicine, Aug. 2018, 24(8):1216-1224.
Vierstra et al, "Functional footprinting of regulatory DNA," Nat. Methods, Oct. 2015, 12(10):927-30.

(56) References Cited

OTHER PUBLICATIONS

Walton et al., "Unconstrained genome targeting with near-PAMless engineered CRISPR-Cas9 variants," Science, Apr. 17, 2020, 368:290-296, 7 pages.
Wang et al., Regenerative medicine: targeted genome editing in vivo. Cell Research, Jan. 2015, 25: 271-272.
Wiedenheft et al, "RNA-guided genetic silencing systems in bacteria and archaea," Nature, 2012, 482:331-338.
Wolf et al, "tadA, an essential tRNA-specific adenosine deaminase from *Escherichia coli*," Embo J., Jul. 2002, 21(14):3841-3851.
Wright et al., "Rational design of a split-Cas9 enzyme complex," Proc. Natl. Acad. Sci. USA., Mar. 2015, 112(10):2984-2989.
Zetsche et al., "Cpf1 Is a Single RNA-Guided Endonuclease of a Class 2 CRISPR-Cas System," Cell, 2015, 163:759-771.
Zhang et al., "Comparison of non-canonical PAMS for CRISPR/Cas9-mediated DNA cleavage in human cells," Sci Rep, Jun. 2014, 4:5405, 5 pages.
Zhang et al., "Processing-Independent CRISPR RNAs Limit Natural Transformation in Neisseria meningitidis," Mol Cell, May 2013, 50(4):488-503.
Nishimasu et al., "Crystal Structure of *Staphylococcus aureus* Cas9," Cell, 2015, 162:1113-1126.
Nishimasu et al., "Supplemental Information: Crystal Structure of *Staphylococcus aureus* Cas9," Cell, 2015, 11 pages.
Lee et al., "Directed evolution of CRISPR-Cas9 to increase its specificity," Nat Commun., Aug. 2018, 9(1):3048, 10 pages.
Partial European Search Report in European Appln. No. 21744577.4, dated Dec. 19, 2023, 21 pages.
Xu et al., "SpRY greatly expands the genome editing scope in rice with highly flexible PAM recognition," Jan. 2021, 22(1):6, 15 pages.
Li et al., "Advances in detecting and reducing off-target effects generated by CRISPR-mediated genome editing," Journal of Genetics and Genomics, Nov. 2019, 46(11):513-521.
Extended European Search Report in European Appln. No. 21744577.4, dated Mar. 12, 2024, 19 pages.

\* cited by examiner

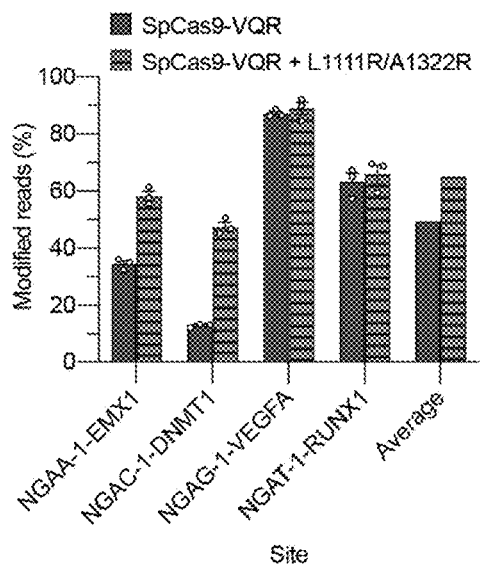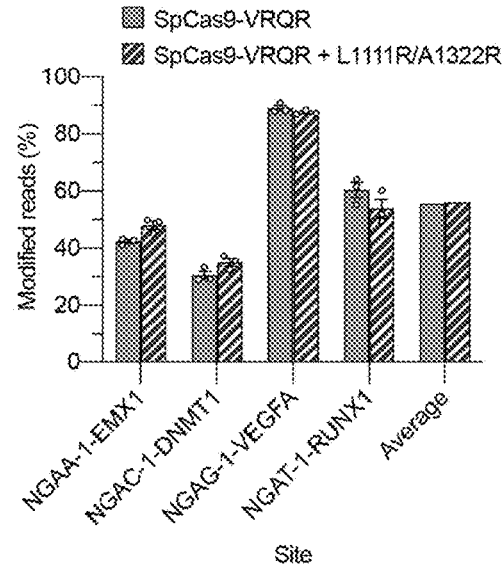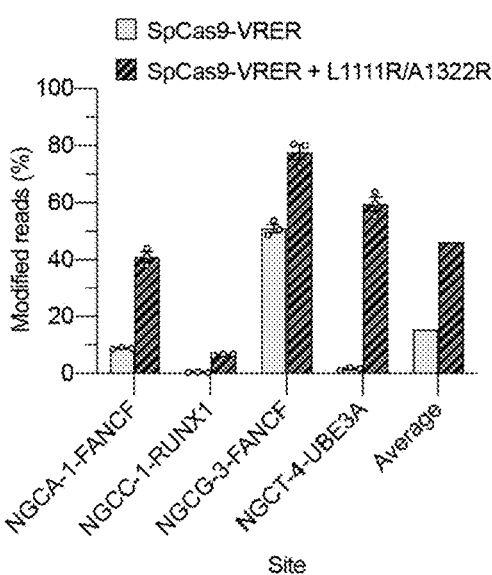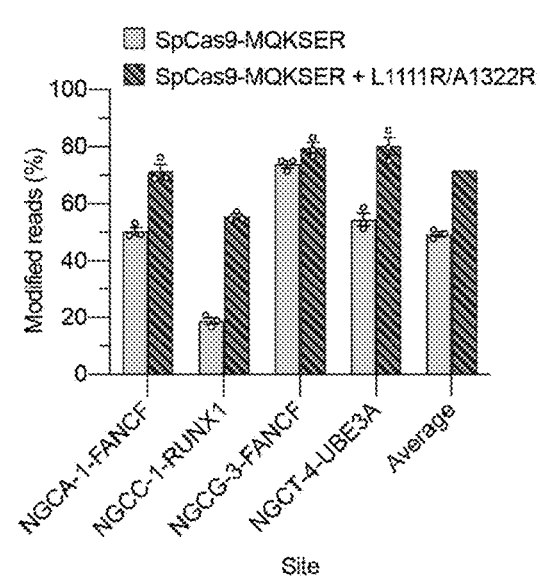
FIGs. 4A-D

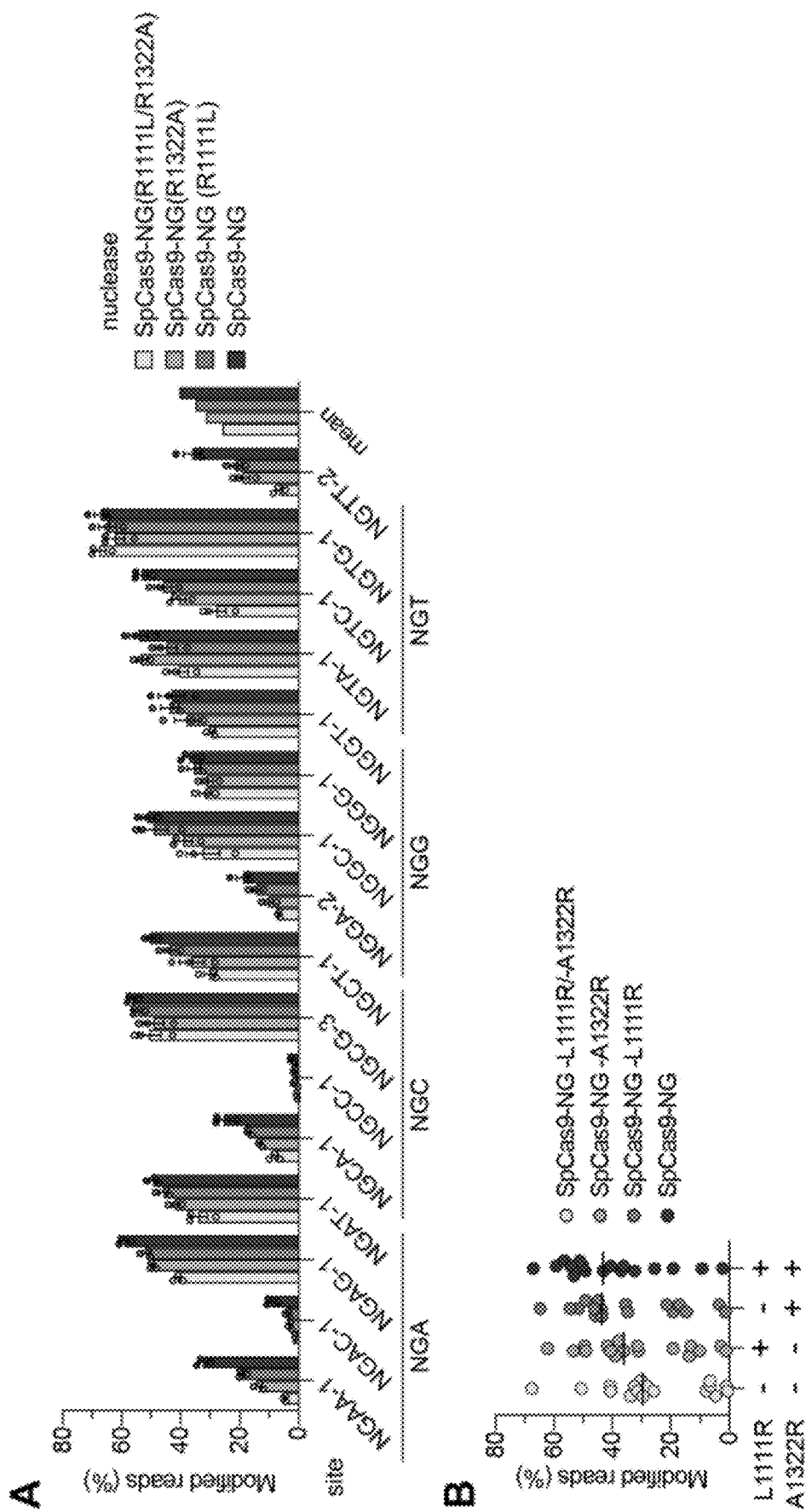
FIGs. 7A-B

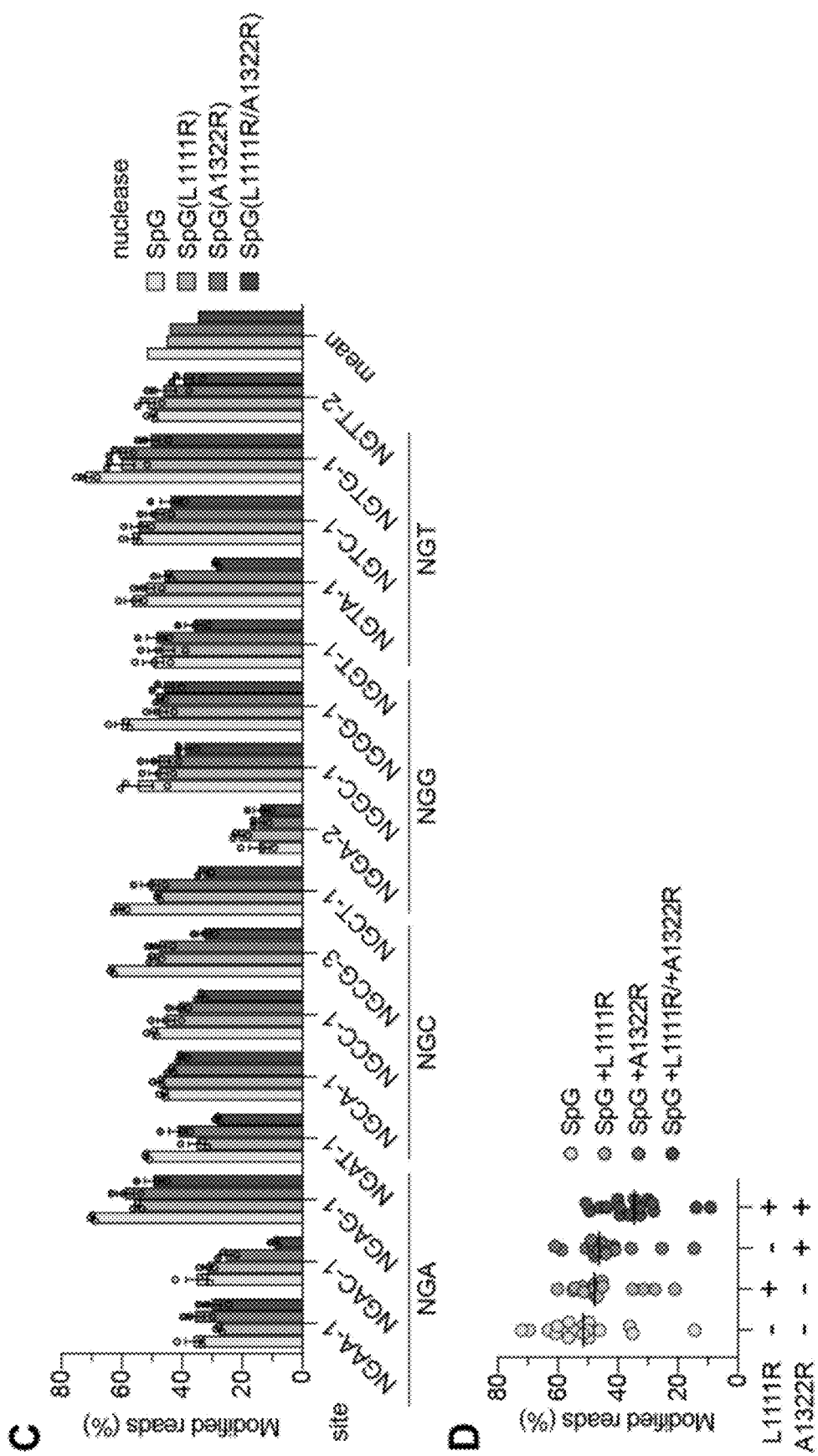
FIGs. 7C-D

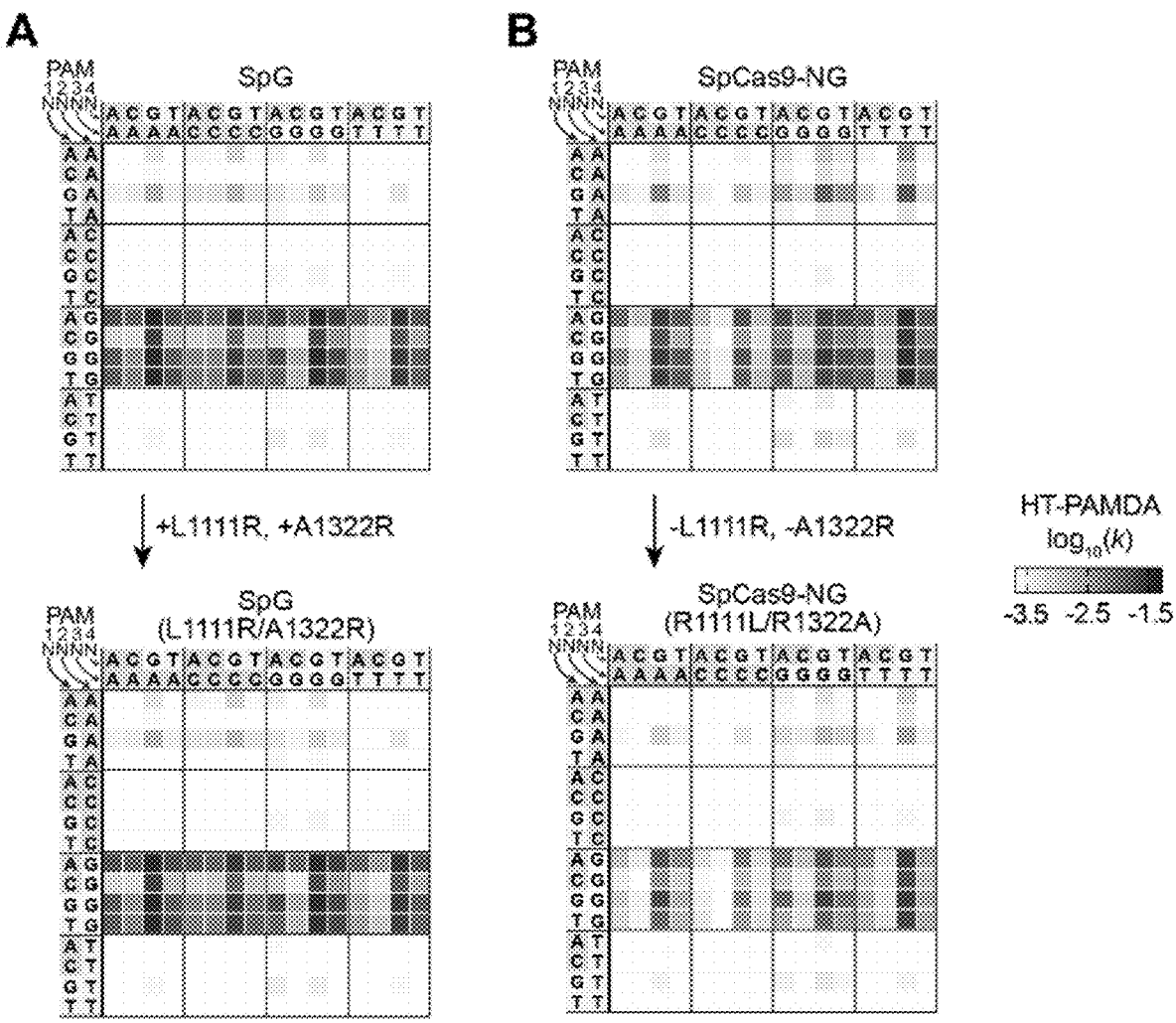
FIGs. 8A-B

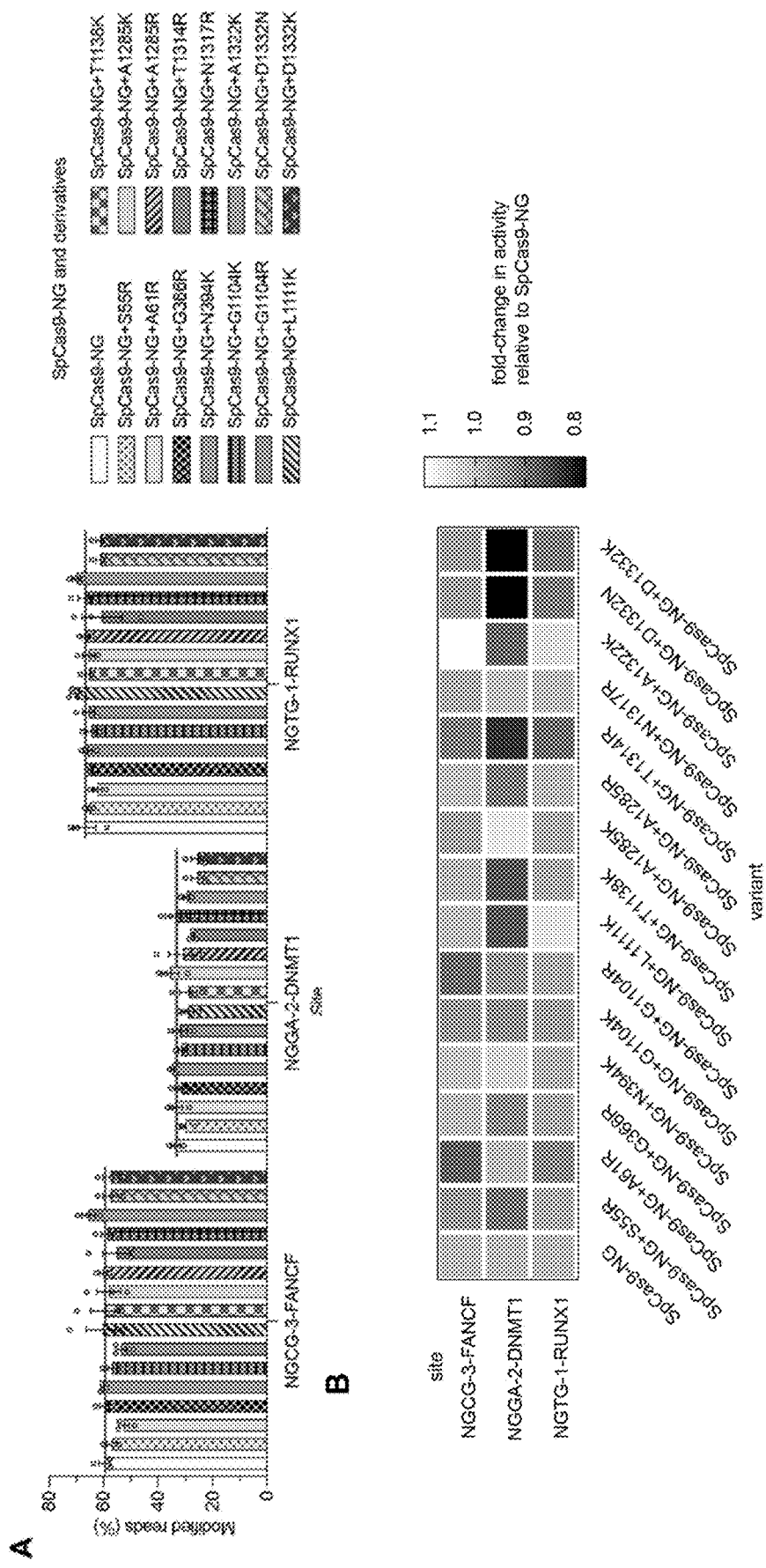
FIGs. 9A-B

FIGs. 9C-D
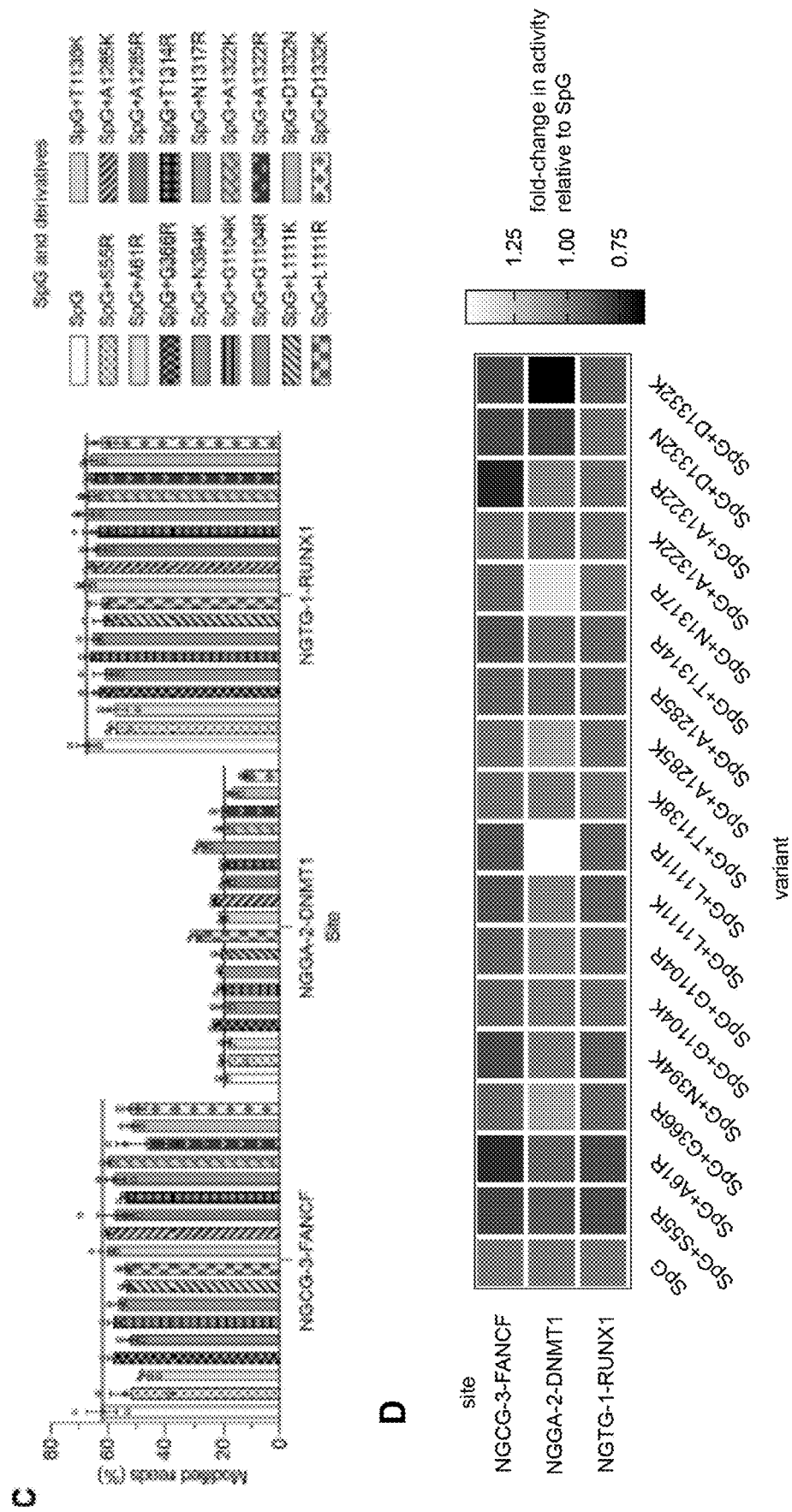

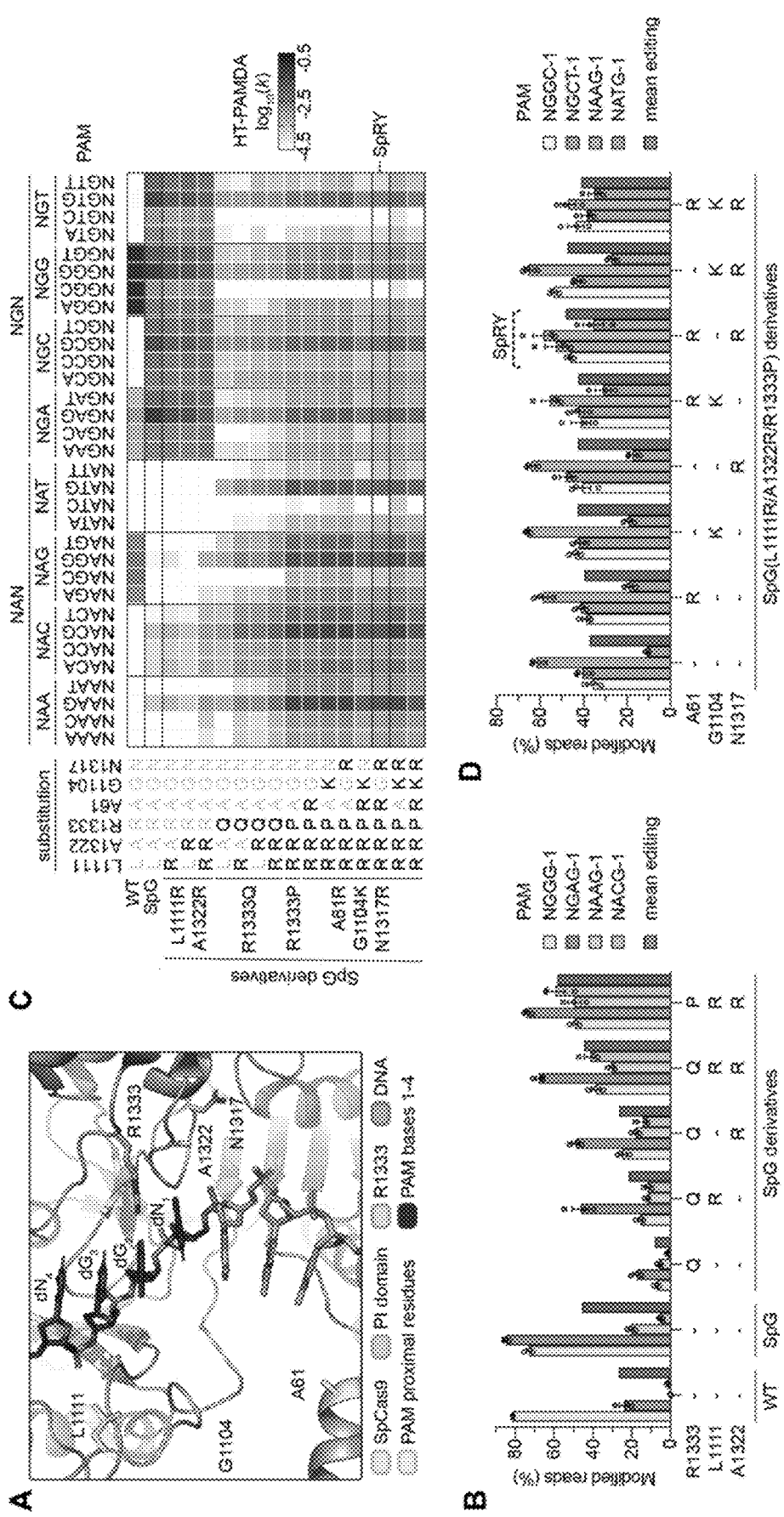
FIGs. 10A-D

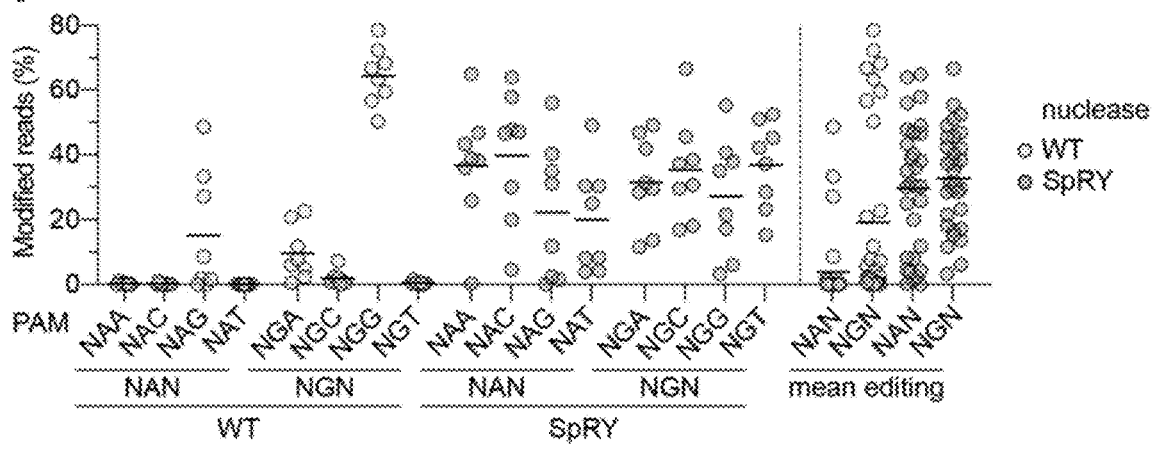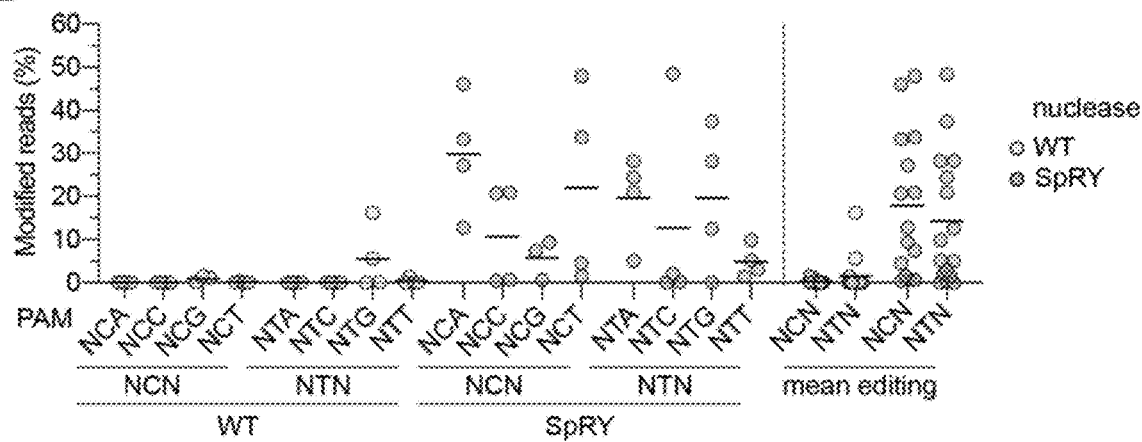
FIGs. 12A-B

CRISPR-Cas ENZYMES WITH ENHANCED ON-TARGET ACTIVITY

CLAIM OF PRIORITY

This application claims the benefit of U.S. Provisional Patent Application Ser. No. 62/965,671, filed on Jan. 24, 2020. The entire contents of the foregoing are hereby incorporated by reference.

FEDERALLY SPONSORED RESEARCH OR DEVELOPMENT

This invention was made with Government support under Grant No. CA218870 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Mar. 12, 2021, is named "SequenceListing" and is 16,384 bytes in size.

TECHNICAL FIELD

Engineered versions of *Streptococcus pyogenes* Cas9 (SpCas9) and SpCas9 variants that have improved on-target editing capabilities, and methods of use thereof.

BACKGROUND

The custom manipulation of nucleic acid sequences in living cells has been vastly simplified by the adaptation of CRISPR enzymes and the development of base editors (BEs) for genome editing[1-4]. For these technologies to efficiently introduce user-specified genetic changes, one critical parameter for use is the level of on-target editing that can be achieved. In the absence of moderate-to-high levels of editing, many applications are rendered ineffective or unachievable. While efforts have been pursued to determine single guide-RNA (sgRNA) and target-site dependent properties that modulate editing activity[5-7], no large-scale assessment of protein-mediated CRISPR enzyme properties has been conducted.

SUMMARY

Described herein are variants of SpCas9 with enhanced on-target activity. Provided herein are isolated *Streptococcus pyogenes* Cas9 (SpCas9) proteins with mutations at one, two, three, four, five, or more of the positions shown in Table 1, 2, or 3, wherein if only one mutation is present, the mutation is not G1218R; L1111R; A1322R; D1332K; N394K; R221K; L1245V; E1243K; or E1253K. In some embodiments, the protein includes a mutation at G1218R; L1111R; A1322R; D1332K; N394K; R221K; L1245V; E1243K; and/or E1253K, and at least one other mutation shown in Table 1 or 2. In some embodiments, the protein includes a mutation or combination of mutations shown in any one of the figures. In some embodiments, these variants of SpCas9 have enhanced on-target activity as compared to a reference protein that lacks this mutation but is otherwise identical.

In some embodiments, the proteins comprise a sequence that is at least 80% identical to the amino acid sequence of SEQ ID NO:1.

In some embodiments, the proteins comprise at least one of the following mutations: G1104X, e.g., G1104K or G1104R; A61X, e.g., A61R; N1317X, e.g., N1317R; S55X, e.g., S55R; T1314X, e.g., T1314R; G366X, e.g., G366R; A1285X, e.g., A1285R or A1285K; D1332X, e.g., D1332R or D1332H or D1332Q or D1332N; K1151X, e.g., K1151R; T1138X, e.g., T1138K or T1138R; V1139X, e.g., V1139T; K1289X, e.g., K1289R; A1322X, e.g., A1322K; and/or L1111X, e.g., L1111K, wherein if only one mutation is present, the mutation is not L1111R, A1322R, or D1332K.

In some embodiments, the proteins comprise mutations at A61R/N1317R, G1104K/N1317R, A61R/G1104K, S55R/G1104K, S55R/A61R, S55R/N1317R, G1104K/T1314R, A61R/T1314R, T1314R/N1317R, S55R/T1314R, A61R/G1104R, G1104R/N1317R, S55R/G1104R, G1104R/T1314R, G366R/G1104K, S55R/G366R, A61R/G366R, G366R/N1317R, G366R/T1314R, G366R/G1104R, G1104K/A1285R, A61R/A1285R, A1285R/N1317R, S55R/A1285R, A1285R/T1314R, G1104R/A1285R, G366R/A1285R, G1104K/A1285K, A61R/A1285K, A1285K/N1317R, S55R/A1285K, A1285K/T1314R, G1104R/A1285K, G366R/A1285K, G1104K/D1332R, A61R/D1332R, D1332R/N1317R, S55R/D1332R, D1332R/T1314R, G1104R/D1332R, G366R/D1332R, A1285K/D1332R, A1285R/D1332R, A61R/G1104K/N1317R, A61R/L1111R, A61R/A1322R, A61R/L1111R/A1322R, G1104K/L1111R, G1104K/A1322R, G1104K/L1111R/A1322R, N1317R/L1111R, N1317R/A1322R, N1317R/L1111R/A1322R, A61R/N1317R/L1111R, A61R/N1317R/A1322R, A61R/N1317R/L1111R/A1322R, G1104K/N1317R/L1111R, G1104K/N1317R/A1322R, G1104K/N1317R/L1111R/A1322R, A61R/G1104K/L1111R, A61R/G1104K/A1322R, A61R/G1104K/L1111R/A1322R, S55R/L1111R, S55R/A1322R, S55R/L1111R/A1322R, G366R/L1111R, G366R/A1322R, G366R/L1111R/A1322R, N394K/L1111R, N394K/A1322R, N394K/L1111R/A1322R, A1285K/L1111R, A1285K/A1322R, A1285K/L1111R/A1322R, D1332K/L1111R, D1332K/A1322R, or D1332K/L1111R/A1322R.

In some embodiments, the proteins further comprise one or more mutations that decrease nuclease activity selected from the group consisting of mutations at D10, E762, D839, H983, or D986; and at H840 or N863. In some embodiments, the mutations are: (i) D10A or D10N, and (ii) H840A, H840N, or H840Y.

In some embodiments, the proteins further comprise one or more mutations that increase specificity selected from the group consisting of mutations at N497, R661, N692, M694, Q695, H698, K810, K848, Q926, K1003, R0160, R691, M495, Y515, K526, and/or R661.

In some embodiments, the proteins further comprise mutations at R691A, M495V, Y515N, K526E, R661Q, R661L, R661S, Y450A/Q695A, L169A/Q695A, Q695A/Q926A, Q695A/D1135E, Q926A/D1135E, Y450A/D1135E, L169A/Y450A/Q695A, L169A/Q695A/Q926A, Y450A/Q695A/Q926A, R661A/Q695A/Q926A, N497A/Q695A/Q926A, Y450A/Q695A/D1135E, Y450A/Q926A/D1135E, Q695A/Q926A/D1135E, L169A/Y450A/Q695A/Q926A, L169A/R661A/Q695A/Q926A, Y450A/R661A/Q695A/Q926A, N497A/Q695A/Q926A/D1135E, R661A/Q695A/Q926A/D1135E, and Y450A/Q695A/Q926A/D1135E; N692A/M694A/Q695A/H698A, N692A/M694A/Q695A/H698A/Q926A; N692A/M694A/Q695A/Q926A; N692A/M694A/H698A/Q926A; N692A/Q695A/H698A/

Q926A; M694A/Q695A/H698A/Q926A; N692A/Q695A/ H698A; N692A/M694A/Q695A; N692A/H698A/Q926A; N692A/M694A/Q926A; N692A/M694A/H698A; M694A/ Q695A/H698A; M694A/Q695A/Q926A; Q695A/H698A/ Q926A; G582A/V583A/E584A/D585A/N588A/Q926A; G582A/V583A/E584A/D585A/N588A; T657A/G658A/ W659A/R661A/Q926A; T657A/G658A/W659A/R661A; F491A/M495A/T496A/N497A/Q926A; F491A/M495A/ T496A/N497A; K918A/V922A/R925A/Q926A; or 918A/ V922A/R925A; K855A; K810A/K1003A/R1060A; K848A/K1003A/R1060A; M495V/Y515N/K526E/R661Q; M495V/Y515N/K526E/R1060A; or M495V/Y515N/K526E/ R661S.

Also provided herein are fusion proteins comprising the isolated proteins fused to a heterologous functional domain, with an optional intervening linker, wherein the linker does not interfere with activity of the fusion protein.

In some embodiments, the heterologous functional domain is a transcriptional activation domain. In some embodiments, the transcriptional activation domain is from VP16, VP64, rTA, NF-κB p65, or the composite VPR (VP64-p65-rTA).

In some embodiments, the heterologous functional domain is a transcriptional silencer or transcriptional repression domain. In some embodiments, the transcriptional repression domain is a Krueppel-associated box (KRAB) domain, ERF repressor domain (ERD), or mSin3A interaction domain (SID). In some embodiments, the transcriptional silencer is Heterochromatin Protein 1 (HP1).

In some embodiments, the heterologous functional domain is an enzyme that modifies the methylation state of DNA. In some embodiments, the enzyme that modifies the methylation state of DNA is a DNA methyltransferase (DNMT) or a TET protein. In some embodiments, the TET protein is TET1.

In some embodiments, the heterologous functional domain is an enzyme that modifies a histone subunit.

In some embodiments, the enzyme that modifies a histone subunit is a histone acetyltransferase (HAT), histone deacetylase (HDAC), histone methyltransferase (HMT), or histone demethylase.

In some embodiments, the heterologous functional domain is a base editor or a prime editor. In some embodiments, the base editor is a DNA or RNA deaminase, e.g., a cytosine or adenine deaminase domain, or activation-induced cytidine deaminase; or wherein the prime editor comprises a reverse transcriptase (RT) domain.

In some embodiments, the heterologous functional domain is a biological tether. In some embodiments, the biological tether is MS2, Csy4 or lambda N protein.

In some embodiments, the heterologous functional domain is FokI.

Also provided herein are isolated nucleic acids encoding a protein described herein, as well as vectors comprising the isolated nucleic acids. In some embodiments, the isolated nucleic acid is operably linked to one or more regulatory domains for expressing an isolated Streptococcus pyogenes Cas9 (SpCas9) protein as described herein, preferably with mutations at one, two or more of the positions shown in Tables 2 or 3.

Also provided herein are host cells, preferably mammalian host cells, comprising the nucleic acids described herein, and optionally expressing one or more of the proteins described herein.

Further provided herein are methods for altering the genome of a cell. The methods comprise expressing in the cell, or contacting the cell with, an isolated protein or fusion protein as described herein, and a suitable guide RNA (or prime RNA for prime editors) having a region complementary to a selected portion of the genome of the cell.

In some embodiments, the isolated protein or fusion protein comprises one or more of a nuclear localization sequence, cell penetrating peptide sequence, and/or affinity tag.

In some embodiments, the cell is a stem cell. In some embodiments, the cell is an embryonic stem cell, mesenchymal stem cell, or induced pluripotent stem cell; is in a living animal; or is in an embryo.

Also provided herein are methods for altering a double stranded DNA (dsDNA) molecule, the method comprising contacting the dsDNA molecule with an isolated protein or fusion protein as described herein, and a guide RNA (or prime RNA for prime editors) having a region complementary to a selected portion of the dsDNA molecule.

In some embodiments, the dsDNA molecule is in vitro.

In some embodiments, the fusion protein and RNA are in a ribonucleoprotein complex. The ribonucleoprotein complexes are also provided herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 4A-D. Compatibility of SpCas9 PAM variants with activity-enhancing substitutions. A-D, Modification of sites in HEK 293T cells by SpCas9 PAM variants and derivatives harboring L1111R and A1322R substitutions (SpCas9-VQR[8], -VRQR[9], -VRER[8], and -MQKSER in panels A-D, respectively). Percent modified reads in panels A-D assessed by targeted sequencing; mean, s.e.m., and individual data points shown for n=3.

FIGS. 7A-D. Compatibility of SpCas9-NG and SpG with activity-enhancing substitutions. A-D, Modification of 16 sites in HEK 293T cells bearing NGNN PAMs by SpCas9-NG[13] and derivatives lacking one or both of the requisite L1111R and A1322R substitutions (bar plots of data in panel A; summary of data in panel B), or by SpG and derivatives harboring one or both of the L1111R and A1322R substitutions (bar plots of data in panel C; summary of data in panel D). Percent modified reads in panels A-D assessed by targeted sequencing; mean, s.e.m., and individual data points shown for n=3 in panels A and C; mean data points shown in panels B and D with mean of the 16 values indicated.

FIGS. 8A-B. High-throughput PAM determination assay (HT-PAMDA) characterization of NGN PAM variants. A, B, HT-PAMDA NNNN PAM profiles showing ability to target all possible 256 NNNN sequences, with SpG and the SpG (L1111R/A1322R) variant (panel A), as well as SpCas9-NG and SpCas9-NG without the requisite L1111R and A1322R substitutions (panel B). For HT-PAMDA data, the log 10(k) values are the mean of at least two replicates against two distinct spacer sequences.

FIGS. 9A-D. Activities of NGN PAM-targeting SpCas9 variants bearing additional novel substitutions to improve on-target editing. A, Modification of endogenous sites in HEK 293T cells bearing NGN PAMs by SpCas9-NG[3] and derivative variants encoding substitutions that putatively improve on-target editing. Percent modified reads assessed by targeted sequencing; mean, s.e.m., and individual data points shown for n=3; red line indicates mean modification with SpCas9-NG. B, quantification of the editing activities in panel A normalized to the levels of editing observed with SpCas9-NG. The normalized activities of variants that improve on-target activity are shown in the blue, and the activities of variants that abrogate activity are shown in red. C, Modification of endogenous sites in HEK 293T cells bearing NGN PAMs by SpG and derivative variants encoding substitutions that putatively improve on-target editing. Percent modified reads assessed by targeted sequencing; mean, s.e.m., and individual data points shown for n=3; red line indicates mean modification with SpG. D, quantification of the editing activities in panel C normalized to the levels of editing observed with SpG. The normalized activities of variants that improve on-target activity are shown in the blue, and the activities of variants that abrogate activity are shown in red.

FIGS. 10A-D. Engineering and characterization of SpCas9 variants with expanded targeting and enhanced activities. A, Representative crystal structure of SpCas9 to illustrate amino acid side chains of R1333 and selected PAM-proximal residues whose substitution might improve on-target activity. The non-target strand (NTS) is hidden for clarity. Image generated from PDB ID 4UN3. B, Modification of endogenous sites in human cells bearing different NRN PAMs with WT SpCas9, SpG, and SpG derivatives. Editing assessed by targeted sequencing; mean, s.e.m., and individual data points shown for n=3. C, HT-PAMDA characterizations of WT SpCas9, SpG, and SpG derivatives to illustrate their NRNN PAM preferences. The $\log_{10}$ rate constants (k) are the mean of at least two replicates against two distinct spacer sequences. D, Modification of endogenous sites in human cells bearing different NRN PAMs SpG(L1111R/A1322R/R1333P) and derivatives bearing additional substitutions. Editing assessed by targeted sequencing; mean, s.e.m., and individual data points shown for n=3.

FIGS. 12A-F. Comparison of WT SpCas9 and SpRY nuclease and base editor activities across NNN PAM sites in human cells. A, B, Mean nuclease activity plots for WT SpCas9 and SpRY on 64 sites with NRN PAMs (panel A) and 31 sites with NYN PAMs (panel B) in human cells. The black line represents the mean of 8 or 3-4 sites (panels A and B, respectively) for each PAM of the indicated class. C, D, C-to-T base editing of endogenous sites in human cells bearing NRN and NYN PAMs (panels C and D, respectively) with WT SpCas9-CBE4max and SpRY-CBE4max constructs. Editing of cytosines in the edit window (positions 3 through 9) assessed by targeted sequencing; the five NYN PAM target sites were selected from high-activity sites in panel b; mean, s.e.m., and individual data points shown for n=3. E, F, A-to-G base editing of endogenous sites in human cells bearing NRN and NYN PAMs (panels E and F, respectively) with WT SpCas9-ABEmax and SpRY-ABEmax constructs. Editing of adenines in the edit window assessed by targeted sequencing; the five NYN PAM target sites were selected from high-activity sites in panel b; mean, s.e.m. and individual data points shown for n=3.

DETAILED DESCRIPTION

Figure 1A:
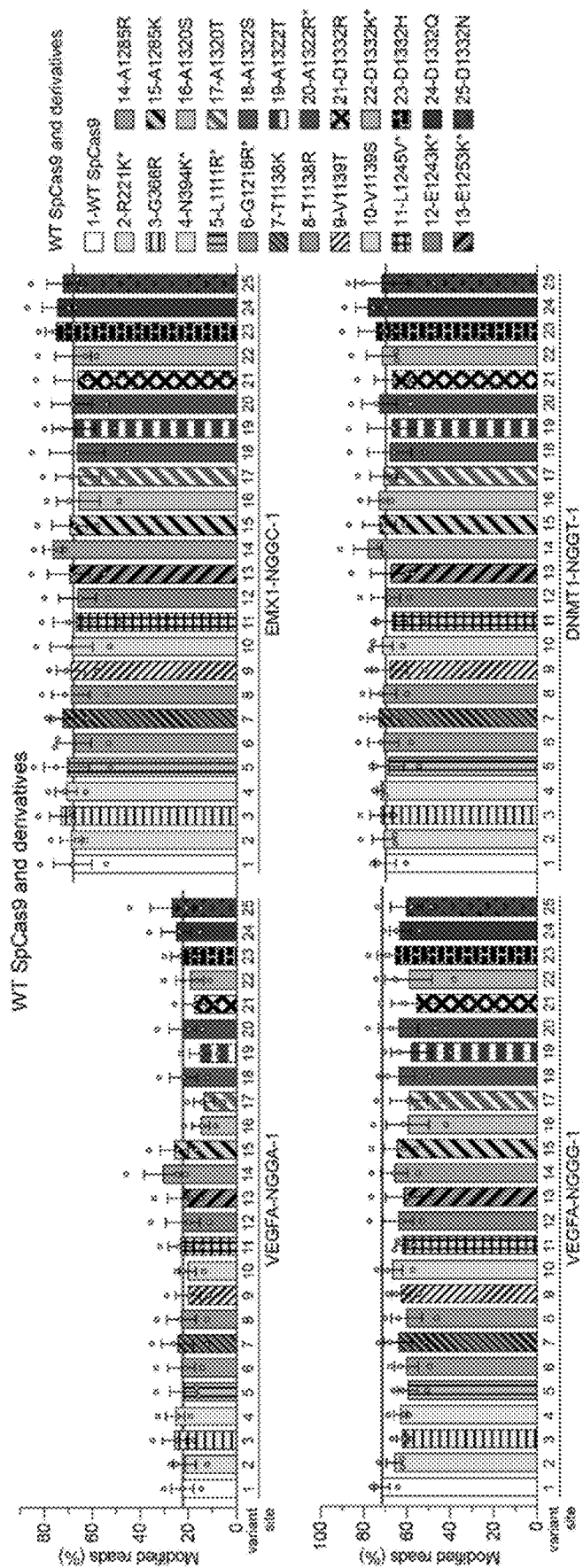
FIGS. 1A-B. Activities of WT SpCas9 and variants bearing substitutions to improve on-target editing. A, Modification of endogenous sites in HEK 293T cells bearing NGG PAMs by WT SpCas9 and derivative variants encoding substitutions that putatively improve on-target editing. Percent modified reads assessed by targeted sequencing; mean, s.e.m., and individual data points shown for n=3; red line indicates mean modification with WT SpCas9. The '*' symbol indicates variants previously described to improve on-target editing (R221K, N394K, L1245V, E1243K, E1253K in WT SpCas9 from ref[12]; G1218R in SpCas9-VRQR from refs[8,9]; L1111R and A1322R in SpCas9-NG from ref[13]; D1332K in SpCas9-QQR1 from ref[11]). B, quantification of the editing activities in panel A normalized to the levels of editing observed with WT SpCas9. The normalized activities of variants that improve on-target activity are shown in the blue, and the activities of variants that abrogate activity are shown in red.

One largely unexplored area of CRISPR technology development has been the design and engineering of enzymes with enhanced on-target activities. Given the near-ubiquitous successes achieved with wild-type *Streptococcus pyogenes* Cas9 (WT SpCas9), there has been little motivation to explore methods to improve on-target activity. We previously undertook a directed evolution approach to alter the PAM preference of SpCas9, leading us to SpCas9-VQR (D1135V/R1335Q/T1337R substitutions) variant that can target sites with NGA PAMs, and SpCas9-VRER (D1135V/G1218R/R1335E/T1337R substitutions) that can target NGCG PAMs[8]. We later found that the addition of G1218R to SpCas9-VQR to generate the SpCas9-VRQR variant led to greater on-target activity on sites with NGA PAMs[9]. During the course of these studies, we discovered that the G1218R and T1337R substitutions enhanced on-target editing of the PAM variants; we suspected that the G1218R and T1337R substitutions might form novel non-specific DNA backbone contacts, with the latter also potentially making a base specific contact to the fourth DNA base of the PAM. These hypotheses that were later validated by crystallography[10,11]. Collectively, this work was the first demonstration that amino acid residues of Cas9 could be modified to enhance activity.

Subsequent efforts by others to determine domain functions of SpCas9 using mutational scanning revealed the unexpected finding that certain substitutions in SpCas9 could generate modest improvements in on-target activity[12]. The roles of the R221K, N394K, L1245V, E1243K, E1253K substitutions that improve activity were not determined or elucidated. Furthermore, the rational design of an attenuated SpCas9 variant targeting NGN PAMs (named SpCas9-NG) required substitutions expected to stabilize Cas9-DNA interactions[13]. Nishimasu et al. found that along with our previously described G1218 and T1337R substitutions, additional supplementary non-specific contacts generated by L1111R and A1322R substitutions were necessary for SpCas9-NG to achieve sufficient on-target activity[13].

We also previously demonstrated that the activities of CRISPR-Cas12a enzymes could be rationally improved by generating novel PAM-proximal substitutions expected to relax PAM preference, with the unexpected finding that these mutations also enhanced on-target editing[14]. Our study revealed that amino acid substitutions in *Acidaminococcus* sp. Cas12a (AsCas12a) adjacent to the target or non-target DNA backbone that add novel contacts can improve editing with WT AsCas12a, as well as engineered AsCas12a variants capable of targeting novel PAM sequences[14]. These variants achieved improved on-target editing in vitro, at lower temperatures, as well as in human cells, for nuclease, epigenetic editing, and base editor experiments.

Despite these few studies that have demonstrated the prospect of improving on-target editing, no general strategy has been described for improving activity with SpCas9, engineered SpCas9 proteins with attenuated activities, as well as other Cas9, Cas12, Cas13, Cas14, and Cas3 orthologs that exhibit comparatively reduced levels of activity. Thus, the ability to engineer Cas proteins or BEs with enhanced on-target potencies would improve many applications of genome editing with CRISPR technologies.

Engineered Cas9 Variants with Altered PAM Specificities

The present disclosure provides engineered versions of SpCas9 and SpCas9 variants that have improved on-target editing capabilities. These variants enable more efficient targeting of sites in human cells; the variants can also be used in other experiments and contexts (e.g. in other cell types, in various organisms, for in vivo editing, for in vitro experiments, for molecular biology, for nucleic acid detection, for other non-nuclease applications (base editing, prime editing, epigenetic editing, etc.), etc. This strategy can be applied to other CRISPR-Cas proteins, including other Cas9 orthologs with various levels of basal activity (SaCas9, St1Cas9, St3Cas9, NmeCas9, Nme2Cas9, CjeCas9, etc.), Cas12a orthologs, and other Cas3, Cas12, Cas13, and Cas14 proteins. More generally, this strategy can be applied to other nucleic acid-binding proteins (zinc-fingers and zinc-finger nucleases (ZFs and ZFNs), transcription activator-like effectors and transcription activator-like effector nucleases (TALEs and TALENs), restriction enzymes, transposases, recombinases, integrases, etc. Thus described herein are methods to enhance the activities of nucleic-acid binding proteins; the present disclosure demonstrates the effectiveness of this strategy for improving on-target editing of CRISPR-Cas nucleases.

All of the SpCas9 variants described herein can be rapidly incorporated into existing and widely used vectors, e.g., by simple site-directed mutagenesis, and can also be combined with other previously described improvements to the SpCas9 platform (e.g., truncated sgRNAs (Tsai et al., Nat Biotechnol 33, 187-197 (2015); Fu et al., Nat Biotechnol 32, 279-284 (2014)), nickase mutations (Mali et al., Nat Biotechnol 31, 833-838 (2013); Ran et al., Cell 154, 1380-1389 (2013)), dimeric FokI-dCas9 fusions (Guilinger et al., Nat Biotechnol 32, 577-582 (2014); Tsai et al., Nat Biotechnol 32, 569-576 (2014)); and high-fidelity variants (Kleinstiver et al. Nature 2016).

SpCas9 Variants

Thus, provided herein are SpCas9 variants. The SpCas9 wild type sequence is as follows:

```
SpCas9 variants
Thus, provided herein are SpCas9 variants. The
SpCas9 wild type sequence is as follows:
                                            (SEQ ID NO: 1)
         10          20          30          40
MDKKYSIGLD  IGTNSVGWAV  ITDEYKVPSK  KFKVLGNTDR 50          60          70          80
HSIKKNLIGA  LLFDSGETAE  ATRLKRTARR  RYTRRKNRIC 90         100         110         120
YLQEIFSNEM  AKVDDSFFHR  LEESFLVEED  KKHERHPIFG 130         140         150         160
NIVDEVAYHE  KYPTIYHLRK  KLVDSTDKAD  LRLIYLALAH 170         180         190         200
MIKFRGHFLI  EGDLNPDNSD  VDKLFIQLVQ  TYNQLFEENP 210         220         230         240
INASGVDAKA  ILSARLSKSR  RLENLIAQLP  GEKKNGLFGN
```

```
-continued
        250         260         270         280
LIALSLGLTP  NFKSNFDLAE  DAKLQLSKDT  YDDDLDNLLA 290         300         310         320
QIGDQYADLF  LAAKNLSDAI  LLSDILRVNT  EITKAPLSAS 330         340         350         360
MIKRYDEHHQ  DLTLLKALVR  QQLPEKYKEI  FFDQSKNGYA 370         380         390         400
GYIDGGASQE  EFYKFIKPIL  EKMDGTEELL  VKLNREDLLR 410         420         430         440
KQRTFDNGSI  PHQIHLGELH  AILRRQEDFY  PFLKDNREKI 450         460         470         480
EKILTFRIPY  YVGPLARGNS  RFAWMTRKSE  ETITPWNFEE 490         500         510         520
VVDKGASAQS  FIERMTNFDK  NLPNEKVLPK  HSLLYEYFTV 530         540         550         560
YNELTKVKYV  TEGMRKPAFL  SGEQKKAIVD  LLFKTNRKVT 570         580         590         600
VKQLKEDYFK  KIECFDSVEI  SGVEDRFNAS  LGTYHDLLKI 610         620         630         640
IKDKDFLDNE  ENEDILEDIV  LTLTLFEDRE  MIEERLKTYA 650         660         670         680
HLFDDKVMKQ  LKRRRYTGWG  RLSRKLINGI  RDKQSGKTIL 690         700         710         720
DFLKSDGFAN  RNFMQLIHDD  SLTFKEDIQK  AQVSGQGDSL 730         740         750         760
HEHIANLAGS  PAIKKGILQT  VKVVDELVKV  MGRHKPENIV 770         780         790         800
IEMARENQTT  QKGQKNSRER  MKRIEEGIKE  LGSQILKEHP 810         820         830         840
VENTQLQNEK  LYLYYLQNGR  DMYVDQELDI  NRLSDYDVDH 850         860         870         880
IVPQSFLKDD  SIDNKVLTRS  DKNRGKSDNV  PSEEVVKKMK 890         900         910         920
NYWRQLLNAK  LITQRKFDNL  TKAERGGLSE  LDKAGFIKRQ 930         940         950         960
LVETRQITKH  VAQILDSRMN  TKYDENDKLI  REVKVITLKS 970         980         990        1000
KLVSDFRKDF  QFYKVREINN  YHHAHDAYLN  AVVGTALIKK 1010        1020        1030        1040
YPKLESEFVY  GDYKVYDVRK  MIAKSEQEIG  KATAKYFFYS 1050        1060        1070        1080
NIMNFFKTEI  TLANGEIRKR  PLIETNGETG  EIVWDKGRDF 1090        1100        1110        1120
ATVRKVLSMP  QVNIVKKTEV  QTGGFSKESI  LPKRNSDKLI 1130        1140        1150        1160
ARKKDWDPKK  YGGFDSPTVA  YSVLVVAKVE  KGKSKKLKSV 1170        1180        1190        1200
KELLGITIME  RSSFEKNPID  FLEAKGYKEV  KKDLIIKLPK 1210        1220        1230        1240
YSLFELENGR  KRMLASAGEL  QKGNELALPS  KYVNFLYLAS 1250        1260        1270        1280
HYEKLKGSPE  DNEQKQLFVE  QHKHYLDEII  EQISEFSKRV 1290        1300        1310        1320
ILADANLDKV  LSAYNKHRDK  PIREQAENII  HLFTLTNLGA
```

```
               -continued
       1330       1340       1350       1360
   PAAFKYFDTT IDRKRYTSTK EVLDATLIHQ SITGLYETRI

DLSQLGGD
```

The SpCas9 variants described herein can include mutations at one two, three, four, five, or more of the positions shown in Table 1. For example, mutations at one or more of G1104X, e.g., G1104K or G1104R; A61X, e.g., A61R; N1317X, e.g., N1317R; S55X, e.g., S55R; T1314X, e.g., T1314R; G366X, e.g., G366R; A1285X, e.g., A1285R or A1285K; D1332X, e.g., D1332R or D1332H or D1332Q or D1332N; K1151X, e.g., K1151R; T1138X, e.g., T1138K or T1138R; V1139X, e.g., V1139T; K1289X, e.g., K1289R; A1322X, e.g., A1322K; and/or L1111X, e.g., L1111K, or at positions analogous thereto in an analogous protein; where X is any amino acid, e.g., any amino acid shown in Table 1 as a "exemplary substitution". In some embodiments, the SpCas9 variants are at least 80%, e.g., at least 85%, 90%, or 95% identical to the amino acid sequence of SEQ ID NO:1, e.g., have differences at up to 5%, 10%, 15%, or 20% of the residues of SEQ ID NO:1 replaced, e.g., with conservative mutations. In preferred embodiments, the variant retains desired activity of the parent, e.g., the nuclease activity (except where the parent is a nickase or a dead Cas9), and/or the ability to interact with a guide RNA and target DNA).

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed, pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). For purposes of the present compositions and methods, at least 80% of the full length of the sequence is aligned to using the BLAST algorithm and the default parameters.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. Some exemplary mutations are shown in Table 1, which appears below in the Examples.

In some embodiments, the SpCas9 variant is a variant with one or more mutations as shown in Table 2.

TABLE 2

| Rank | Substitution |
|---|---|
| 1 | G1104K |
| 2 | A61R |
| 3 | N1317R |
| 4 | S55R |
| 5 | T1314R |
| 6 | G1104R |
| 7 | G366R |
| 8 | A1285R |
| 9 | A1285K |
| 10 | D1332R |
| 11 | K1151R |
| 12 | T1138K |
| 13 | T1138R |
| 14 | V1139T |
| 15 | D1332H |
| 16 | D1332Q |
| 17 | D1332N |
| 18 | K1289R |
| 19 | A1322K |
| 20 | L1111K |

In some embodiments, the SpCas9 variant also includes one or more mutations shown in Table 3.

TABLE 3

| Rank | Substitution rank |
|---|---|
| 1 | G1218R |
| 2 | L1111R |
| 3 | A1322R |
| 4 | D1332K |
| 5 | N394K |
| 6 | R221K |
| 7 | L1245V |
| 8 | E1243K |
| 9 | E1253K |

In some embodiments, the SpCas9 variants also include mutations at one of the following amino acid positions, which reduce or destroy the nuclease activity of the Cas9: D10, E762, D839, H983, or D986 and H840 or N863, e.g., D10A/D10N and H840A/H840N/H840Y, to render the nuclease portion of the protein catalytically inactive; substitutions at these positions could be alanine (as they are in Nishimasu al., Cell 156, 935-949 (2014)), or other residues, e.g., glutamine, asparagine, tyrosine, serine, or aspartate, e.g., E762Q, H983N, H983Y, D986N, N863D, N863S, or N863H (see WO 2014/152432). In some embodiments, the variant includes mutations at D10A or H840A (which creates a single-strand nickase), or mutations at D10A and H840A (which abrogates nuclease activity; this mutant is known as dead Cas9 or dCas9).

In some embodiments, the SpCas9 variants also include mutations at one or more amino acid positions that increase the specificity of the protein (i.e., reduce off-target effects). In some embodiments, the SpCas9 variants include one, two, three, four, five, six, seven, eight, nine, ten, or all eleven of the following mutations: N497A, R661A, N692A, M694A, Q695A, H698A, K810A, K848A, Q926A, K1003A, and/or R1060A.

In some embodiments, the SpCas9 variants include mutations at one, two, three, four, five, six or all seven of the following positions: L169A, Y450, N497, R661, Q695, Q926, and/or D1135E, e.g., in some embodiments, the variant SpCas9 proteins comprise mutations at one, two, three, or all four of the following: N497, R661, Q695, and Q926, e.g., one, two, three, or all four of the following mutations: N497A, R661A, Q695A, and Q926A. In some embodiments, the variant SpCas9 proteins comprise mutations at Q695 and/or Q926, and optionally one, two, three, four or all five of L169, Y450, N497, R661 and D1135E, e.g., including but not limited to Y450A/Q695A, L169A/Q695A, Q695A/Q926A, Q695A/D1135E, Q926A/D1135E, Y450A/D1135E, L169A/Y450A/Q695A, L169A/Q695A/Q926A, Y450A/Q695A/Q926A, R661A/Q695A/Q926A, N497A/Q695A/Q926A, Y450A/Q695A/D1135E, Y450A/Q926A/D1135E, Q695A/Q926A/D1135E, L169A/Y450A/Q695A/Q926A, L169A/R661A/Q695A/Q926A, Y450A/R661A/Q695A/Q926A, N497A/Q695A/Q926A/D1135E, R661A/Q695A/Q926A/D1135E, and Y450A/Q695A/Q926A/D1135E. See, e.g., Kleinstiver et al., Nature 529: 490-495 (2016); WO 2017/040348; U.S. Pat. No. 9,512,446).

In some embodiments, the SpCas9 variants also include mutations at one, two, three, four, five, six, seven, or more of the following positions: F491, M495, T496, N497, G582, V583, E584, D585, N588, T657, G658, W659, R661, N692, M694, Q695, H698, K918, V922, and/or R925, and optionally at Q926, preferably comprising a sequence that is at least 80% identical to the amino acid sequence of SEQ ID NO:1 with mutations at one, two, three, four, five, six, seven, or more of the following positions: F491, M495, T496, N497, G582, V583, E584, D585, N588, T657, G658, W659, R661, N692, M694, Q695, H698, K918, V922, and/or R925, and optionally at Q926.

In some embodiments, the SpCas9 variants include one or more of a nuclear localization sequence, cell penetrating peptide sequence, and/or affinity tag.

In some embodiments, the proteins comprise mutations at one, two, three, or all four of the following: N692, M694, Q695, and H698; G582, V583, E584, D585, and N588; T657, G658, W659, and R661; F491, M495, T496, and N497; or K918, V922, R925, and Q926.

In some embodiments, the proteins comprise one, two, three, four, or all of the following mutations: N692A, M694A, Q695A, and H698A; G582A, V583A, E584A, D585A, and N588A; T657A, G658A, W659A, and R661A; F491A, M495A, T496A, and N497A; or K918A, V922A, R925A, and Q926A.

In some embodiments, the proteins comprise mutations: N692A/M694A/Q695A/H698A.

In some embodiments, the proteins comprise mutations: N692A/M694A/Q695A/H698A/Q926A; N692A/M694A/Q695A/Q926A; N692A/M694A/H698A/Q926A; N692A/Q695A/H698A/Q926A; M694A/Q695A/H698A/Q926A; N692A/Q695A/H698A; N692A/M694A/Q695A; N692A/M694A/H698A; N692A/M694A/Q926A; N692A/M694A/H698A; M694A/Q695A/H698A; M694A/Q695A/Q926A; Q695A/H698A/Q926A; G582A/V583A/E584A/D585A/N588A/Q926A; G582A/V583A/E584A/D585A/N588A; T657A/G658A/W659A/R661A/Q926A; T657A/G658A/W659A/R661A; F491A/M495A/T496A/N497A/Q926A; F491A/M495A/T496A/N497A; K918A/V922A/R925A/Q926A; or 918A/V922A/R925A. See, e.g., Chen et al., "Enhanced proofreading governs CRISPR-Cas9 targeting accuracy," bioRxiv, doi.org/10.1101/160036 (Aug. 12, 2017) and Nature, 550 (7676):407-410 (Oct. 19, 2017).

In some embodiments, the variant proteins include mutations at one or more of R780, K810, R832, K848, K855, K968, R976, H982, K1003, K1014, K1047, and/or R1060, e.g., R780A, K810A, R832A, K848A, K855A, K968A, R976A, H982A, K1003A, K1014A, K1047A, and/or R1060A, e.g., K855A; K810A/K1003A/R1060A; (also referred to as eSpCas9 1.0); or K848A/K1003A/R1060A (also referred to as eSpCas9 1.1) (see Slaymaker et al., Science. 2016 Jan. 1; 351(6268):84-8).

In some embodiments, the variant proteins include mutations at R691, e.g. R691A. See, e.g. Vakulskas et al., Nat Med. 2018 August; 24(8): 1216-1224.

In some embodiments, the variant proteins include mutations at one or more of M495, Y515, K526, and R661, e.g., M495V, Y515N, K526E, R661Q, R661L, and/or R661S, e.g. M495V/Y515N/K526E/R661Q; M495V/Y515N/K526E/R661L; or M495V/Y515N/K526E/R661S. See, e.g. Casini et al., Nat Biotechnol. 2018 March; 36(3): 265-271.

Also provided herein are isolated nucleic acids encoding the SpCas9 variants, vectors comprising the isolated nucleic acids, optionally operably linked to one or more regulatory domains for expressing the variant proteins, and host cells, e.g., mammalian host cells, comprising the nucleic acids, and optionally expressing the variant proteins.

The variant proteins described herein can be used in place of the SpCas9 proteins described in the foregoing references with guide RNAs that target sequences that have PAM sequences according to Tables 1,2, or 3.

In addition, the variants described herein can be used in fusion proteins in place of the wild-type Cas9 or other Cas9 mutations (such as the dCas9 or Cas9 nickase described above) as known in the art, e.g., a fusion protein with a heterologous functional domain, e.g., as described in WO 2014/124284. In some embodiments, the heterologous functional domain has a DNA-modifying activity. For example, the variants, preferably comprising one or more nuclease-reducing or killing mutation, can be fused on the N or C terminus of the Cas9 to a transcriptional activation domain or other heterologous functional domains (e.g., transcriptional repressors (e.g., KRAB, ERD, SID, and others, e.g., amino acids 473-530 of the ets2 repressor factor (ERF) repressor domain (ERD), amino acids 1-97 of the KRAB domain of KOX1, or amino acids 1-36 of the Mad mSIN3 interaction domain (SID); see Beerli et al., PNAS USA 95:14628-14633 (1998)) or silencers such as Heterochromatin Protein 1 (HP1, also known as swi6), e.g., HP1α or HP1β; proteins or peptides that could recruit long non-coding RNAs (lncRNAs) fused to a fixed RNA binding sequence such as those bound by the MS2 coat protein, endoribonuclease Csy4, or the lambda N protein; enzymes that modify the methylation state of DNA (e.g., DNA methyltransferase (DNMT) or TET proteins); enzymes that modify histone subunits (e.g., histone acetyltransferases (HAT), histone deacetylases (HDAC), histone methyltransferases (e.g., for methylation of lysine or arginine residues) or histone demethylases (e.g., for demethylation of lysine or arginine residues)) (see, e.g., Komor et al., Nature. 2016 May 19; 533(7603):420-4; Nishida et al., Science. 2016 Sep. 16; 353(6305). pii: aaf8729; Rees et al., Nat Commun. 2017

Jun. 6; 8:15790; or Kim et al., Nat Biotechnol. 2017 April; 35(4):371-376) as are known in the art can also be used. A number of sequences for such domains are known in the art, e.g., a domain that catalyzes hydroxylation of methylated cytosines in DNA. Exemplary proteins include the Ten-Eleven-Translocation (TET) 1-3 family, enzymes that converts 5-methylcytosine (5-mC) to 5-hydroxymethylcytosine (5-hmC) in DNA.

Sequences for human TET1-3 are known in the art and are shown in the following table:

| Gene | GenBank Accession Nos. | |
|------|-------------|-------------|
|      | Amino Acid  | Nucleic Acid |
| TET1 | NP_085128.2 | NM_030625.2 |
| TET2* | NP_001120680.1 (var 1) | NM_001127208.2 |
|      | NP_060098.3 (var 2) | NM_017628.4 |
| TET3 | NP_659430.1 | NM_144993.1 |

In some embodiments, all or part of the full-length sequence of the catalytic domain can be included, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. See, e.g., FIG. 1 of Iyer et al., Cell Cycle. 2009 Jun. 1; 8(11):1698-710. Epub 2009 Jun. 27, for an alignment illustrating the key catalytic residues in all three Tet proteins, and the supplementary materials thereof for full length sequences (see, e.g., seq 2c); in some embodiments, the sequence includes amino acids 1418-2136 of Tet1 or the corresponding region in Tet2/3.

Other catalytic modules can be from the proteins identified in Iyer et al., 2009.

In some embodiments, the heterologous functional domain is a biological tether, and comprises all or part of (e.g., DNA binding domain from) the MS2 coat protein, endoribonuclease Csy4, or the lambda N protein. These proteins can be used to recruit RNA molecules containing a specific stem-loop structure to a locale specified by the dCas9 gRNA targeting sequences. For example, a dCas9 variant fused to MS2 coat protein, endoribonuclease Csy4, or lambda N can be used to recruit a long non-coding RNA (lncRNA) such as XIST or HOTAIR; see, e.g., Keryer-Bibens et al., Biol. Cell 100:125-138 (2008), that is linked to the Csy4, MS2 or lambda N binding sequence. Alternatively, the Csy4, MS2 or lambda N protein binding sequence can be linked to another protein, e.g., as described in Keryer-Bibens et al., supra, and the protein can be targeted to the dCas9 variant binding site using the methods and compositions described herein. In some embodiments, the Csy4 is catalytically inactive. In some embodiments, the Cas9 variant, preferably a dCas9 variant, is fused to FokI as described in WO 2014/204578.

In some embodiments, the heterologous functional domain comprises a base editor, e.g., a cytidine deaminase domain, e.g., from the apolipoprotein B mRNA-editing enzyme, catalytic polypeptide-like (APOBEC) family of deaminases, including APOBEC1, APOBEC2, APOBEC3A, APOBEC3B, APOBEC3C, APOBEC3D/E, APOBEC3F, APOBEC3G, APOBEC3H, or APOBEC4; activation-induced cytidine deaminase (AID), e.g., activation induced cytidine deaminase (AICDA); cytosine deaminase 1 (CDA1) or CDA2; or cytosine deaminase acting on tRNA (CDAT). In some embodiments, the heterologous functional domain is a deaminase that modifies adenosine DNA bases, e.g., the deaminase is an adenosine deaminase 1 (ADA1), ADA2; adenosine deaminase acting on RNA 1 (ADAR1), ADAR2, ADAR3; adenosine deaminase acting on tRNA 1 (ADAT1), ADAT2, ADAT3; and naturally occurring or engineered tRNA-specific adenosine deaminase (TadA). Such proteins comprising a base editing domain include cytosine or adenine base editors (CBEs or ABEs), or variants thereof with reduced RNA editing activity, e.g., the SElective Curbing of Unwanted RNA Editing (SECURE)-BE3 variants and SECURE-ABE variants. See, e.g., Gaudelli et al., Nature 551, 464-471 (2017). Grünewald et al., Nature. 2019 May; 569(7756):433-437; Grünewald et al., bioRxiv 631721; doi.org/10.1101/631721; et al., Nat Grünewald Biotechnol. 2019 September; 37(9):1041-1048; Abudayyeh et al., Science. 2019 Jul. 26; 365(6451):382-386; and Gehrke et al., Nat Biotechnol. 2018 November; 36(10):977-982.

In some embodiments, the base editing domain is an adenosine deaminase domain, e.g., a wild type and/or engineered adenosine deaminase TadA monomer or dimer (e.g., homodimeric or heterodimeric TadA domains from ABEmax, ABE7.10, or ABE8e; other options include monomer or dimer TadAs from ABEs 0.1, 0.2, 1.1, 1.2, 2.1, 2.2, 2.3, 2.4, 2.5, 2.6, 2.7, 2.8, 2.9, 2.10, 2.11, 2.12, 3.1, 3.2, 3.3, 3.4, 3.5, 3.6, 3.7, 3.8, 4.1, 4.2, 4.3, 5.1, 5.2, 5.3, 5.4, 5.5, 5.6, 5.7, 5.8, 5.9, 5.10, 5.11, 5.12, 5.13, 5.14, 6.1, 6.2, 6.3, 6.4, 6.5, 6.6, 7.1, 7.2, 7.3, 7.4, 7.5, 7.6, 7.7, 7.8, 7.9, 7.10, or ABEmax, or ABE8.8, ABE8.13, ABE8.17, ABE8.20, ABE8e—as well as K20A/R21A, V82G, or V106W variants thereof), $E.\ coli$ TadA monomer, or homo- or heterodimers thereof fused to the N or C terminus, bearing one or more mutations in either or both monomers (e.g., the TadA mutant used in miniABEmax-V82G, miniABEmax-K20A/R21A, miniABEmax-V106W or any other variant thereof, that decrease RNA editing activity while preserving DNA editing activity; see, e.g., Grünewald et al., Nature Biotechnology volume 38, pages 861-864(2020) and references cited therein.

In some embodiments, the heterologous functional domain is an enzyme, domain, or peptide that inhibits or enhances endogenous DNA repair or base excision repair (BER) pathways, e.g., uracil DNA glycosylase inhibitor (UGI) that inhibits uracil DNA glycosylase (UDG, also known as uracil N-glycosylase, or UNG) mediated excision of uracil to initiate BER; or DNA end-binding proteins such as Gam from the bacteriophage Mu.

In some embodiments, the heterologous functional domain is a prime editor, e.g., a reverse-transcriptase (RT) domain (e.g., Moloney murine leukaemia virus (M-MLV) RT or other RT enzyme), e.g., fused to a Cas9 nickase. In such embodiments, the variant is used in conjunction with a prime editing guide RNA (pegRNA) that both specifies the target site and encodes the desired edit. See, e.g., Anzalone et al., Nature December 2019; 576(7785):149-157.

In some embodiments, the fusion proteins include a linker between the dCas9 variant and the heterologous functional domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:2) or GGGGS (SEQ ID NO:3), e.g., two, three, four, or more repeats of the GGGS (SEQ ID NO:2) or GGGGS (SEQ ID NO:3) unit. Other linker sequences can also be used.

Methods of Use

The variants described herein have a number of uses; for example, they can be used for altering the genome of a cell; the methods generally include expressing the variant proteins in the cells, along with a guide RNA having a region complementary to a selected portion of the genome of the cell. Alternatively or in addition, they can be used to alter dsDNA in vitro, e.g., acting on DNA in a tube; for example, the SpRY variant described herein can be used is as a 'PAMless' restriction enzyme, to DNA anywhere, e.g., in a cell or in vitro reaction/test tube.

Methods for using CRISPR to selectively alter dsDNA, including altering the genome of a cell, are known in the art, see, e.g., U.S. Pat. No. 8,697,359; US2010/0076057; US2011/0189776; US2011/0223638; US2013/0130248; WO/2008/108989; WO/2010/054108; WO/2012/164565; WO/2013/098244; WO/2013/176772; US20150050699; US20150045546; US20150031134; US20150024500; US20140377868; US20140357530; US20140349400; US20140335620; US20140335063; US20140315985; US20140310830; US20140310828; US20140309487; US20140304853; US20140298547; US20140295556; US20140294773; US20140287938; US20140273234; US20140273232; US20140273231; US20140273230; US20140271987; US20140256046; US20140248702; US20140242702; US20140242700; US20140242699; US20140242664; US20140234972; US20140227787; US20140212869; US20140201857; US20140199767; US20140189896; US20140186958; US20140186919; US20140186843; US20140179770; US20140179006; US20140170753; Makarova et al., "Evolution and classification of the CRISPR-Cas systems" 9(6) Nature Reviews Microbiology 467-477 (1-23) (June 2011); Wiedenheft et al., "RNA-guided genetic silencing systems in bacteria and archaea" 482 Nature 331-338 (Feb. 16, 2012); Gasiunas et al., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012); Jinek et al., "A Programmable Dual-RNA-Guided DNA Endonuclease in Adaptive Bacterial Immunity" 337 Science 816-821 (Aug. 17, 2012); Carroll, "A CRISPR Approach to Gene Targeting" 20(9) Molecular Therapy 1658-1660 (September 2012); U.S. Appl. No. 61/652,086, filed May 25, 2012; Al-Attar et al., Clustered Regularly Interspaced Short Palindromic Repeats (CRISPRs): The Hallmark of an Ingenious Antiviral Defense Mechanism in Prokaryotes, Biol Chem. (2011) vol. 392, Issue 4, pp. 277-289; Hale et al., Essential Features and Rational Design of CRISPR RNAs That Function With the Cas RAMP Module Complex to Cleave RNAs, Molecular Cell, (2012) vol. 45, Issue 3, 292-302.

Delivery and Expression Systems

To use the Cas9 variants described herein, it may be desirable to express them from a nucleic acid that encodes them. This can be performed in a variety of ways. For example, the nucleic acid encoding the Cas9 variant can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the Cas9 variant for production of the Cas9 variant. The nucleic acid encoding the Cas9 variant can also be cloned into an expression vector, for administration to a plant cell, animal cell, preferably a mammalian cell or a human cell, fungal cell, bacterial cell, or protozoan cell.

To obtain expression, a sequence encoding a Cas9 variant is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of a nucleic acid depends on the particular application. For example, a strong constitutive promoter is typically used for expression and purification of fusion proteins. In contrast, when the Cas9 variant is to be administered in vivo for gene regulation, either a constitutive or an inducible promoter can be used, depending on the particular use of the Cas9 variant. In addition, a preferred promoter for administration of the Cas9 variant can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the Cas9 variant, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the Cas9 variant, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the Cas9 variants can include RNA Pol III promoters to drive expression of the guide RNAs, e.g., the H1, U6 or 7SK promoters. These human promoters allow for expression of Cas9 variants in mammalian cells following plasmid transfection.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the gRNA encoding sequence under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the Cas9 variant.

Alternatively, the methods can include delivering the Cas9 variant protein and guide RNA together, e.g., as a complex. For example, the Cas9 variant and gRNA can be can be overexpressed in a host cell and purified, then complexed with the guide RNA (e.g., in a test tube) to form a ribonucleoprotein (RNP), and delivered to cells. In some embodiments, the variant Cas9 can be expressed in and purified from bacteria through the use of bacterial Cas9 expression plasmids. For example, His-tagged variant Cas9 proteins can be expressed in bacterial cells and then purified using nickel affinity chromatography. The use of RNPs circumvents the necessity of delivering plasmid DNAs encoding the nuclease or the guide, or encoding the nuclease as an mRNA. RNP delivery may also improve specificity, presumably because the half-life of the RNP is shorter and there's no persistent expression of the nuclease and guide (as you'd get from a plasmid). The RNPs can be delivered to the cells in vivo or in vitro, e.g., using lipid-mediated transfection or electroporation. See, e.g., Liang et al. "Rapid and highly efficient mammalian cell engineering via Cas9 protein transfection." Journal of biotechnology 208 (2015): 44-53; Zuris, John A., et al. "Cationic lipid-mediated delivery of proteins enables efficient protein-based genome editing in vitro and in vivo." Nature biotechnology 33.1 (2015): 73-80; Kim et al. "Highly efficient RNA-guided genome editing in human cells via delivery of purified Cas9 ribonucleoproteins." Genome research 24.6 (2014): 1012-1019.

The present invention includes the vectors and cells comprising the vectors.

EXAMPLES

The invention is further described in the following examples, which do not limit the scope of the invention described in the claims.

Methods

The following materials and methods were used in the Examples below.

Plasmids and Oligonucleotides

The SpCas9 nuclease human expression plasmid was generated by subcloning the SpCas9 open reading frame from pX330 (Addgene plasmid 42230; a gift from Feng Zhang) into the NotI and AgeI sites of JDS246 (Addgene plasmid 43861). Nuclease constructs harboring a C-terminal BP(SV40)NLS-3×FLAG-P2A-EGFP sequence were utilized for all human cell experiments. All modifications to plasmids, including generation of point mutations and the addition of P2A-EGFP, were generated through standard molecular cloning and isothermal assembly. Human cell expression plasmids for U6 promoter-driven SpCas9 sgRNAs were generated by annealing and ligating duplexed oligonucleotides corresponding to spacer sequences into BsmBI-digested BPK1520 (ref[8]). Plasmids for in vitro transcription of SpCas9 sgRNAs were generated by annealing and ligating oligonucleotides corresponding to spacer sequence duplexes into BsaI-digested MSP3485 for T7 promoter-driven transcription of sgRNAs.

Plasmid libraries with 8 nt randomized PAM sequences on the 3' end of the target sites were generated from two oligonucleotides encoding separate spacer sequences, similar to as previously described[14]. Briefly, Klenow(−exo) (NEB) was used to generate the bottom strand of the dsDNA sequence, and the product was digested with EcoRI prior to ligation into EcoRI and SphI digested p11-lacY-wtx1 (Addgene plasmid 69056; a gift from Huimin Zhao). Ligated plasmids were transformed into electrocompetent XL1-Blue E. coli, recovered in 9 ml of super optimal broth with catabolite repression (SOC) at 37° C. for approximately 60 minutes, and then grown for 16 hours in 150 mL of Luria-Bertani (LB) medium with 100 µg/mL carbenicillin. The complexity of each library was estimated to be greater than $10^5$ unique PAMs based on the number of transformants. Plasmid libraries were linearized with PvuI (NEB) prior to use in the in vitro cleavage reactions.

Structural Modeling of SpCas9

The crystal structure of WT SpCas9 (PDB:4UN3)[15] was visualized using PyMOL version 2.3.3.

Human Cell Culture

Human HEK 293T cells (ATCC) were cultured in Dulbecco's Modified Eagle Medium (DMEM) supplemented with 10% heat-inactivated FBS (HI-FBS) and 1% penicillin/streptomycin. The supernatant media from cell cultures was analyzed monthly for the presence of *mycoplasma* using MycoAlert PLUS (Lonza).

Transfection of Human Cells

All experiments were performed with at least 3 independent biological replicates. For all human cell experiments, transfections were performed between 20 and 24 hours following seeding of $2 \times 10^4$ HEK 293T cells per well in 96-well plates. For nuclease experiments, 29 ng of nuclease and 12.5 ng of sgRNA expression plasmids (unless otherwise indicated) were mixed with 0.3 µl of TransIT-X2

(Mirus) in a total volume of 15 µL Opti-MEM (Thermo Fisher Scientific), incubated for 15 minutes at room temperature, and added to HEK 293T cells. Experiments were halted after 72 hours. Genomic DNA was collected by discarding the media, resuspending the cells in 100 µL of quick lysis buffer (20 mM Hepes pH 7.5, 100 mM KCl, 5 mM $MgCl_2$, 5% glycerol, 25 mM DTT, 0.1% Triton X-100, and 60 ng/ul Proteinase K (New England Biolabs; NEB)), heating the lysate for 6 minutes at 65° C., heating at 98° C. for 2 minutes, and then storing at −20° C.

Assessment of Nuclease Activities in Human Cells

The efficiency of genome modification was determined by next-generation sequencing using a 2-step PCR-based Illumina library construction method. Briefly, genomic loci were amplified from approximately 100 ng of genomic DNA using Q5 High-fidelity DNA Polymerase (NEB). PCR products were purified using paramagnetic beads prepared as previously described[14,19]. Approximately 20 ng of purified PCR product was used as template for a second PCR to add Illumina barcodes and adapter sequences using Q5 polymerase. PCR products were purified prior to quantification via capillary electrophoresis (Qiagen QIAxcel), normalization, and pooling. Final libraries were quantified by qPCR (Illumina Library qPCR Quantification Kit, KAPA Biosystems) and sequenced on a MiSeq sequencer using a 300-cycle v2 kit (Illumina). Genome editing activities were determined from the sequencing data using CRISPResso2[20] with the additional command: —min_reads_to_use_region 100.

In Vitro Transcription of sgRNAs

SpCas9 sgRNAs were in vitro transcribed at 37° C. for 16 hours from roughly 1 µg of HindIII linearized sgRNA T7-transcription plasmid template (cloned into MSP3485) using the T7 RiboMAX Express Large Scale RNA Production Kit (Promega). The DNA template was degraded by the addition of 1 µL RQ1 DNase at 37° C. for 15 minutes. sgRNAs were purified with the MEGAclear Transcription Clean-Up Kit (ThermoFisher) and refolded by heating to 90° C. for 5 minutes and then cooling to room temperature for 15 minutes.

Expression of SpCas9 Proteins in Human Cells and Normalization of Lysates

To generate SpCas9 and variant proteins from human cell lysates, approximately 20-24 hours prior to transfection $1.5\times10^5$ HEK 293T cells were seeded in 24-well plates. Transfections containing 500 ng of human codon optimized nuclease expression plasmid (with a -P2A-EGFP signal) and 1.5 µL TransIT-X2 were mixed in a total volume of 50 µL of Opti-MEM, incubated at room temperature for 15 minutes, and added to the cells. The lysate was harvested after 48 hours by discarding the media and resuspending the cells in 100 ul of gentle lysis buffer (1× SIGMAFAST Protease Inhibitor Cocktail, EDTA-Free (Millipore Sigma), 20 mM Hepes pH 7.5, 100 mM KCl, 5 mM $MgCl_2$, 5% glycerol, 1 mM DTT, and 0.1% Triton X-100). The amount of SpCas9 protein was approximated from the whole-cell lysate based on EGFP fluorescence. SpCas9 lysates were normalized to 150 nM Fluorescein (Sigma, based on a Fluorescein standard curve. Fluorescence was measured in 384-well plates on a DTX 880 Multimode Plate Reader (Beckman Coulter) with $\lambda_{ex}$=485 nm and $\lambda_{em}$=535 nm.

High-Throughput PAM Determination Assay

The high-throughput PAM determination assay (HT-PAMDA) was performed using linearized randomized PAM-containing plasmid substrates that were subject to in vitro cleavage reactions with SpCas9 and variant proteins. First, SpCas9 ribonucleoproteins (RNPs) were complexed by mixing 4.375 µL of normalized whole-cell lysate (150 nM Fluorescein) with 8.75 pmol of in vitro transcribed sgRNA and incubating for 5 minutes at 37° C. Cleavage reactions were initiated by the addition of 43.75 fmol of randomized-PAM plasmid library and buffer to bring the total reaction volume to 17.5 µL with a final composition of 10 mM Hepes pH 7.5, 150 mM NaCl, and 5 mM $MgCl_2$. Reactions were performed at 37° C. and aliquots were terminated at timepoints of 1, 8, and 32 minutes by removing 5 µL aliquots from the reaction and mixing with 5 µL of stop buffer (50 mM EDTA and 2 mg/ml Proteinase K (NEB)), incubating at room temperature for 10-minutes, and heat inactivating at 98° C. for 5 minutes. For all variants characterized, time courses were completed on both libraries harboring distinct spacer sequences for n=2; several variants were characterized with additional replicates to evaluate reproducibility of the assay, where for those variants the final data is an average of all replicates.

Next, approximately 3 ng of digested PAM library for each SpCas9 variant and reaction timepoint was PCR amplified using Q5 polymerase (NEB) and barcoded using unique combinations of i5 and i7 primers. PCR products were pooled for each time point, purified using paramagnetic beads, and prepared for sequencing using one of two library preparation methods. Pooled amplicons were prepared for sequencing using either (1) the KAPA HTP PCR-free Library Preparation Kit (KAPA BioSystems), or (2) a PCR-based method where pooled amplicons were treated with Exonuclease I, purified using paramagnetic beads, amplified using Q5 polymerase with approximately 250 pg of pooled amplicons at template, and again purified using paramagnetic beads. Libraries constructed via either method were quantified using the Universal KAPA Illumina Library qPCR Quantification Kit (KAPA Biosystems) and sequenced on a NextSeq sequencer using either a 150-cycle (method 1) or 75-cycle (method 2) NextSeq 500/550 High Output v2.5 kits (Illumina). Identical cleavage reactions prepared and sequenced via either library preparation method did not exhibit substantial differences.

Sequencing reads were analyzed using a custom Python script to determine cleavage rates for all SpCas9 nucleases on each substrate with unique spacers and PAMs, similar to as previously described[14]. Briefly, reads were assigned to specific SpCas9 variants based on based on custom pooling barcodes, assigned timepoints based on the combination of i5 and i7 primer barcodes, assigned to a plasmid library based on the spacer sequence, and assigned to a 3 (<ins>NNN</ins>N) or 4 (<ins>NNNN</ins>) nt PAM based on the identities of the DNA bases adjacent to the spacer sequence. Counts for all PAMs were computed for every SpCas9 variant, plasmid library, and timepoint, corrected for inter-sample differences in sequencing depth, converted to a fraction of the initial representation of that PAM in the original plasmid library (as determined by an untreated control), and then normalized to account for the increased fractional representation of uncut substrates over time due to depletion of cleaved substrates (by selecting the five PAMs with the highest average fractional representation across all time points to represent the profile of uncleavable substrates). The depletion of each PAM over time was then fit to an exponential decay model ($y(t)=Ae^{-kt}$, where y(t) is the normalized PAM count, t is the time (seconds), k is the rate constant, and A is a constant), by nonlinear regression. Reported rates are the average across both spacer sequences and across technical replicates when performed. Nonlinear least squares curve fitting was utilized to model SpCas9 cleavage, whereas linear least squares curve fitting was previously used for our Cas12a PAMDA assay[14].

Example 1. Assessment of Substitutions to Improve On-Target Editing with WT SpCas9 and SpCas9-VQR To determine whether the activities of CRISPR enzymes could be improved through rational engineering, we first began with a targeted mutagenesis screen of WT SpCas9. Using crystal structures of the SpCas9/gRNA/target DNA complex, we identified candidate amino acid residues for substitution in or near the PAM-interacting (PI) domain of SpCas9 whose alteration might form novel stabilizing contacts (Table 1).

TABLE 1

| position | Exemplary substitutions | priority | putative role for enhancing activity |
|---|---|---|---|
| G12 | R/K | 3 | NTS stabilization early in spacer |
| T13 | R/K | 2 | NTS stabilization early in spacer |
| N14 | R/K | 2 | NTS stabilization early in spacer |
| S15 | R/K | 2 | NTS stabilization early in spacer |
| L52 | R/K/H/Q/N | 2 | NTS stabilization early in spacer |
| D54 | R/K | 2 | NTS stabilization early in spacer or PAM |
| S55 | R/K | 1 | NTS stabilization early in spacer or PAM |
| A61 | R/K | 1 | TS stabilization early in spacer |
| L64 | R/K/H/Q/N/V/I/A/C/M/F/W | 1 | TS stabilization early in spacer |
| K65 | R/H | 1 | TS stabilization early in spacer |
| A68 | R/K/H/Q/N | 1 | TS stabilization early in spacer |
| D353 | R/K/H | 2 | PAM scanning, TS PAM stabilization |
| Q354 | R/K/H | 1 | PAM scanning, TS PAM stabilization |
| S355 | R/K/H | 1 | PAM scanning, TS PAM stabilization |
| K356 | R/H | 2 | PAM scanning, TS PAM stabilization |
| N357 | R/K/H | 2 | PAM scanning, TS PAM stabilization |
| G361 | R/K/H | 2 | PAM scanning, TS PAM stabilization |
| G365 | R/K/H | 2 | PAM scanning, TS PAM stabilization |
| G366 | R/K/H | 1 | PAM scanning, TS PAM stabilization |
| A367 | R/K/H | 2 | PAM scanning, TS PAM stabilization |
| S368 | R/K/H | 2 | PAM scanning, TS PAM stabilization |
| E371 | R/K/H | 2 | PAM scanning, TS PAM stabilization |
| N394 | R/K/H | 1 | unclear |
| E766 | R/K/H | 3 | NTS stabilization early in spacer |
| D839 | R/K/H | 3 | TS stabilization early in spacer |
| P843 | S/C/T/N | 1 | TS stabilization early in spacer |
| Q844 | S/C/T/N | 1 | TS stabilization early in spacer |
| S845 | R/K/H/Q/N | 1 | TS stabilization early in spacer |
| F846 | R/K/H/Q/N | 1 | NTS stabilization early in spacer |
| L847 | R/K/H/Q/N | 1 | NTS stabilization early in spacer |
| D861 | R/K/H/Q/N | 1 | TS stabilization early in spacer |
| K862 | R | 3 | TS stabilization early in spacer |
| R864 | K/H/Q/N | 1 | TS stabilization early in spacer |
| K866 | R/H/Q/N | 1 | TS stabilization early in spacer |
| D868 | R/K/H | 2 | PAM stabilization |
| R895 | K/H | 2 | NTS stabilization early in spacer |
| K902 | R/H | 2 | PAM stabilization |
| A903 | R/K/H | 2 | PAM stabilization |
| G906 | R/K/H/Q/N | 2 | NTS stabilization early in spacer |
| G907 | R/K/H/Q/N | 2 | NTS stabilization early in spacer |
| L908 | R/K/H/Q/N/S/C/T | 2 | NTS stabilization early in spacer |
| S909 | R/K/H/Q/N/C/T | 2 | NTS stabilization early in spacer |
| L911 | R/K/H | 3 | NTS stabilization early in spacer |
| K1096 | R/H | 3 | NTS stabilization early in spacer |
| G1104 | R/K/H | 1 | PAM stabilization |
| K1107 | R/S/H/Q/N/C/T | 1 | PAM stabilization |
| E1108 | R/K/H | 2 | TS stabilization early in spacer |
| S1109 | R/K/H/Q/N/C/T | 1 | PAM stabilization |
| L1111 | R/K/H | 1 | PAM stabilization |
| K1113 | R/K/H | 1 | PAM stabilization |
| R1114 | K/H | 1 | PAM stabilization |
| N1115 | R/K/H/Q/S/C/T | 1 | PAM stabilization |
| S1116 | R/K/H/Q/N/C/T | 1 | PAM stabilization |
| D1117 | R/K/H | 3 | PAM stabilization |
| K1118 | R/H/Q/N | 1 | PAM stabilization |
| K1129 | R/H | 3 | PAM stabilization |
| D1135 | R/K/H/Q/N/S/C/T | 1 | PAM stabilization |
| S1136 | R/K/H/Q/N/C/T | 1 | PAM stabilization |
| T1138 | R/K/H | 3 | PAM stabilization |
| V1139 | R/K/H/Q/N/S/C/T | 2 | PAM stabilization |
| V1149 | R/K/H | 3 | DNA duplex binding 3' of PAM |
| K1151 | R/H | 1 | DNA duplex binding 3' of PAM |
| G1152 | R/K/H | 2 | DNA duplex binding 3' of PAM |
| K1153 | R/H | 1 | DNA duplex binding 3' of PAM |
| S1154 | R/K/H | 1 | DNA duplex binding 3' of PAM |
| K1155 | R/H | 3 | DNA duplex binding 3' of PAM |
| K1156 | R/H | 3 | DNA duplex binding 3' of PAM |
| K1158 | R/H | 1 | DNA duplex binding 3' of PAM |
| E1162 | R/K/H | 3 | DNA duplex binding 3' of PAM |
| K1200 | R/H/Q/N/S/C/T | 1 | PAM stabilization |
| A1215 | R/K/H/Q/N/S/C/T | 2 | PAM stabilization |
| S1216 | R/K/H/Q/N/S/C/T | 2 | PAM stabilization |
| A1217 | R/K/H/Q/N/S/C/T | 2 | PAM stabilization |
| G1218 | R/K/H/Q/N/S/C/T | 1 | PAM stabilization |
| E1219 | R/K/H/Q/N/S/C/T | 1 | PAM stabilization |
| Q1221 | R/K/H/N/S/C/T | 2 | PAM stabilization |
| V1280 | R/K/H | 3 | PAM stabilization |
| I1281 | R/K/H | 3 | PAM stabilization |
| L1282 | R/K/H | 2 | PAM stabilization |
| A1283 | R/K/H/Q/N/S/C/T | 2 | PAM stabilization |
| A1285 | R/K/H/Q/N/S/C/T | 1 | PAM stabilization |
| N1286 | R/K/H/Q/S/C/T | 2 | PAM stabilization |
| K1289 | R/H | 1 | PAM stabilization |
| T1314 | R/K/H/Q/N/S/C | 2 | PAM stabilization |
| N1317 | R/K/H/Q/S/C/T | 1 | PAM stabilization |
| A1320 | R/K/H/Q/N/S/C/T | 1 | PAM stabilization |
| P1321 | R/K/H/Q/N/S/C/T | 2 | PAM stabilization |
| A1322 | R/K/H | 1 | PAM stabilization/NTS stabilization early in spacer |
| A1323 | R/K/H | 3 | PAM stabilization |
| T1330 | R/K/H | 3 | PAM stabilization |
| D1332 | R/K/H/Q/N/S/C/T | 1 | PAM stabilization |
| T1337 | R/K/H/Q/N/S/C | 1 | PAM stabilization |
| S1338 | R/K/H/Q/N/C/T | 1 | PAM stabilization |
| K1340 | R/K/H/Q/N/S/C/T | 2 | PAM stabilization |
| V1342 | R/K/H | 3 | PAM stabilization |
| D1368 | R/K/H | 3 | DNA duplex binding 3' of PAM |

It was hypothesized that mutations to positively charged or non-conservative residues might alter on-target editing by a variety of mechanisms, including, but not limited to: improving reaction kinetics of PAM search or target site recognition, enhancing the stability of Cas9-PAM interactions, introducing novel contacts to the target or non-target DNA backbone (within or near the PAM), altering conformations of the protein, etc. In initial experiments we tested substitutions at a small number of these positions, including a series of positive control substitutions previously shown to improve on-target editing, including R221K, N394K, L1245V, E1243K, E1253K in WT SpCas9 (from ref[12]), G1218R in SpCas9-VRQR (from refs[8,9]), L1111R and A1322R to generate SpCas9-NG (from ref[13]), and D1332K in SpCas9-QQR1 (from ref[11]). Note that N1286Q was also described in ref[11].

Figure 1B:
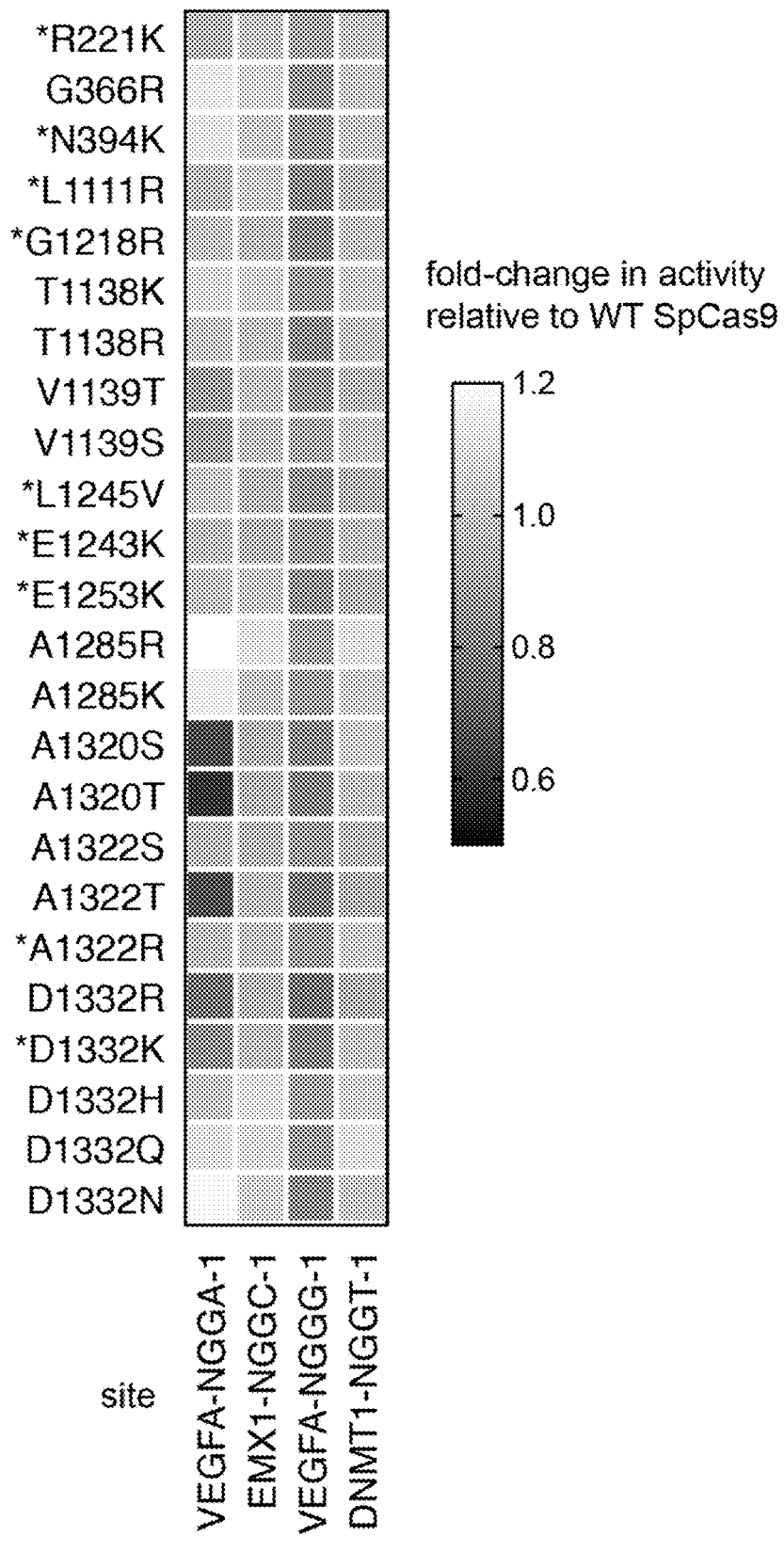

To determine whether these substitutions improve on-target editing, we generated SpCas9 expression constructs harboring these mutations and assessed their ability to target four sites in HEK 293T cells (FIG. 1A). We harvested genomic DNA after 72 hours, amplified each genomic locus using targeted amplicon sequencing, and determined what percentage of sequencing reads harbored nuclease-induced editing events. While the novel SpCas9-A1285R, -G366R, -T1138K, and D1332Q variants exhibited increased activity on 3 of 4 sites, in general, the fold-changes were minor and we observed mostly insignificant changes in on-target editing with other new or previously described substitutions (FIG. 1B). It is worth noting that 3 of 4 sites that we selected already exhibit high levels of editing, reducing the potential dynamic range to detect improvements in activity. Collectively, these results suggest that WT SpCas9 may be sufficiently energetically poised to edit the sites that we selected and might be refractory to this class of substitution, and that augmenting the activity of WT SpCas9 may require different substitutions, a combination of complementary substitutions, or alternative strategies.

Figure 2A:
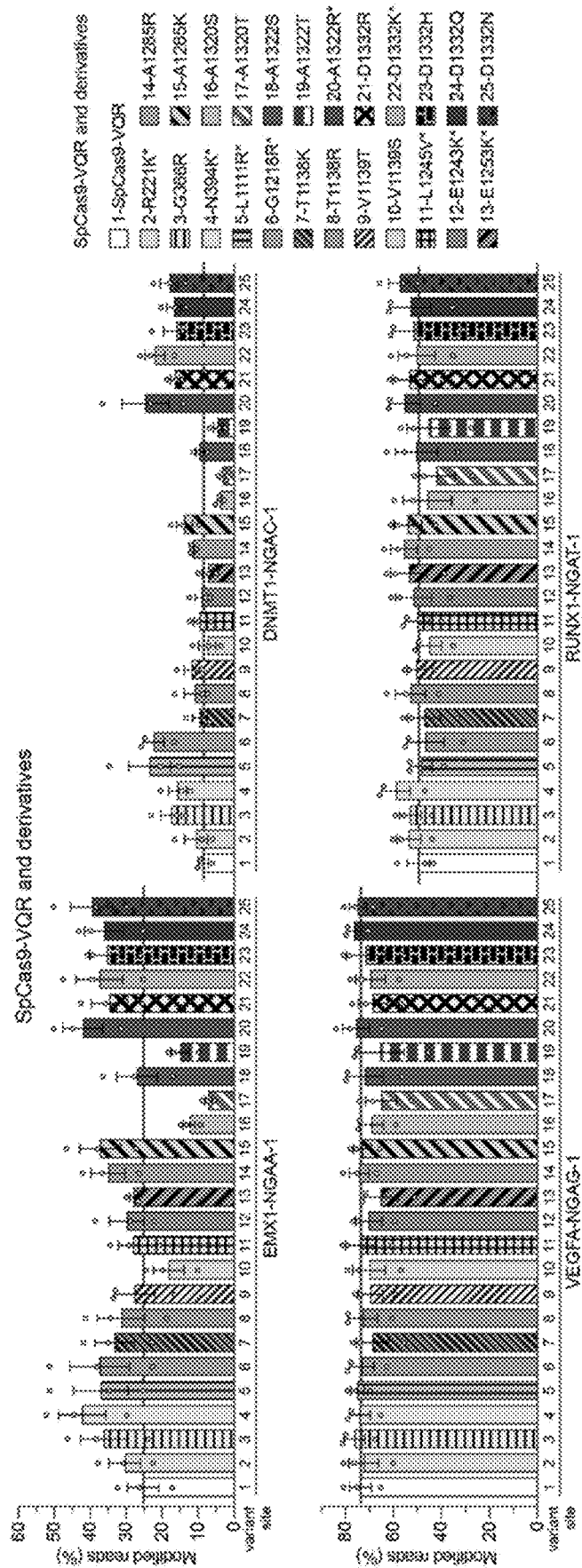
FIGS. 2A-B. Activities of SpCas9-VQR and variants bearing substitutions to improve on-target editing. A, Modification of endogenous sites in HEK 293T cells bearing NGA PAMs by SpCas9-VQR[8] and derivative variants encoding substitutions that putatively improve on-target editing. Percent modified reads assessed by targeted sequencing; mean, s.e.m., and individual data points shown for n=3; red line indicates mean modification with SpCas9-VQR. The symbol indicates variants previously described to improve on-target editing (R221K, N394K, L1245V, E1243K, E1253K in WT SpCas9 from ref[12]; G1218R in SpCas9-VRQR from refs[8,9]; L1111R and A1322R in SpCas9-NG from ref[13]; D1332K in SpCas9-QQR1 from ref[11]). B, quantification of the editing activities in panel A normalized to the levels of editing observed with SpCas9-VQR. The normalized activities of variants that improve on-target activity are shown in the blue, and the activities of variants that abrogate activity are shown in red.
Figure 2B:
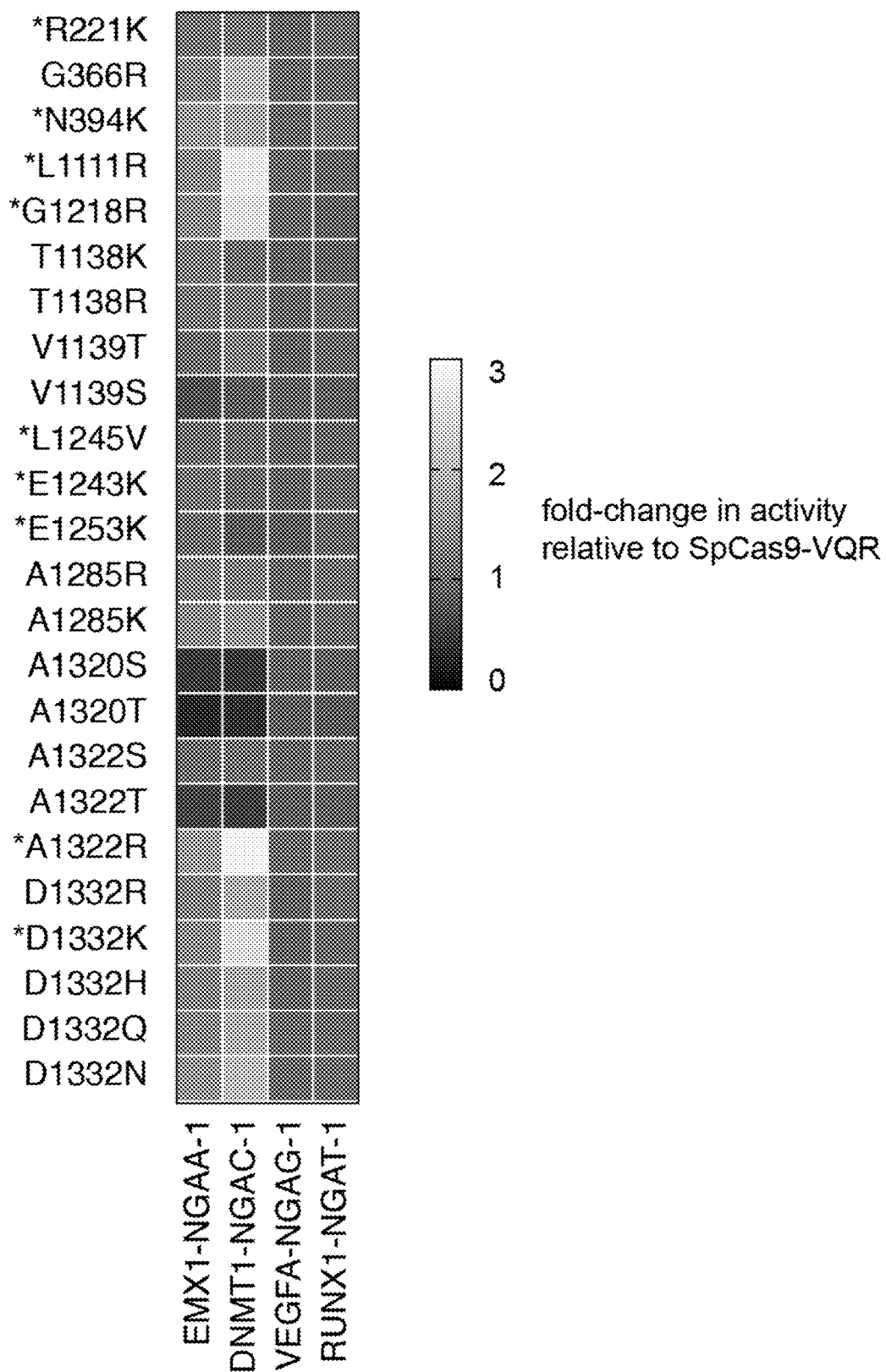

Beyond WT SpCas9, there are other engineered variants or Cas orthologs that could benefit from improved on-target editing activities. As an example, we previously engineered the SpCas9-VQR variant that can target non-canonical NGA PAMs instead of sites with NGG PAMs, albeit at reduced relative rates[8,9]. In a subsequent study, we found that the addition of the G1218R substitution to -VQR to generate the VRQR variant improved on-target gene disruption[9]. These results suggested that attenuated variants, like SpCas9-VQR, might benefit from compensatory substitutions that provide supplementary energetic contacts. We therefore wondered whether the same substitutions that we examined with WT SpCas9 might be more capable of improving the activity of SpCas9-VQR (FIG. 2A). We compared the activity of SpCas9-VQR to 24 derivatives harboring single substitutions and analyzed their editing efficiencies across four target sites in human cells. When using two sgRNAs with lower basal activity with SpCas9-VQR (~25% and ~10%), we now observed several substitutions that improved on-target editing (FIG. 2A, top panel); with two sgRNAs that exhibited higher activities with SpCas9-VQR (~73% and ~50%), we observed only modest changes in editing efficiency (FIG. 2A, bottom panel). While the previously described N394K, L1111R, G1218R, A1322R, and D1332K variants exhibited some of the greatest fold-changes in activity, we also observed substantially improved SpCas9-VQR activity with novel G366R, T1138K, T1138R, A1285K, A1285R, D1332R, D1332H, D1332Q, and D1332N variants (FIG. 2B). These results reveal that single amino acid substitutions designed to generate novel energetic contacts can indeed improve the activity of CRISPR-Cas variants.

Figure 3A:
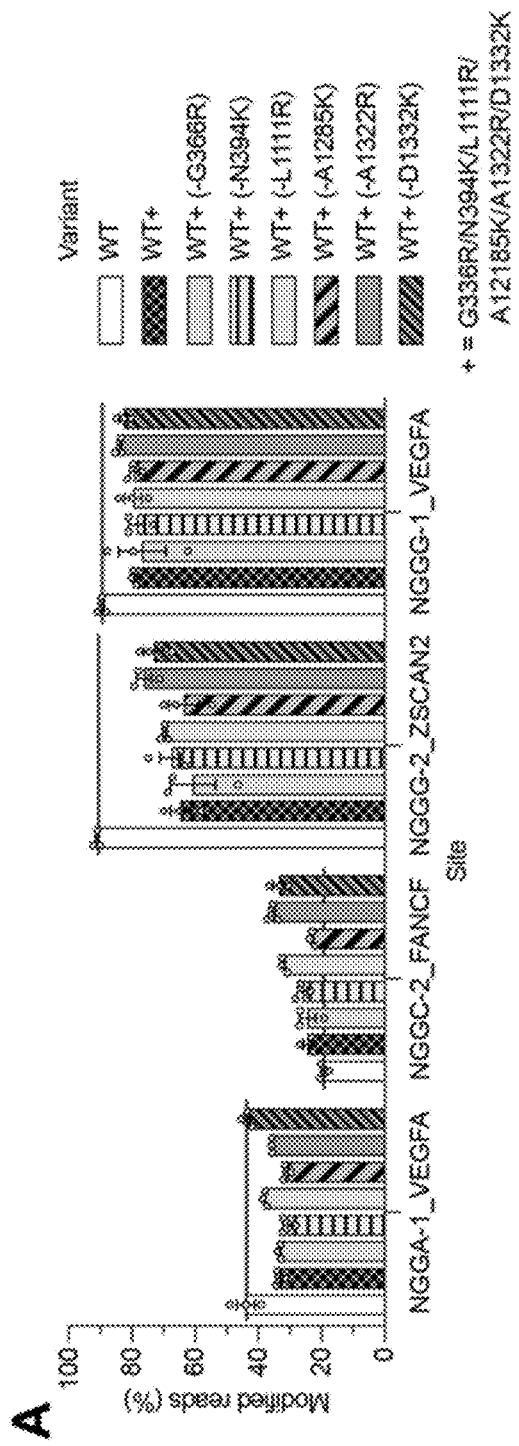
FIGS. 3A-D. Activities of WT SpCas9 and SpCas9-VQR variants bearing multiple activity-enhancing substitutions. A, Modification of endogenous sites in HEK 293T cells bearing NGG PAMs by WT SpCas9 and derivative variants encoding multiple substitutions that improve on-target editing. The '+' variant encodes G366R/N394K/L1111R/A1285K/A1322R/D1332K substitutions with the other derivative variants harboring each possible combination of five of six substitutions. Percent modified reads assessed by targeted sequencing; mean, s.e.m., and individual data points shown for n=3; red line indicates mean modification with WT SpCas9. B, quantification of the editing activities in panel A normalized to the levels of editing observed with WT SpCas9. The normalized activities of variants that improve on-target activity are shown in the blue, and the activities of variants that abrogate activity are shown in red. C, Modification of endogenous sites in HEK 293T cells bearing NGA PAMs by SpCas9-VQR[8] and derivative variants encoding multiple substitutions that improve on-target editing. The '+' variant encodes G366R/N394K/L1111R/A1285K/A1322R/D1332K substitutions with the other derivative variants harboring each possible combination of five of six substitutions. Percent modified reads assessed by targeted sequencing; mean, s.e.m., and individual data points shown for n=3; red line indicates mean modification with SpCas9-VQR. D, quantification of the editing activities in panel C normalized to the levels of editing observed with SpCas9-VQR. The normalized activities of variants that improve on-target activity are shown in the blue, and the activities of variants that abrogate activity are shown in red.
Figure 3B:
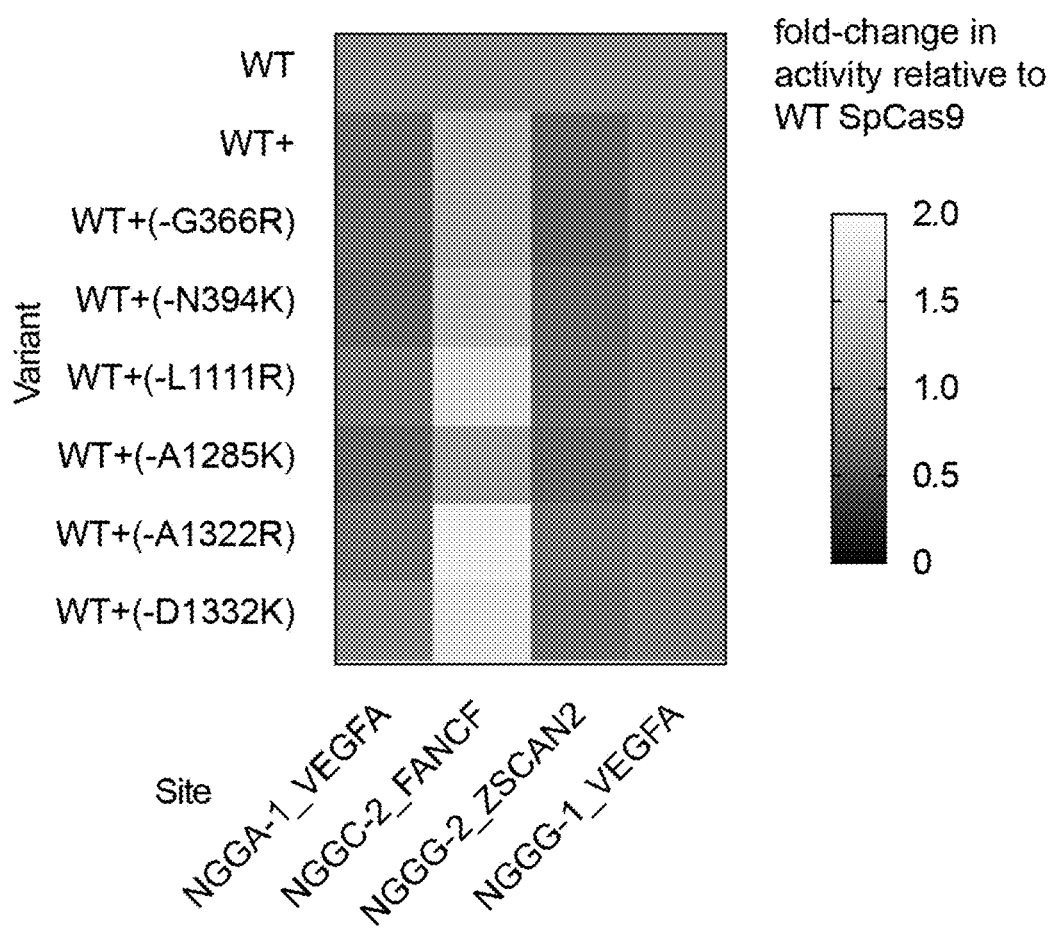
Figure 3C:
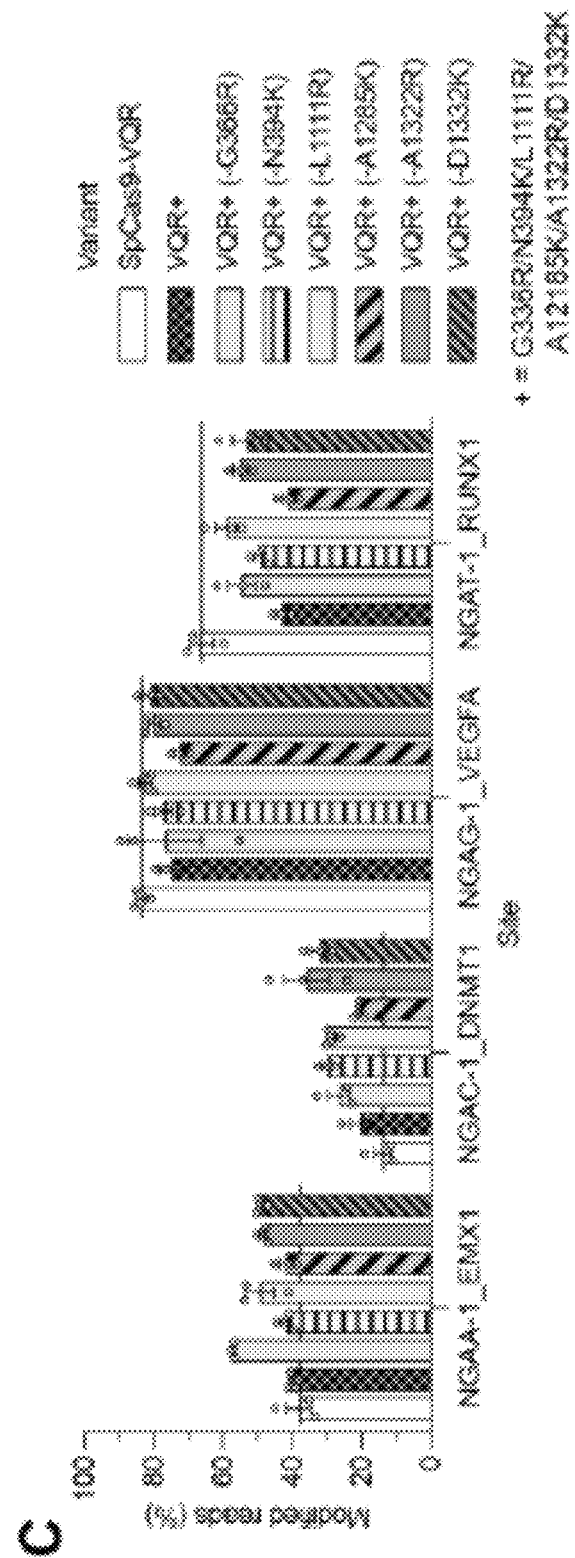
Figure 3D:
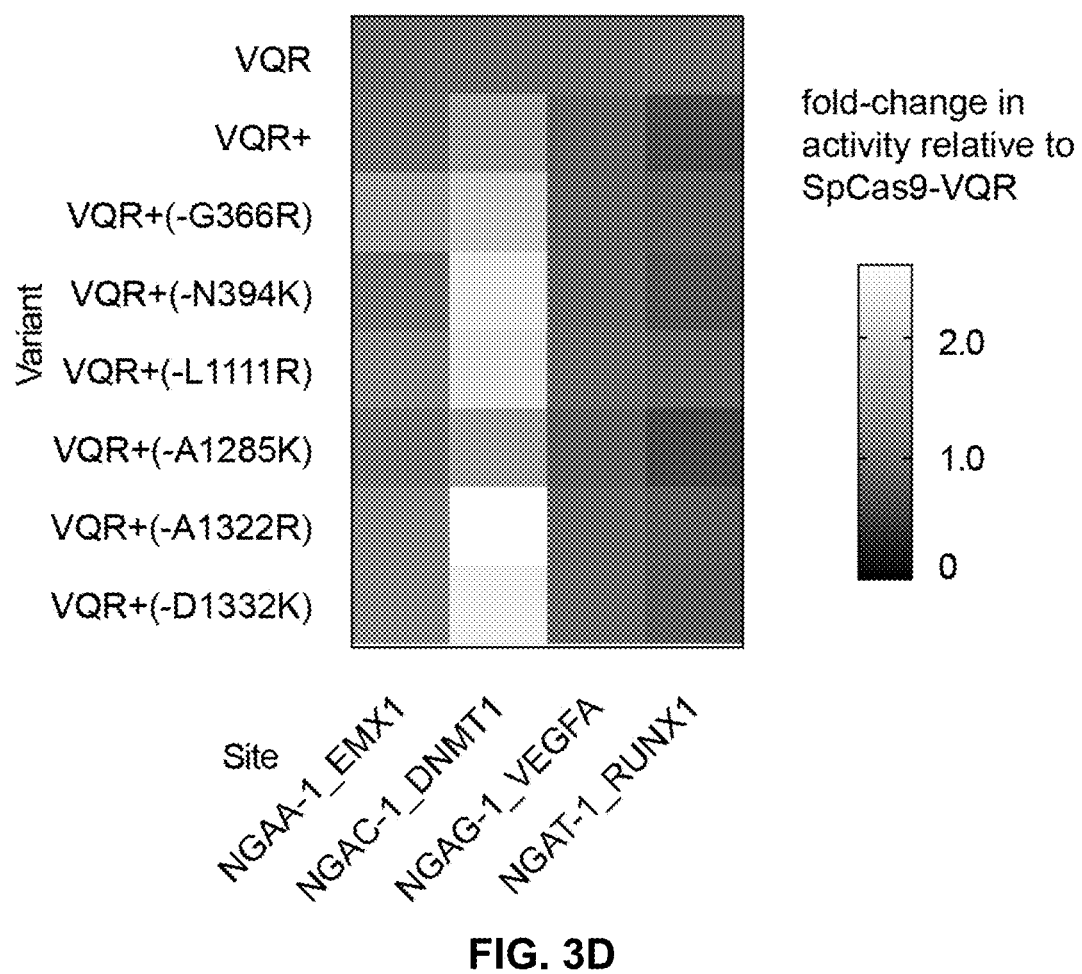

Next we wondered whether we could combine several of the promising substitutions above to potentially observe synergistic improvements in activity. To do so, we examined six of the most promising substitutions, and generated the variants harboring each combination of five substitutions or the variant encoding all six (named 'WT+', with G366R, N394K, L1111R, A1285K, A1322R, and D1332K). We compared the activities of these seven variants to WT SpCas9 across four sites in human cells, and observed improvements in on-target activity for only one site whose basal activity was generally lower (FIGS. 3A and 3B). For the other 3 sites, the combinations of five or six substitutions were consistently detrimental to activity. When testing the same combinations of substitutions in the context of SpCas9-VQR, we observed essentially the same trend with improvements in activity observed only for two of four sites whose basal activity was lower (FIGS. 3C and 3D). With both WT SpCas9 and SpCas9-VQR derivatives, the effectiveness of the variants appeared to be site dependent without a single clear solution. Despite this ambiguity, these experiments demonstrate that WT SpCas9 and SpCas9-VQR are tolerant of as many as six positively charged substitutions in close proximity within the protein, indicating the viability of the strategy. Future studies will be required to more thoroughly understand the optimal compatible combinations of activity-enhancing substitutions. Together, these results suggest that combinations of substitutions can indeed improve on-target editing, but that there may be a limit to the type or combination of activity-enhancing mutations that WT SpCas9 and SpCas9-VQR can tolerate when used on sites that already exhibit medium-to-high levels of editing.

Example 2. Improved Activities of SpCas9 Variants when Combined with L1111R/A1322R Substitutions We next wondered whether the combination of two of the more effective activity-enhancing substitutions, L1111R and A1322R, could improve editing with other engineered SpCas9 PAM variants. In addition to SpCas9-VQR and SpCas9-VRQR (FIGS. 4A and 4B, respectively), we also examined SpCas9-VRER (which we previously published, enabling targeting of sites with NGCG PAMs[8]; FIG. 4C) and SpCas9-MQKSER (a novel SpCas9 variant harboring substitutions that enable targeting of sites with NGCN sites, described in WO2019/040650; FIG. 4D) We compared the activities of the canonical variants to their L1111R/A1322R-harboring derivatives each across four sites in human cells, and in general observed dramatic mean improvements in on-target editing with SpCas9-VQR(L1111R/A1322R), SpCas9-VRER(L1111R/A1322R), and SpCas9-MQKSER (L1111R/A1322R) of approximately 1.3-fold, 3-fold, and 1.5-fold, respectively (FIGS. 4A, 4C, and 4D, respectively). With SpCas9-VRQR (which already encodes the activity-enhancing G1218R and T1337R substitutions), we did not observe significant improvements in on-target editing with the SpCas9-VRQR(L1111R/A1322R) variant (FIG. 4B). These results suggest that for many SpCas9 PAM variants capable of targeting novel PAMs, their on-target activities can be rationally improved with pairs or combinations of directed substitutions.

Figure 5A:
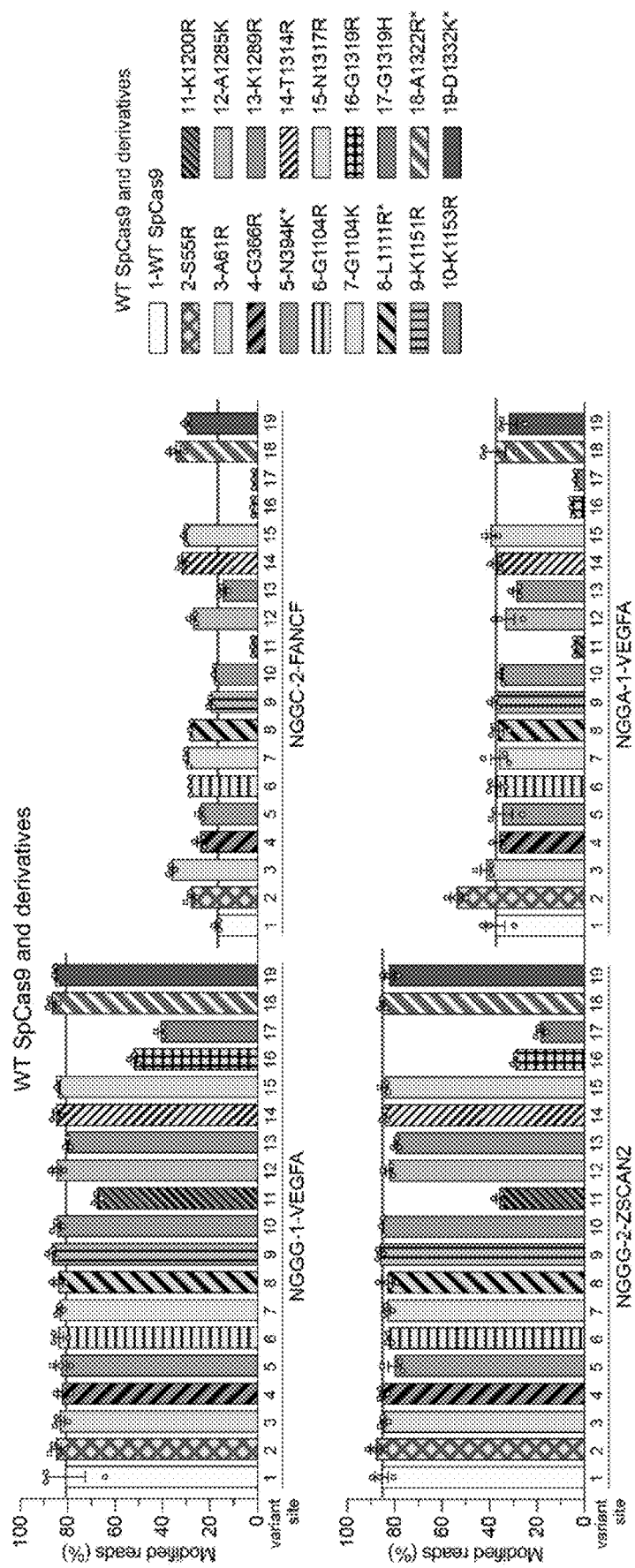
FIGS. 5A-B. Activities of WT SpCas9 and variants bearing additional novel substitutions to improve on-target editing. A, Modification of endogenous sites in HEK 293T cells bearing NGG PAMs by WT SpCas9 and derivative variants encoding substitutions that putatively improve on-target editing. Percent modified reads assessed by targeted sequencing; mean, s.e.m., and individual data points shown for n=3; red line indicates mean modification with WT SpCas9. The '*' symbol indicates variants previously described to improve on-target editing (N394K in WT SpCas9 from ref[12]; L1111R and A1322R in SpCas9-NG from ref[13]; D1332K in SpCas9-QQR1 from ref[11]). B, quantification of the editing activities in panel A normalized to the levels of editing observed with WT SpCas9. The normalized activities of variants that improve on-target activity are shown in the blue, and the activities of variants that abrogate activity are shown in red.
Figure 5B:
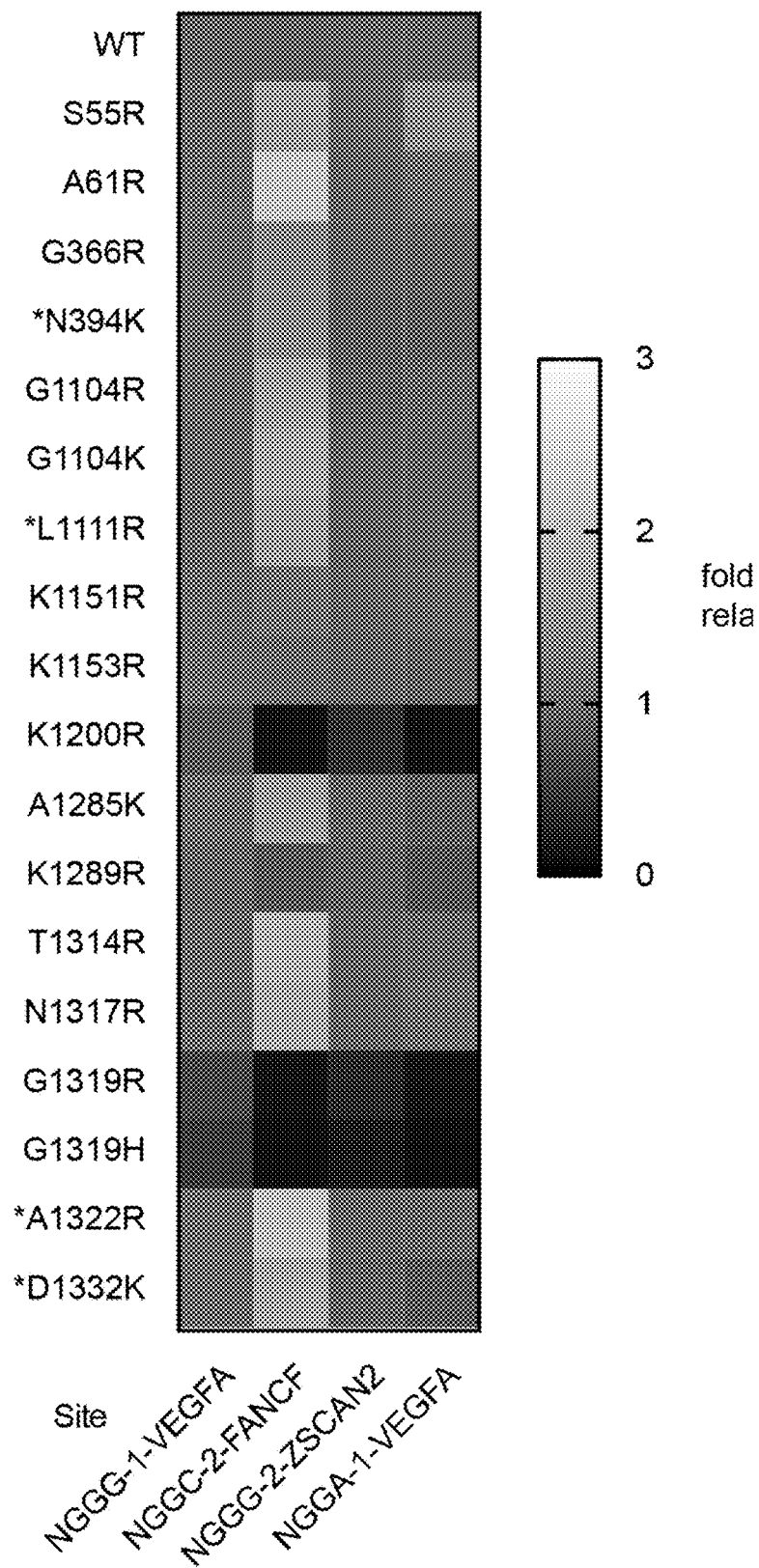

Example 3. Assessment of Additional Novel Activity Enhancing Substitutions in WT SpCas9 and SpCas9-VQR Given our demonstration that it's possible to improve on-target editing activities by making targeted mutations at a small subset of SpCas9 amino acid residues, we wondered whether comparable results could be achieved by making similar substitutions at other positions in SpCas9. We selected other residues whose substitution to positively charged amino acids might stabilize target site recognition, generate novel contacts to the target or non-target DNA backbone, etc. To do so, we generated WT SpCas9 variants harboring S55R, A61R, G1104R, G1104K, K1151R, K1153R, K1200R, K1289R, T1314R, N1317R, G1319R, or G1319H substitutions, and compared their activities to our previously tested G366R, A1285K variants and the previously described N394K, L1111R, A1322R, and D1332K variants (FIG. 5A). We examined the activities of WT SpCas9 and these 18 variants against four sites in human cells, observing once again that substitutions had a minimal impact on sites whose basal activity was originally high with WT SpCas9. However, for the two sites with lower basal activities (~20% and 35% editing), we observed over a 2-fold improvement in activity with some new variants (FIG. 5B). Notably, the S55R, A61R, G366R, G1104R, G1104K, A1285K, T1314R, and N1317R variants consistently exhibited improved activity compared to WT SpCas9, often at levels greater than or equivalent to the prototypical N394K, L1111R, A1322R, or D1332K variants (FIGS. 5A and 5B). These results demonstrate that there are various substitutions in SpCas9 that can improve on-target editing. Interestingly, the K1200R, G1319R, and G1319H substitutions dramatically abrogated activity across all four sites, suggesting that not all positively charged substitutions near the target or non-target DNA backbones can be accommodated by WT SpCas9 (FIG. 5A).

Figure 6A:
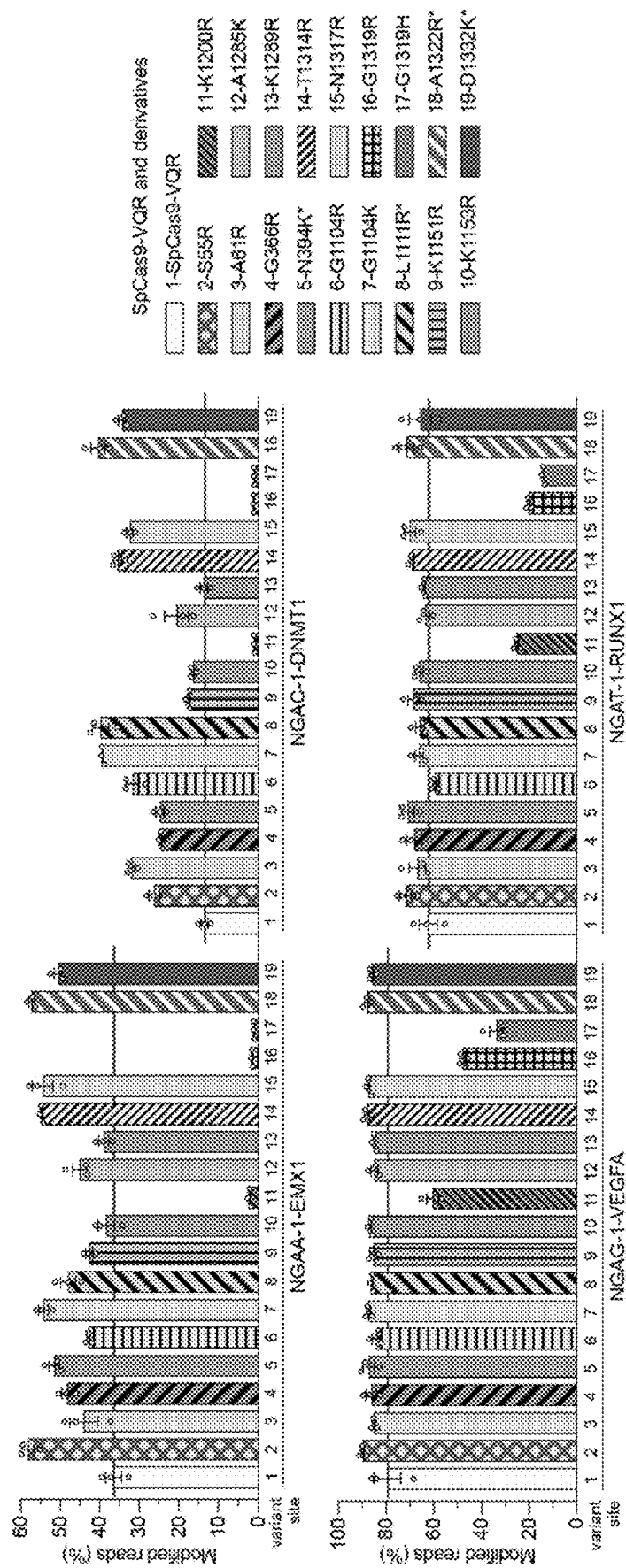
FIGS. 6A-B. Activities of SpCas9-VQR and variants bearing additional novel substitutions to improve on-target editing. A, Modification of endogenous sites in HEK 293T cells bearing NGA PAMs by SpCas9-VQR and derivative variants encoding substitutions that putatively improve on-target editing. Percent modified reads assessed by targeted sequencing; mean, s.e.m., and individual data points shown for n=3; red line indicates mean modification with SpCas9-VQR. The '*' symbol indicates variants previously described to improve on-target editing (N394K in WT SpCas9 from ref[12]; L1111R and A1322R in SpCas9-NG from ref[13]; D1332K in SpCas9-QQR1 from ref[11]). B, quantification of the editing activities in panel A normalized to the levels of editing observed with SpCas9-VQR. The normalized activities of variants that improve on-target activity are shown in the blue, and the activities of variants that abrogate activity are shown in red.
Figure 6B:
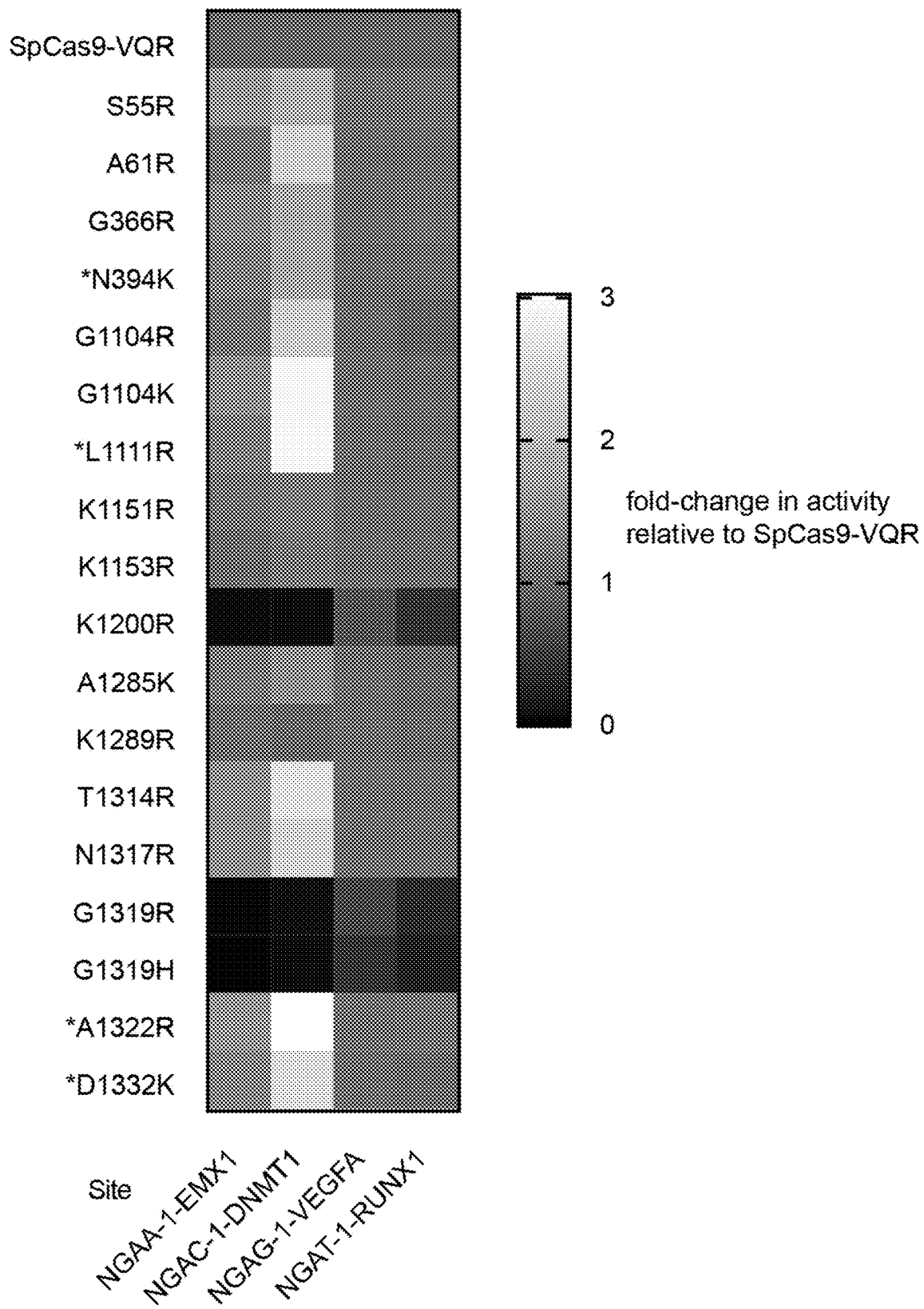

We also assessed the impact of these same substitutions in the context of SpCas9-VQR across four sites in human cells harboring NGA PAMs (FIG. 6A). For nearly all variants we observed increased activities, with the effect being more prominent on two of the four sites. (FIGS. 6A and 6B). Similar to our observations with WT SpCas9, we found that the SpCas9-VQR derivatives harboring K1200R, G1319R, and G1319H substitutions were detrimental to activities. Collectively, these results reveal that additional novel substitutions can improve the on-target editing activities of SpCas9 variants.

Example 4. Energetic Supplementation of NGN PAM-Targeting Variants Via Non-Specific Contacts We previously engineered a novel SpCas9 variant, named SpG, harboring the mutations D1135L/S1136W/G1218K/E1219Q/R1335Q/T1337R and capable of targeting an expanded number of target sites bearing NGN PAMs. To further improve the on-target activity of SpG, we wondered whether the variant could tolerate substitutions intended to form non-specific DNA contacts and thus improve the overall interaction energy of SpG with the PAM. A similar strategy was previously described for SpCas9-NG, which harbors L1111R and A1322R substitutions hypothesized to form DNA backbone contacts to compensate for the loss of base-specific interactions to the $3^{rd}$ position of the PAM caused by the R1335V substitution[13]. To investigate this hypothesis, we first determined whether the L1111R and A1322R substitutions are essential for the activities of SpCas9-NG. We compared the on-target editing of SpCas9-NG to the R1111L, R1322A, and R1111L/R1322A derivative variants that lack the supplementary energetic contacts across 16 sites harboring NGNN PAMs in human cells (FIGS. 7A and 7B). We found that the inclusion of both arginine substitutions is necessary for the activities observed with SpCas9-NG.

We then determined whether the same substitutions could improve the editing efficiencies of SpG by generating derivative variants harboring L1111R, A1322R, or both substitutions. When we assessed the activities of these SpG(L1111R), SpG(A1322R), and SpG(L1111R/A1322R) across the same 16 sites harboring NGNN PAMs in human cells, we surprisingly observed a reduction in the on-target activities for 14 of 16 sites with most variants (FIGS. 7C and 7D). These results suggest that the substitutions in SpG that result in expanded PAM recognition do not require energetic supplementation, or possibly that the L1111R and A1322R substitutions are not compatible with the contextual changes generated by the SpG substitutions. Thus, the inclusion of substitutions to improve the on-target editing of SpCas9 variants is non-trivial and requires investigation to identify compatible sets of mutations.

Since the L1111R and A1322R substitutions presumably generate novel non-specific contacts to the DNA backbone near the PAM, we wondered whether these substitutions influence PAM specificity. To determine sequences targetable by SpG, SpG(L1111R/A1322R), SpCas9-NG, and SpCas9-NG(R1111L/R1322A), we performed high-throughput PAM determination assay (HT-PAMDA) experiments to determine the PAM profiles of these variants. The HT-PAMDA showed that the presence or absence of L1111R and A1322R in either variant did not appear to alter their PAM preferences (FIGS. 8A and 8B), suggesting that the major roles of L1111R and A1322R substitutions are energetic rather than PAM preference altering.

Next, we wondered whether activity-enhancing substitutions beyond L1111R and A1322R could improve the on-target editing observed with SpCas9-NG or SpG. We generated derivative variants of these two proteins harboring some of the most promising single substitutions from our previous experiments (FIGS. 1, 2, 5, and 6), as to well as other previously unexamined L1111K and A1322K mutations. We tested their activities of this series of variants on three sites with NGCG, NGGA, and NGTG PAMs (FIGS. 9A-9D). In general, we observed that these substitutions were mostly unable to improve the effectiveness of SpCas9-NG or SpG, with the exception of G366R, L1111R, A1285K, or N1317R in the context of SpG on the site with lowest basal activity (~20%). Similar to our previous finding with SpG(L1111R/A1322R), these results demonstrate that it might be difficult to further improve the activity of variants that already exhibit generally robust activities.

Example 5. Expansion of SpCas9 Targeting Range Requires Activity-Enhancing Substitutions Notwithstanding the efficient modification of sites with NGN PAMs in human cells using the SpG variant, many genomic regions remain inaccessible for genome editing. We speculated that SpG could be utilized as a molecular scaffold upon which to further relax PAM specificity. To alter recognition of the $2^{nd}$ position of the PAM, we focused on mutating R1333 since substitution to glutamine might enable access to sites harboring NAN PAMs, presumably by forming a base specific contact with the adenine base in the second position of the PAM[8,11,15] (FIG. 10A). Our initial tests of SpG(R1333Q) nearly abolished activity in human cells against four sites bearing NRN PAMs (where R is A and G) (FIG. 10B), revealing that the R1333Q alone was insufficient to enable highly active targeting of NAN PAMs (consistent with previous reports for WT SpCas9[8,15]). Interestingly, contrary to our previous finding that L1111R and A1322R substitutions negatively impacted SpG activity (FIGS. 7C and 7D), we now observed that the addition of these non-specific DNA contacts were able to rescue activity of SpG(R1333Q) across the four sites bearing NRN PAMs in human cells (FIG. 10B). Concurrent HT-PAMDA experiments to analyze the same variants corroborated a general relaxation of PAM specificity against NR PAMs but with a lower overall activity (FIG. 10B). These results demonstrate that the activity-enhancing L1111R and A1322R substitutions can improve the on-target editing efficiency of the attenuated SpG(R1333Q) variant.

Next, to determine whether the R1333Q substitution in SpG(R1333Q/L1111R/A1322R) was the most permissive for recognition of an expanded number of PAMs, we investigated whether variants harboring other amino acid substitutions at residue 1333 might be more amenable to highly active and broad targeting of NRN PAMs. Systematic evaluation of SpG(L1111R/A1322R) variants harboring all 20 possible amino acids at residue 1333 revealed that the range substitutions at this position cause different 2nd PAM position preferences and overall levels of activity. Surprisingly, variants bearing R1333 substitutions to alanine, cysteine, or proline conferred the most efficient collective targeting of NRN PAMs. Human cell experiments against the same four sites harboring NRN PAMs demonstrated that one SpG (L1111R/A1322R) variant that also harbored an R1333P substitutions exhibited greater activity on NRN PAMs compared to the precursor R1333Q-containing variants (FIG. 10B). HT-PAMDA experiments confirmed these observations (FIG. 10C).

Figure 11A:
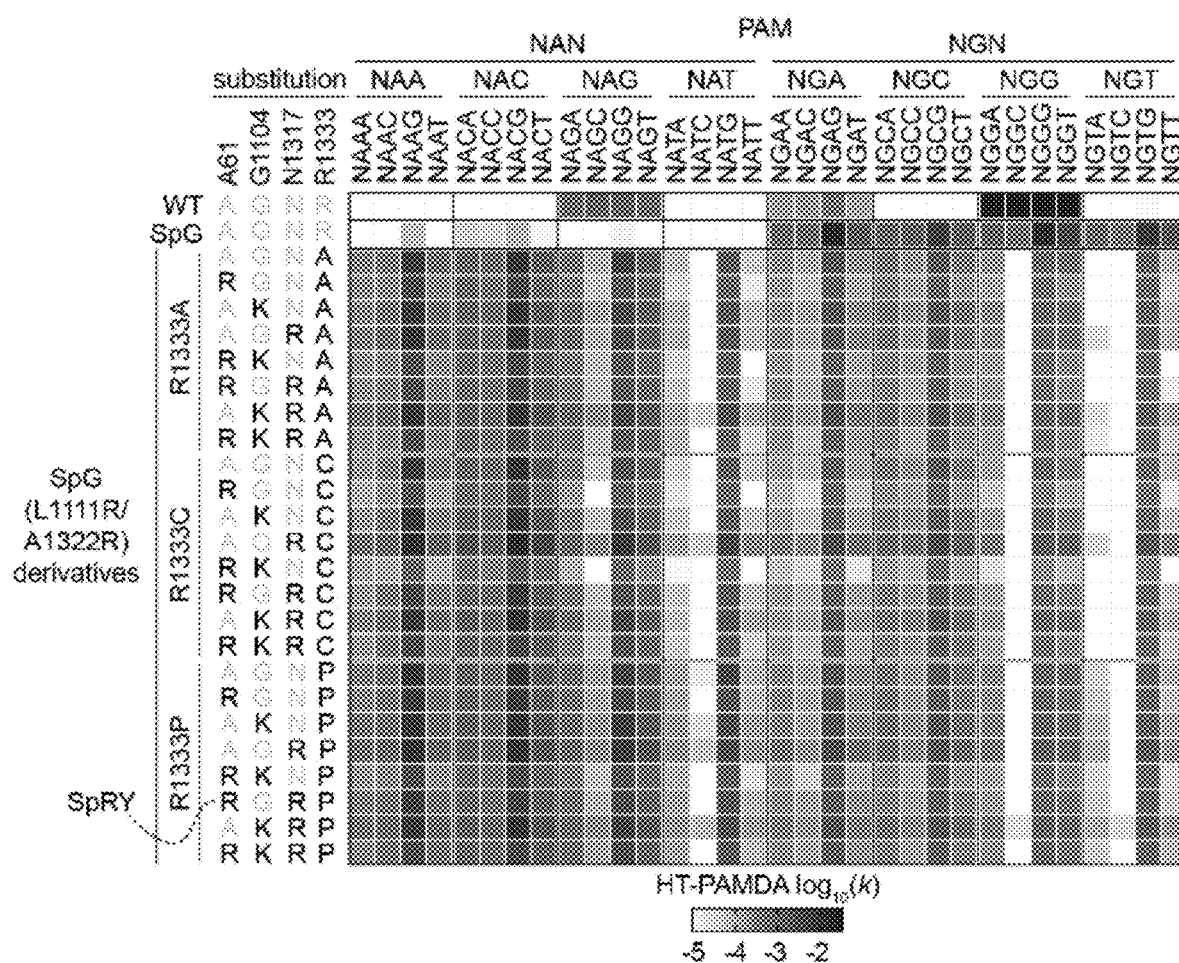
FIGS. 11A-C. Improving the activities of SpCas9 variants for efficient targeting of NR PAM sequences. A, HT-PAMDA NRNN nt PAM profiles of of SpG(L1111R/A1322R) derivatives bearing substitutions at A61, G1104, and N1317 in the context of R1333A/C/P. B, Modification of four endogenous sites in HEK 293T cells bearing NRN PAMs by SpG(L1111R/A1322R) derivatives. Percent modification assessed by targeted sequencing; mean, s.e.m., and individual data points shown for n=3. C, HT-PAMDA NNNN PAM profiles of SpG, SpRY, and selected intermediate variants. For panels A and C, HT-PAMDA $\log_{10}(k)$ are the mean of at least two replicates against two distinct spacer sequences.

Given that the addition of L1111R and A1322R to SpG (R1333Q) improved on-target activity, we wondered whether additional analogous substitutions could further enhance editing of sites with NRN PAMs. To do so, we determined whether some of the most promising single substitutions from our previous experiments (A61R, G1104K, and N1317R) could improve on-target editing (FIG. 10A). We utilized HT-PAMDA to determine the single or combinatorial effects of three such substitutions, A61R, G1104K, or N1317R, in the context of SpG(L1111R/A1322R) variants also bearing R1333A, R1333C, or R1333P substitutions (FIGS. 10C and 11A). This analysis revealed that different combinations of the three non-specific substitutions were well-tolerated by nearly all variants, and that the NRN PAM-preferences of variants harboring R1333A, C, or P substitutions were similar by HT-PAMDA.

Figure 11B:
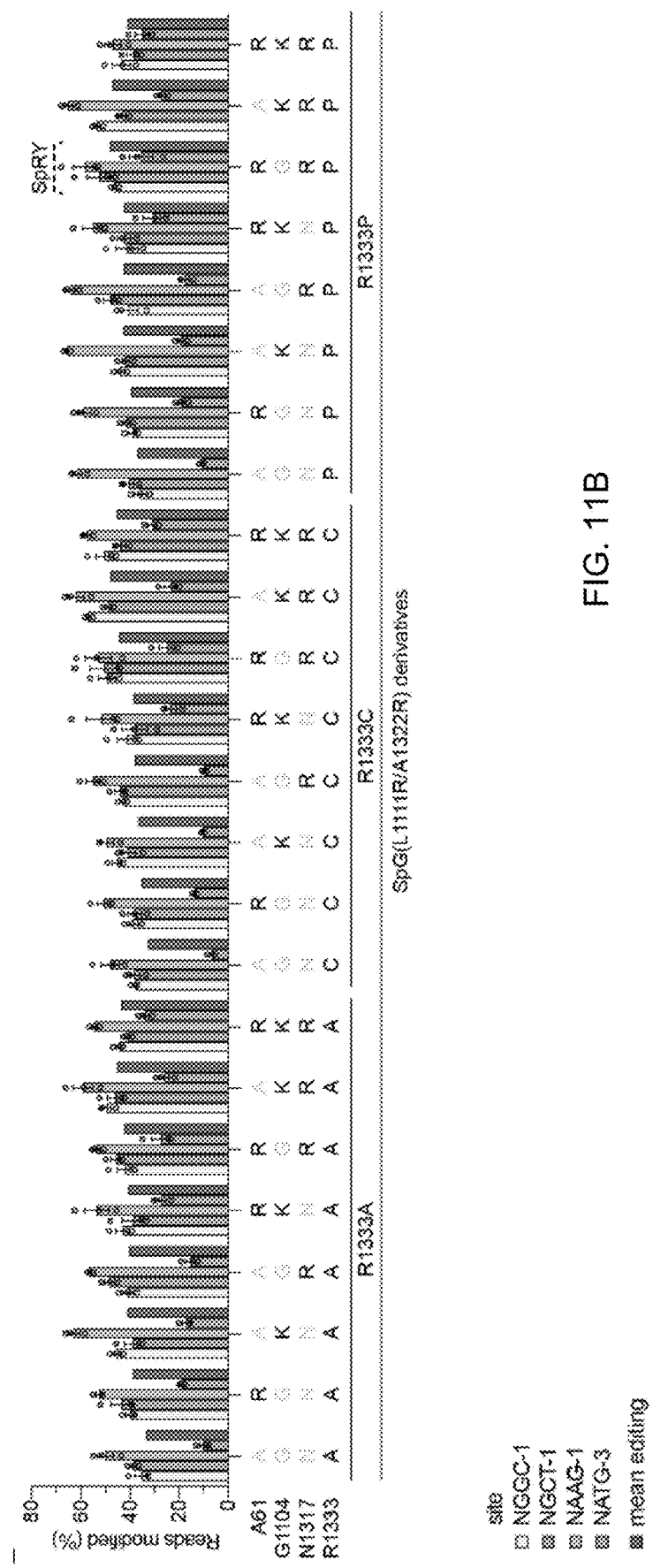
Figure 11C:
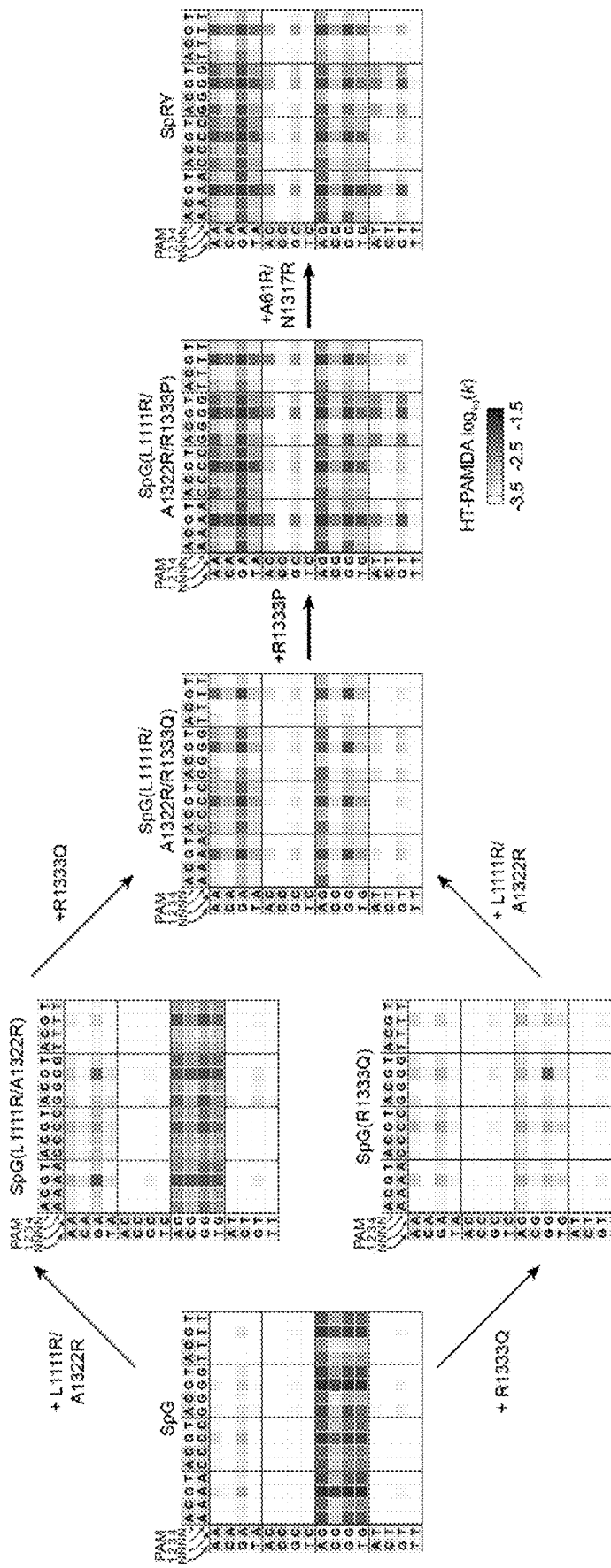

To determine which variant exhibited the highest on-target activity in human cells, we tested this large series of variants against four additional sites bearing NRN PAMs (FIG. 11B). We observed that the SpG(L1111R/A1322R) variant harboring the R1333P substitution and a combination of A61R/N1317R offered the greatest mean editing against NRN PAMs (FIG. 10D). Use of HT-PAMDA to examine the sequential effects of the substitutions encoded by this variant demonstrated a step-wise progression from NGN to NRN PAM preference, and also revealed the surprising finding that this variant may target some NYN PAMs (where Y is C or T; FIG. 11C). Taken together, our human cell and HT-PAMDA data suggest that the SpG (L1111R/A1322R) derivative encoding R1333P along with activity-enhancing A61R and N1317R substitutions (henceforth referred to as SpRY, for SpCas9 variant capable of targeting NRN>NYN PAMs, harboring the mutations A61R/L1111R/D1135L/S1136W/G1218K/E1219Q/N1317R/A1322R/R1333P/R1335 Q/T1337R) enables targeting of sites with NR PAMs.

Example 6. SpRY Activities as a Nuclease, CBE, and ABE in Human Cells

Having established the potential of SpRY to widely expand sequence targeting, we more thoroughly assessed its nuclease activities in human cells. We compared the on-target editing of WT SpCas9 and SpRY across 64 sites, 32 each harboring NANN and NGNN PAMs (FIG. 12A). Using non-saturating nuclease expression conditions in HEK 293T cells, we observed that WT SpCas9 preferred NGG>NAG>NGA PAMs with negligible targeting of the remaining NRN PAMs (FIG. 12A). In comparison, SpRY was far more effective than WT at targeting sites encoding NRN PAMs, except for sites harboring canonical NGG PAMs (FIG. 12A). Overall, SpRY was capable of efficiently targeting the majority of target sites with NRN PAMs, where the range of activities could not necessarily be explained by PAM preference alone. These results demonstrate, for the first time, the ability to effectively target a range of sites with NAN PAMs using a Cas9 variant.

Combined with our prior observation of modest levels of NYN targeting with SpRY in HT-PAMDA (FIG. 11C), structural analysis of the R1333P substitution in SpRY led us to speculate that R1333P-containing variants might also enable targeting of any base in the 2nd PAM position (including thus far unexamined NYN PAMs). To test this hypothesis, we examined the activities of WT SpCas9 and SpRY across 31 sites with NYN PAMs (15 NCNN and 16 NTNN sites; FIG. 12B). Surprisingly, SpRY was able to edit 13 of 31 sites (42%) with NYN PAMs to levels higher than 20% modification, compared to 0 sites with WT SpCas9 (FIG. 12B). While the mean editing activities on sites with NYN PAMs were approximately half of what we observed on sites with NRN PAMs, the activities were far greater than the essentially negligible editing with WT SpCas9 (FIG. 12B). Collectively, these results demonstrate the ability to target sites with NRN PAMs and some NYN PAMs with SpCas9 for the first time.

Figure 12C:
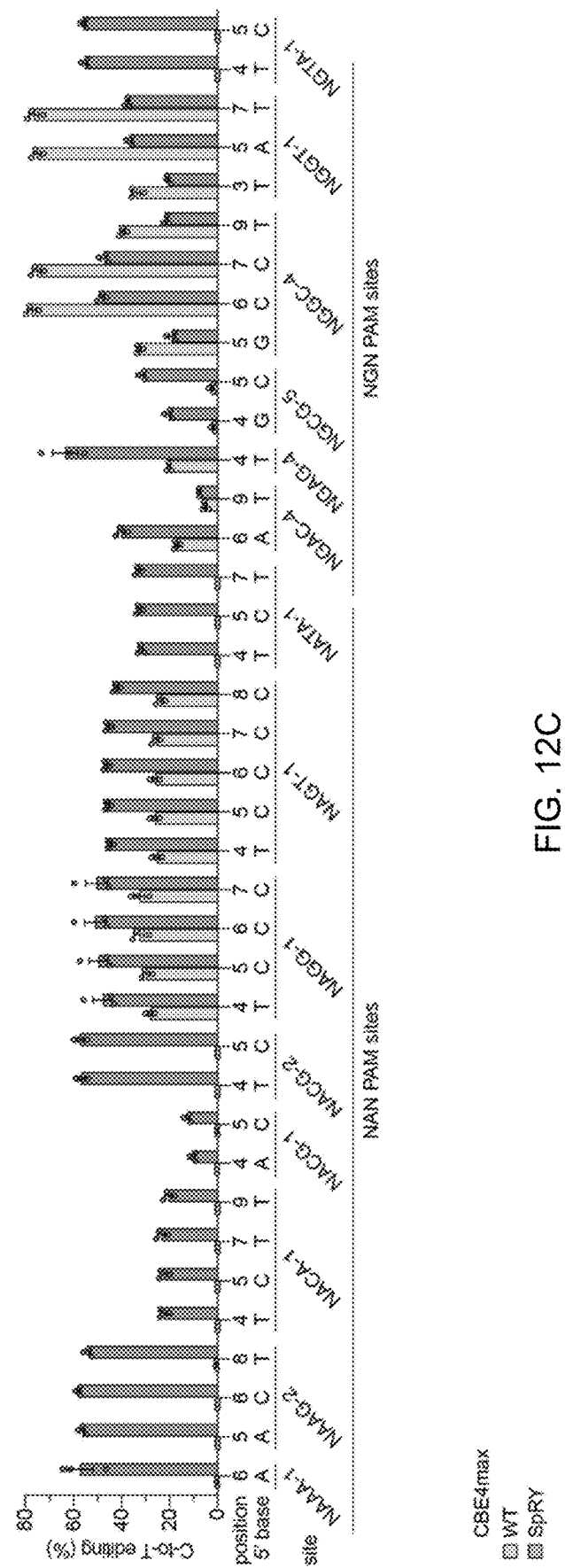
Figure 12D:
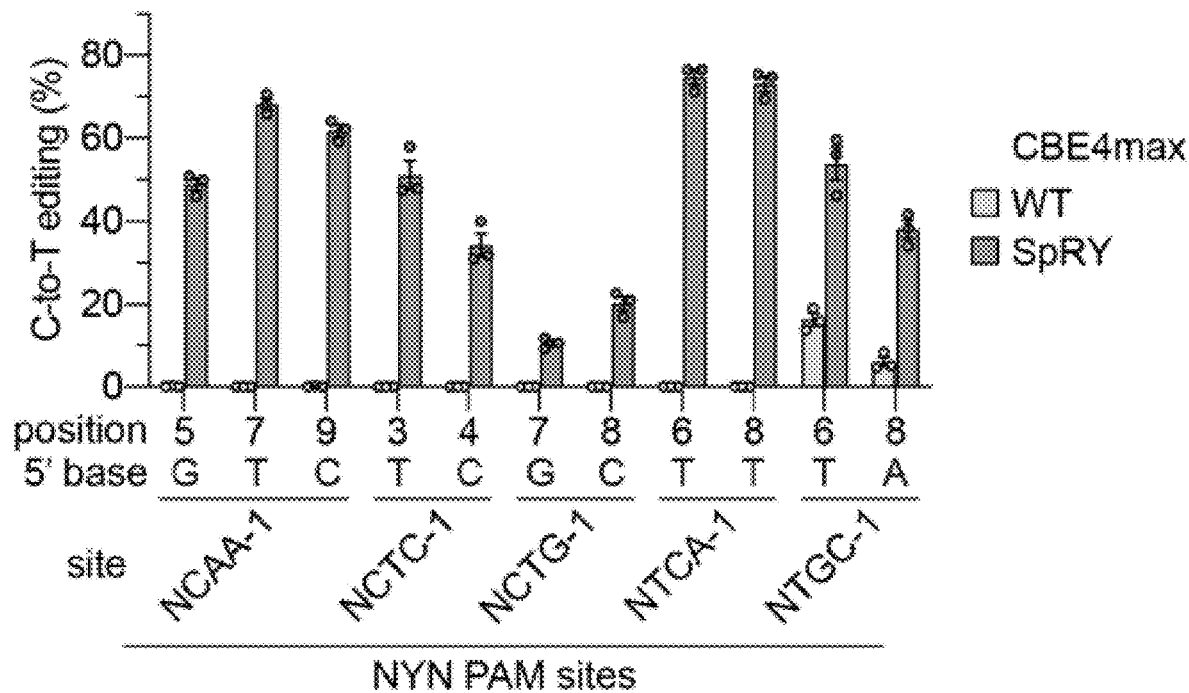

Because SpRY enables nuclease targeting of many sites with NNN PAMs in human cells, we examined its compatibility with C-to-T base editors[16,17] given their dependence on the availability of PAMs to appropriately position the CBE or ABE edit windows. Assessment of SpRY-CBE across 14 sites bearing NRN PAMs revealed mean C-to-T editing of 38.0% across all substrate cytosines (FIG. 12C), with SpRY-CBE achieving greater than 20% modification of at least one cytosine per site for all but one site. Comparatively, WT-CBE modified sites bearing NGG PAMs most efficiently, though was also capable of modifying sites bearing NAG and NGA PAMs, albeit at lower efficiency that SpRY (FIG. 12C). We also assessed the activities SpRY-CBE on five high-activity NYN PAM sites from our previous nuclease datasets. For these pre-selected high-activity sites, we observed robust levels of editing compared to negligible editing with WT-CBE (FIG. 12D).

Figure 12E:
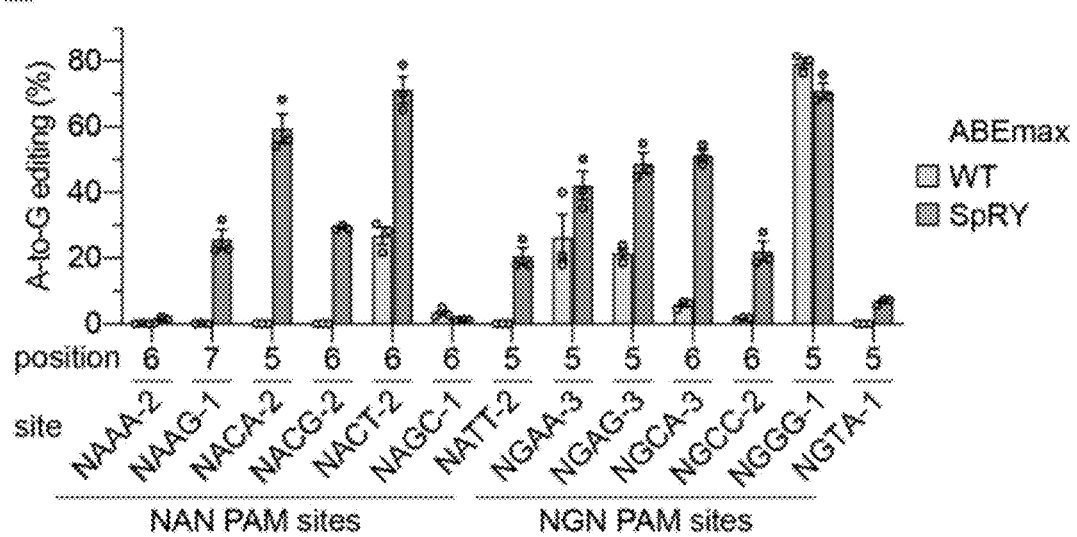
Figure 12F:
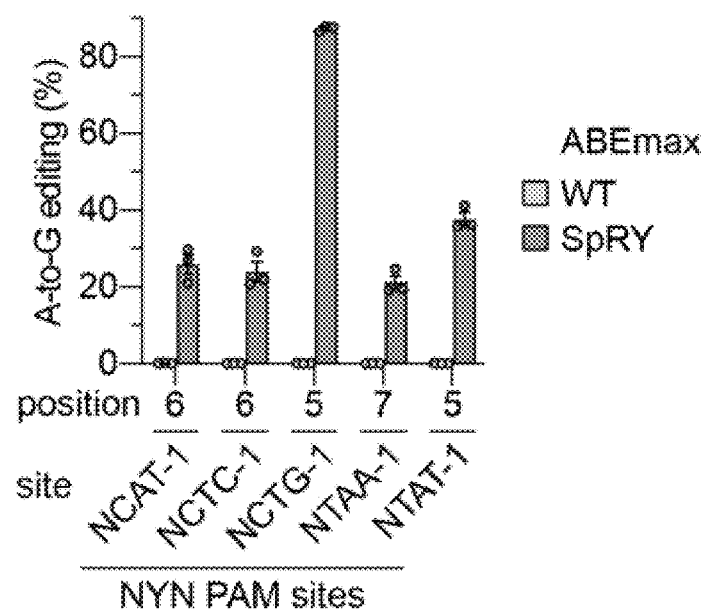

We then examined the A-to-G base editor[17,18] activities of SpRY-ABE across 13 sites with NRN PAMs, and also for 5 high-activity sites with NYN PAMs (the latter from FIG. 12E). For the NRN PAM sites, we observed mean A-to-G editing activities of 34.7% with SpRY-ABE on substrate adenines and achieved greater than 20% modification on at least one adenine for 10 of 13 sites (FIG. 12E). With WT-ABE, the most efficient editing was observed on the NGG PAM site and minor editing detected on 3 sites with non-canonical PAMs (FIG. 12E). Across the five pre-selected high activity sites harboring NY PAMs, A-to-G editing activities were generally more modest with SpRY but we did observe editing of one adenine to near 90%; no editing with WT ABEmax was observed on any of the five sites (FIG. 12F).

Collectively, these results show that activity-enhancing substitutions enable the engineering of novel SpCas9 variants that can effectively target previously inaccessible PAMs and genomic regions.

Example 7. Activity Enhancing Substitutions can Improve the On-Target Activities of Cas9 PAM Variants Next, we more thoroughly investigated whether a selection of activity enhancing substitutions could improve the on-target activities of various SpCas9 PAM variants. To characterize the effect of the activity enhancing substitutions, we selected four PAM variants of SpCas9, including: (1) SpCas9-VRQR (described in Kleinstiver et al., Nature 523, 481-485 (2015) and Kleinstiver et al., Nature 529, 490-495 (2016), bearing D1135V/G1218R/R1335Q/T1337R substitutions), which has a preference for NGAN>NGNG PAMs, (2) SpCas9-VRER (described in Kleinstiver et al., Nature 523, 481-485 (2015), bearing D1135V/G1218R/R1335E/T1337R substitutions), which has a preference for NGCG PAMs, (3) SpCas9-MQKSER (described in WO2019/040650, bearing D1135M/S1136Q/G1218K/E1219S/R1335E/T1337R substitutions), which has a preference for NGCN>NGNG PAMs, and (4) SpCas9-VRAVQL (described in WO2019/040650, bearing D1135V/S1136R/G1218A/E1219V/R1335Q/T1337L substitutions), which has a preference for NGTN PAMs. In the background of each of these four variants, we a series of derivatives harboring additional single substitutions, as well as single substitutions in the context of the PAM variants with L1111R/A1322R substitutions.

Figure 15:
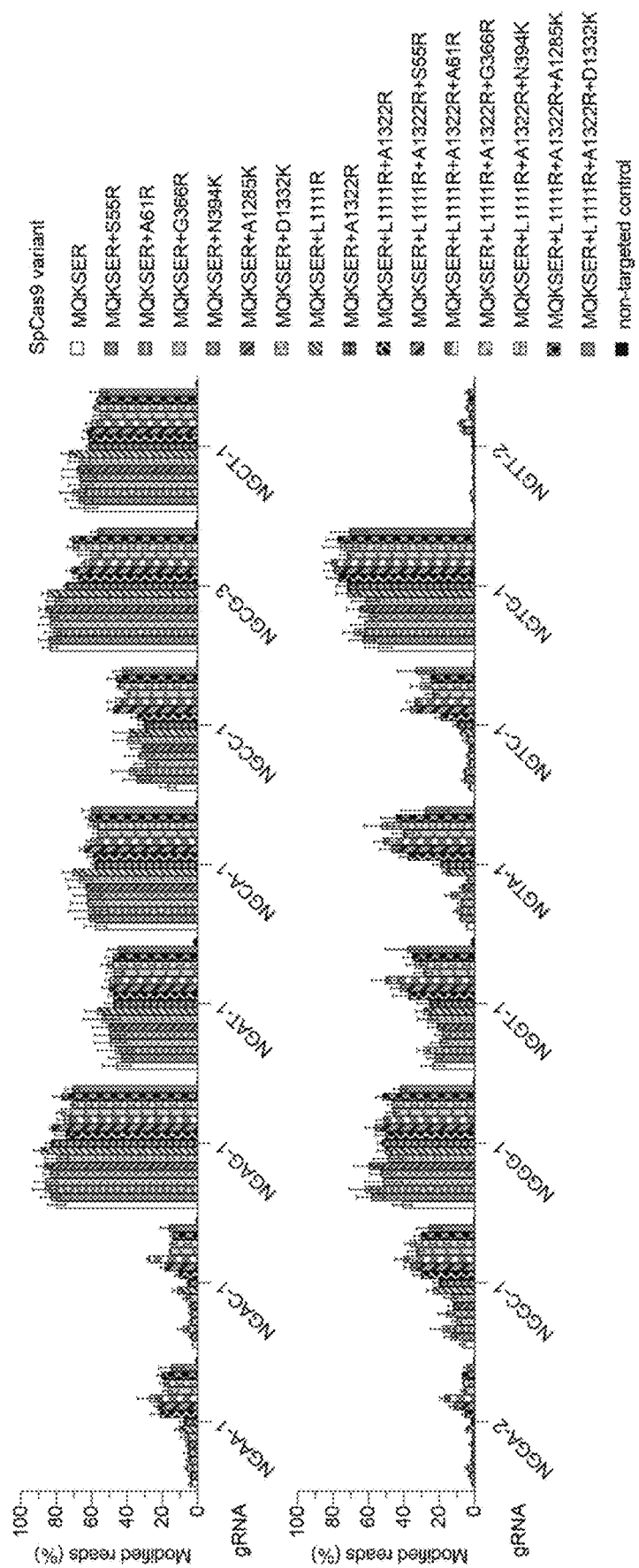
FIG. 15. Activities of SpCas9-MQKSER and variants bearing additional substitutions. Modification of endogenous sites in HEK 293T cells bearing NGNN PAMs by SpCas9-MQKSER (bearing D1135M/S1136Q/G1218K/E1219S/R1335E/T1337R substitutions) and derivative variants encoding substitutions that putatively improve on-target editing. Percent modified reads assessed by targeted sequencing; mean, and s.e.m. shown for n=3.
Figure 16:
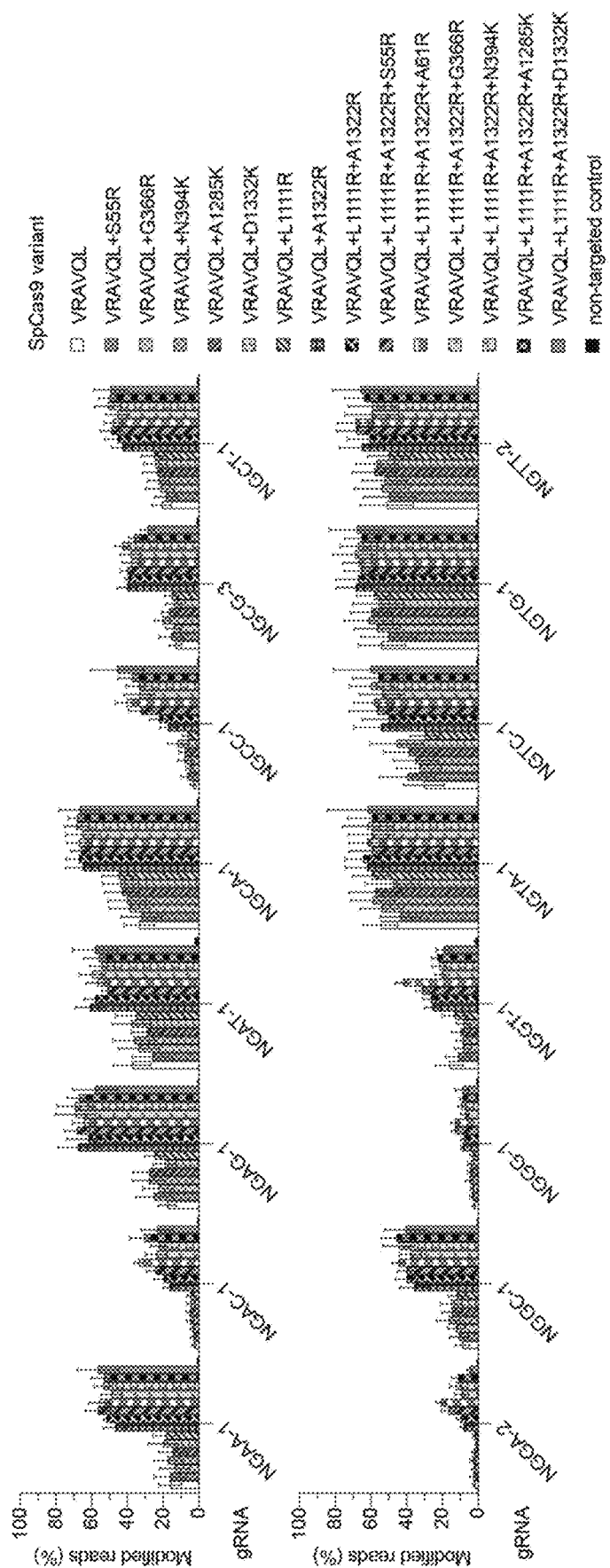
FIG. 16. Activities of SpCas9-VRAVQL and variants bearing additional substitutions. Modification of endogenous sites in HEK 293T cells bearing NGNN PAMs by SpCas9-VRAVQL (bearing D1135V/S1136R/G1218A/E1219V/R1335Q/T1337L substitutions) and derivative variants encoding substitutions that putatively improve on-target editing. Percent modified reads assessed by targeted sequencing; mean and s.e.m. shown for n=3.

To assess the impact of the putative activity-enhancing substitutions, we performed experiments in human cells to evaluate any changes in on-target activity. We transfected plasmids encoding the SpCas9 PAM variants and a separate plasmid that expresses the guide RNA (gRNA) into HEK 293T cells, and 72 hours later extracted genomic DNA for targeted sequencing at 16 different on-target sites. The gRNAs and corresponding on-target sites encompassed a range of PAMs, with one each from the possible NGAN, NGCN, NGGN, and NGTN sequences (Table 4). We investigated the impact of the activity enhancing substitutions on SpCas9-VRQR (FIG. 13), SpCas9-VRER (FIG. 14), SpCas9-MQKSER (FIG. 15), and SpCas9-VRAVQL (FIG. 16).

TABLE 4

Sequences of target sites for experiments in FIGS. 13-16

| Site ID | Prep ID | spacer sequence (no PAM) | # | 4 nt PAM | target gene |
|---|---|---|---|---|---|
| NGAA-1 | MSP813 | GCTGAGCTGAGAGCCTGATG | 4 | GGAA | EMX1 |
| NGAC-1 | RTW3811 | GGCCAGCCCAGCAGCCAACC | 5 | TGAC | DNMT1 |
| NGAG-1 | BPK1846 | GCGAGCAGCGTCTTCGAGAG | 6 | TGAG | VEGFA |
| NGAT-1 | MSP829 | GCAGAGGGAGAAGAAAGAG | 7 | AGAT | RUNX1 |
| NGCA-1 | MMW2247 | GCGGCTGCACAACCAGTGGA | 8 | GGCA | FANCF |
| NGCC-1 | MMW2260 | GACTCAAATATGCTGTCTGA | 9 | AGCC | RUNX1 |
| NGCG-3 | MSP1062 | GCAGAAGGGATTCCATGAGG | 10 | TGCG | FANCF |
| NGCT-1 | MMW2254 | GCTCGGAAAAGCGATCCAGG | 11 | TGCT | FANCF |
| NGGA-2 | BPK3128 | GAGTGCTAAGGGAACGTTCA | 12 | CGGA | DNMT1 |
| NGGC-1 | FYF1548 | GAGTCCGAGCAGAAGAAGAA | 13 | GGGC | EMX1 |
| NGGG-1 | VC228 | GGTGAGTGAGTGTGTGCGTG | 14 | TGGG | VEGFA |
| NGGT-1 | BPK3127 | GTCACTCTGGGGAACACGCC | 15 | CGGT | DNMT1 |
| NGTA-1 | MMW1157 | GTTCCAGAACCGGAGGACAA | 16 | AGTA | EMX1 |
| NGTC-1 | MMW1229 | GGCCCGGCGCACGGTGGCGG | 17 | GGTC | FANCF |
| NGTG-1 | MSP1071 | GTCCCCGCCTTCAGAAGAG | 18 | GGTG | RUNX1 |
| NGTT-2 | MMW1182 | GACTTGTAATCATATGCCTC | 19 | AGTT | RUNX1 |

Figure 13:
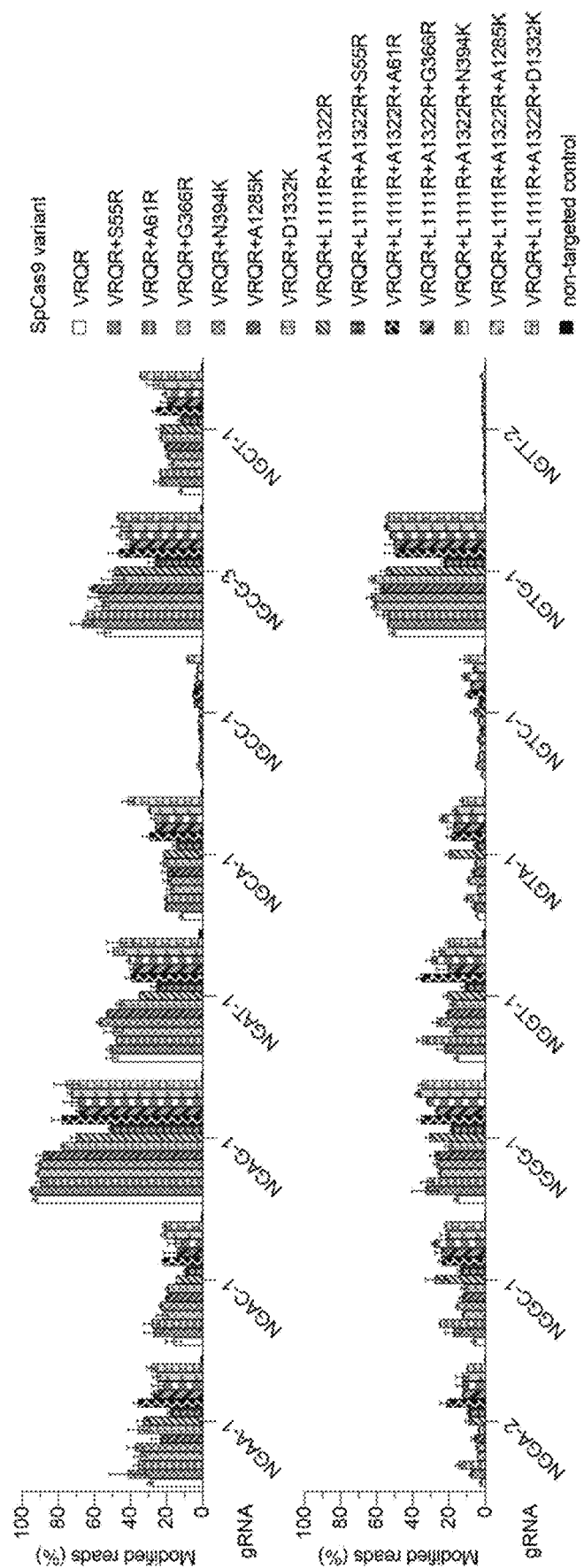
FIG. 13. Activities of SpCas9-VRQR and variants bearing additional substitutions. Modification of endogenous sites in HEK 293T cells bearing NGNN PAMs by SpCas9-VRQR (bearing D1135V/G1218R/R1335Q/T1337R substitutions) and derivative variants encoding substitutions that putatively improve on-target editing. Percent modified reads assessed by targeted sequencing; mean and s.e.m. shown for n=2.

, SEQ ID NO:

For SpCas9-VRQR, we separately added the S55R, A61R, G366R, N394K, A1285K, or D1332K substitutions to create six derivative variants. Next, we added the L1111R and A1322R substitutions to the original VRQR variant and the six derivative S55R, A61R, G366R, N394K, A1285K, or D1332K variants (for a total of 14 variants, including the base-model VRQR). With SpCas9-VRQR, we observed editing efficiencies consistent with previous results (Kleinstiver et al., Nature 523, 481-485 (2015); Kleinstiver et al., Nature 529, 490-495 (2016); Walton et al., Science 368, 290-296 (2020)) on sites with NGAN PAMs (where NGAG>NGAT~NGAA>NGAC; FIG. 13). We also observed targeting of the NGCG and NGTG sites, consistent with the previously reported ability of SpCas9-VRQR to target some sites with NGNG PAMs (Walton et al., Science 368, 290-296 (2020)). The remainder of the target sites were largely unedited by SpCas9-VRQR. Upon addition of either the single activity enhancing substitutions, or combinations of different triple substitutions, in some cases we observed an improvement in on-target editing at target sites encoding prototypical NGAN and NGNG PAMs (e.g., with variants VRQR+S55R and VRQR+A61R; see FIG. 13). However, on the NGAG-1 site that was initially highly targeted with SpCas9-VRQR, aside from the VRQR+S55R variant that improved editing, we observed either minimal change or a decrease in on-target editing for all remaining variants. This result potentially indicates that there is a limit to degree to which the editing efficiency of a Cas9 variant can be improved, before the combinations of substitutions exert a detrimental effect on editing. Based on this limited dataset, this observation appears to be target specific. With SpCas9-VRQR and the derivative variants on target sites with non-canonical PAMs (that were originally non-targetable or exhibited lower activities), we observed an almost uniform improvement in on-target editing by the inclusion of the single substitutions or the various combinations of substitutions.

Figure 14:
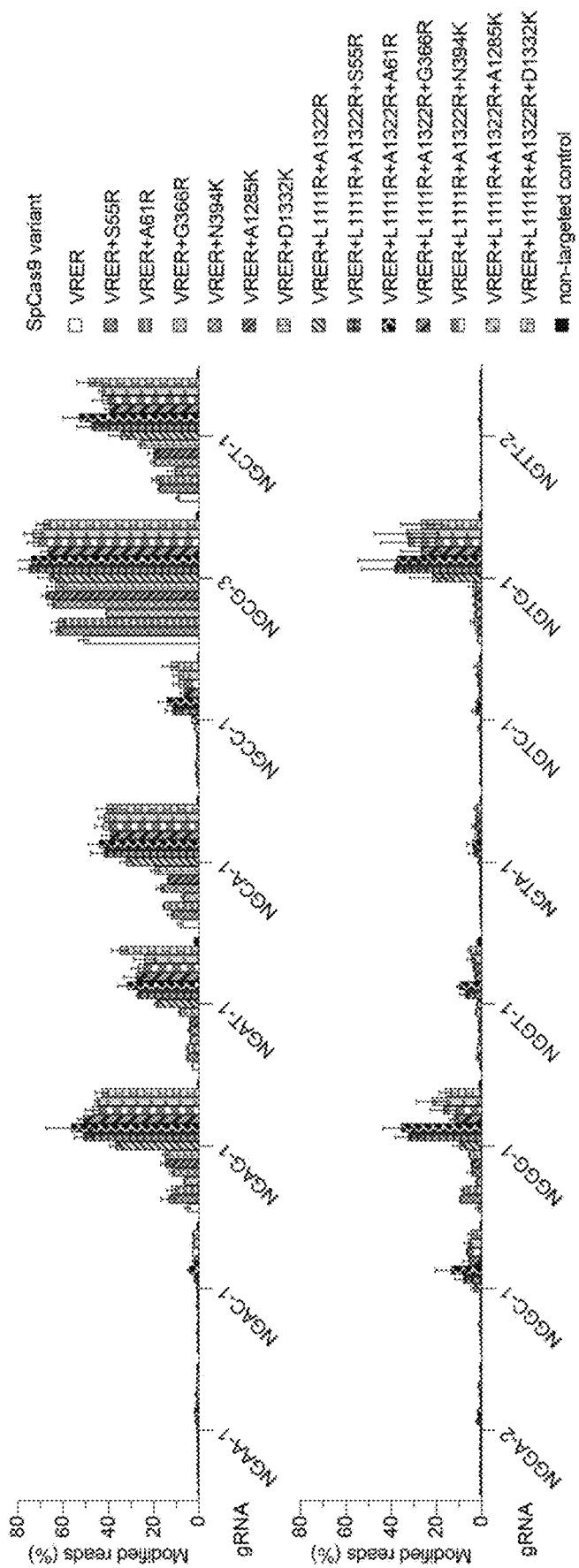
FIG. 14. Activities of SpCas9-VRER and variants bearing additional substitutions. Modification of endogenous sites in HEK 293T cells bearing NGNN PAMs by SpCas9-VRER (bearing D1135V/G1218R/R1335E/T1337R substitutions) and derivative variants encoding substitutions that putatively improve on-target editing. Percent modified reads assessed by targeted sequencing; mean and s.e.m. shown for n=2.

For SpCas9-VRER, we separately added the S55R, A61R, G366R, N394K, A1285K, or D1332K substitutions to create six derivative variants; we also added the L1111R and A1322R substitutions to the original VRER variant and the six derivative S55R, A61R, G366R, N394K, A1285K, or D1332K variants (for a total of 14 variants, including the base-model VRER). With SpCas9-VRER, we observed editing exclusively at the target site bearing an NGCG PAM (FIG. 14), consistent with previous characterization of the PAM requirement for this variant (Kleinstiver et al., Nature 523, 481-485 (2015)). The remainder of the target sites were largely unedited by SpCas9-VRER. Interestingly, upon addition of either the single activity enhancing substitutions, or combinations of two or three substitutions, not only did we observe a near-uniform improvement in editing at the on-target site with an NGCG PAM (for all variants except VRER+G366R), but for many variants we also now observed robust editing at sites with NGAG, NGAT, NGCA, NGCT, NGGG, and/or NGTG PAMs (FIG. 14). These results indicate that not only is it possible to improve the on-target editing of SpCas9-VRER at a target encoding a prototypical NGCG PAM, but that certain combinations of these activity-enhancing substitutions will also improve editing on target sites with PAMs previously inaccessible to the base-model VRER variant.

For SpCas9-MQKSER, we separately added the S55R, A61R, G366R, N394K, A1285K, D1332K, L1111R, or A1322R substitutions to create eight derivative variants; we also added the pair of L1111R and A1322R substitutions to the original MQKSER variant and the six derivative S55R, A61R, G366R, N394K, A1285K, or D1332K variants (for a total of 16 variants, including the base-model MQKSER). With MQKSER, we observed editing at target sites bearing an NGCN, NGNG, NGAT, and NGGT PAMs (FIG. 15). Similar to our observations with SpCas9-VRQR, for some sites that were already highly edited with the base-model MQKSER variant, few activity-enhancing substitutions could improve on-target editing (e.g. on the sites with NGAG or NGCG PAMs; FIG. 15); however, some variants were able to robustly improve activity on certain sites (e.g. the site with the NGCC PAM). On sites that were previously uneditable with MQKSER, with many of the activity-enhanced variants we could now observe efficient levels of editing (e.g. NGTA, NGTC, etc.). These results indicate that depending on the target site, with MQKSER certain combinations of activity-enhancing substitutions improved editing at target sites with previously accessible or inaccessible PAMs.

For SpCas9-VRAVQL, we separately added the S55R, G366R, N394K, A1285K, D1332K, L1111R, or A1322R substitutions to create seven derivative variants; we also added the pair of L1111R and A1322R substitutions to the original VRAVQL variant and the six S55R, A61R, G366R, N394K, A1285K, or D1332K variants (for a total of 15 variants, including the base-model VRAVQL). With VRAVQL, we observed the most efficient editing at the four target sites encoding NGTN PAMs, but also observed detectable editing at several other target sites (e.g. those with NGAT, NGCA, etc.; FIG. 16). Similar to our observations with SpCas9-VRER, nearly all combinations of activity enhancing substitutions uniformly improved on-target editing at target sites with both canonical and non-canonical PAMs; FIG. 16). Furthermore, for sites that were previously uneditable with VRAVQL, with many of the activity-enhanced variants we now observed efficient levels of editing (e.g. NGCC, etc.) depending on the combinations of substitutions. These results indicate that depending on the target site, with VRAVQL certain combinations of activity-enhancing substitutions improved editing at target sites with previously accessible or inaccessible PAMs.

Together, these results support a general framework to improve the on-target editing of various SpCas9 variants. For variants that already have robust editing at sites with certain PAMs (e.g., VRQR on NGAG PAMs, or MQKSER on NGCG PAMs), in some cases editing was negatively impacted by the inclusion of activity enhancing substitutions. However, for variants that are initially less active on their canonical target sties (e.g. VRER on NGCG PAMs, or VRAVQL on NGTN PAMs), nearly all derivative variants bearing activity-enhancing substitutions improved on-target editing. The present data suggests that certain combinations of substitutions improve on-target editing.

REFERENCES

1. Sander, J. D. & Joung, K. J. CRISPR-Cas systems for editing, regulating and targeting genomes. Nat Biotechnol 32, 347-55 (2014).
2. Hsu, P. D., Lander, E. S. & Zhang, F. Development and applications of CRISPR-Cas9 for genome engineering. Cell 157, 1262-78 (2014).
3. Komor, A. C., Badran, A. H. & Liu, D. R. CRISPR-Based Technologies for the Manipulation of Eukaryotic Genomes. Cell 168, 20-36 (2017).
4. Rees, H. A. & Liu, D. R. Base editing: precision chemistry on the genome and transcriptome of living cells. Nat Rev Genet 19, 770-788 (2018).
5. Doench, J. G. et al. Optimized sgRNA design to maximize activity and minimize off-target effects of CRISPR-Cas9. Nat Biotechnol 34, 184-91 (2016).
6. Kim, H. et al. Deep learning improves prediction of CRISPR-Cpf1 guide RNA activity. Nat Biotechnol 36, 239-241 (2018).
7. Kim, H. et al. SpCas9 activity prediction by DeepSpCas9, a deep learning-based model with high generalization performance. Sci Adv 5, eaax9249 (2019).
8. Kleinstiver, B. P. et al. Engineered CRISPR-Cas9 nucleases with altered PAM specificities. Nature 523, 481-5 (2015).
9. Kleinstiver, B. P. et al. High-fidelity CRISPR-Cas9 nucleases with no detectable genome-wide off-target effects. Nature 529, 490-5 (2016).
10. Hirano, S., Nishimasu, H., Ishitani, R. & Nureki, O. Structural Basis for the Altered PAM Specificities of Engineered CRISPR-Cas9. Mol Cell 61, 886-94 (2016).
11. Anders, C., Bargsten, K. & Jinek, M. Structural Plasticity of PAM Recognition by Engineered Variants of the RNA-Guided Endonuclease Cas9. Mol Cell 61, 895-902 (2016).
12. Spencer, J. & Zhang, X. Deep mutational scanning of S. pyogenes Cas9 reveals important functional domains. Sci Rep-uk 7, 16836 (2017).
13. Nishimasu, H. et al. Engineered CRISPR-Cas9 nuclease with expanded targeting space. Science 361, 1259-1262 (2018).
14. Kleinstiver, B. P. et al. Engineered CRISPR-Cas12a variants with increased activities and improved targeting ranges for gene, epigenetic and base editing. Nat Biotechnol 37, 276-282 (2019).
15. Anders, C., Niewoehner, O., Duerst, A. & Jinek, M. Structural basis of PAM-dependent target DNA recognition by the Cas9 endonuclease. Nature 513, 569-73 (2014).
16. Komor, A. C., Kim, Y. B., Packer, M. S., Zuris, J. A. & Liu, D. R. Programmable editing of a target base in genomic DNA without double-stranded DNA cleavage. Nature 533, 420-4 (2016).
17. Koblan, L. W. et al. Improving cytidine and adenine base editors by expression optimization and ancestral reconstruction. Nat Biotechnol 36, 843-846 (2018).

18. Gaudelli, N. M. et al. Programmable base editing of A•T to G•C in genomic DNA without DNA cleavage. Nature 551, 464-471 (2017).
19. Rohland, N. & Reich, D. Cost-effective, high-throughput DNA sequencing libraries for multiplexed target capture. Genome Res 22, 939-46 (2012).
20. Clement, K. et al. CRISPResso2 provides accurate and rapid genome editing sequence analysis. Nat Biotechnol 37, 224-226 (2019).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated *Streptococcus pyogenes* Cas9 (SpCas9) protein, comprising an amino acid sequence that has at least 95% sequence identity to the amino acid sequence of SEQ ID NO: 1, comprising one of the following sets of mutations: A61R/N1317R, G1104K/N1317R, A61R/G1104K, S55R/G1104K, S55R/A61R, S55R/N1317R, G1104K/T1314R, A61R/T1314R, T1314R/N1317R, S55R/T1314R, A61R/G1104R, G1104R/N1317R, S55R/G1104R, G1104R/T1314R, G366R/G1104K, S55R/G366R, A61R/G366R, G366R/N1317R, G366R/T1314R, G366R/G1104R, G1104K/A1285R, A61R/A1285R, A1285R/N1317R, S55R/A1285R, A1285R/T1314R, G1104R/A1285R, G366R/A1285R, G1104K/A1285K, A61R/A1285K, A1285K/N1317R, S55R/A1285K, A1285K/T1314R, G1104R/A1285K, G366R/A1285K, G1104K/D1332R, A61R/D1332R, D1332R/N1317R, S55R/D1332R, G1104R/D1332R, G366R/D1332R, A1285K/D1332R, A1285R/D1332R, A61R/G1104K/N1317R, A61R/L1111R, A61R/A1322R, A61R/L1111R/A1322R, G1104K/L1111R, G1104K/A1322R, G1104K/L1111R/A1322R, N1317R/L1111R, N1317R/A1322R, N1317R/L1111R/A1322R, A61R/N1317R/L1111R, A61R/N1317R/A1322R, A61R/N1317R/L1111R/A1322R, G1104K/N1317R/L1111R, G1104K/N1317R/A1322R, G1104K/N1317R/L1111R/A1322R, A61R/G1104K/L1111R, A61R/G1104K/A1322R, A61R/G1104K/L1111R/A1322R, S55R/L1111R, S55R/A1322R, S55R/L1111R/A1322R, G366R/L1111R, G366R/A1322R, G366R/L1111R/A1322R, A1285K/L1111R, A1285K/A1322R, or A1285K/L1111R/A1322R.

2. The isolated SpCas9 protein of claim 1, further comprising:
   (i) a mutation at a position selected from the group consisting of D10, E762, D839, H983, or D986; and/or
   (ii) a mutation at position H840 or N863.

3. The isolated SpCas9 protein of claim 2, wherein the mutations are:
   (i) D10A or D10N, and
   (ii) H840A, H840N, or H840Y.

4. The isolated SpCas9 protein of claim 1, further comprising one or more mutations that increase specificity selected from the group consisting of mutations at N497, R661, N692, M694, Q695, H698, K810, K848, Q926, K1003, R0160, R691, M495, Y515, K526, and/or R661.

5. The isolated SpCas9 protein of claim 4, further comprising mutations at R691A, M495V, Y515N, K526E, R661Q, R661L, R661S, Y450A/Q695A, L169A/Q695A, Q695A/Q926A, Q695A/D1135E, Q926A/D1135E, Y450A/D1135E, L169A/Y450A/Q695A, L169A/Q695A/Q926A, Y450A/Q695A/Q926A, R661A/Q695A/Q926A, N497A/Q695A/Q926A, Y450A/Q695A/D1135E, Y450A/Q926A/D1135E, Q695A/Q926A/D1135E, L169A/Y450A/Q695A/Q926A, L169A/R661A/Q695A/Q926A, Y450A/R661A/Q695A/Q926A, N497A/Q695A/Q926A/D1135E, R661A/Q695A/Q926A/D1135E, and Y450A/Q695A/Q926A/D1135E; N692A/M694A/Q695A/H698A, N692A/M694A/Q695A/H698A/Q926A; N692A/M694A/Q695A/Q926A; N692A/M694A/H698A/Q926A; N692A/Q695A/H698A/Q926A; M694A/Q695A/H698A/Q926A; N692A/Q695A/H698A; N692A/M694A/Q695A; N692A/H698A/Q926A; N692A/M694A/Q926A; N692A/M694A/H698A; M694A/Q695A/H698A; M694A/Q695A/Q926A; Q695A/H698A/Q926A; G582A/V583A/E584A/D585A/N588A/Q926A; G582A/V583A/E584A/D585A/N588A; T657A/G658A/W659A/R661A/Q926A; T657A/G658A/W659A/R661A; F491A/M495A/T496A/N497A/Q926A; F491A/M495A/T496A/N497A; K918A/V922A/R925A/Q926A; or 918A/V922A/R925A; K855A; K810A/K1003A/R1060A; K848A/K1003A/R1060A; M495V/Y515N/K526E/R661Q; M495V/Y515N/K526E/R661L; or M495V/Y515N/K526E/R661S.

6. A fusion protein comprising the isolated SpCas9 protein of claim 1, fused to a heterologous functional domain.

7. The fusion protein of claim 6, wherein the heterologous functional domain is a transcriptional activation domain.

8. The fusion protein of claim 7, wherein the transcriptional activation domain is from VP16, VP64, rTA, NF-κB p65, or the composite VPR (VP64-p65-rTA).

9. The fusion protein of claim 6, wherein the heterologous functional domain is a transcriptional silencer or transcriptional repression domain.

10. The fusion protein of claim 9, wherein the transcriptional repression domain is a Krueppel-associated box (KRAB) domain, ERF repressor domain (ERD), or mSin3A interaction domain (SID).

11. The fusion protein of claim 9, wherein the transcriptional silencer is Heterochromatin Protein 1 (HP1).

12. The fusion protein of claim 6, wherein the heterologous functional domain is an enzyme that modifies the methylation state of DNA.

13. The fusion protein of claim 12, wherein the enzyme that modifies the methylation state of DNA is a DNA methyltransferase (DNMT) or a TET protein.

14. The fusion protein of claim 13, wherein the TET protein is TET1.

15. The fusion protein of claim 6, wherein the heterologous functional domain is an enzyme that modifies a histone subunit.

16. The fusion protein of claim 15, wherein the enzyme that modifies a histone subunit is a histone acetyltransferase (HAT), histone deacetylase (HDAC), histone methyltransferase (HMT), or histone demethylase.

17. The fusion protein of claim 6, wherein the heterologous functional domain is a base editor or a prime editor.

18. The fusion protein of claim 17, wherein the base editor is a DNA or RNA deaminase; or wherein the prime editor comprises a reverse transcriptase (RT) domain.

19. The fusion protein of claim 18, wherein the base editor is a cytosine or adenine deaminase domain, or activation-induced cytidine deaminase.

20. The fusion protein of claim 6, wherein the heterologous functional domain is a biological tether.

21. The fusion protein of claim 20, wherein the biological tether is MS2, Csy4 or lambda N protein.

22. The fusion protein of claim 6, wherein the heterologous functional domain is FokI.

23. An isolated nucleic acid encoding the protein of claim 1.

24. A vector comprising the isolated nucleic acid of claim 23.

25. The vector of claim 24, wherein the isolated nucleic acid of claim 23 is operably linked to one or more regulatory domains for expressing an isolated *Streptococcus pyogenes* Cas9 (SpCas9) protein.

26. An isolated host cell, comprising the nucleic acid of claim 23.

27. The isolated host cell of claim 26, wherein the host cell is a mammalian cell.

28. A method of altering the genome of a cell, the method comprising expressing in the cell, or contacting the cell with, the isolated SpCas9 protein of claim 1, and a guide RNA having a region complementary to a selected portion of the genome of the cell.

29. The method of claim 28, wherein the isolated SpCas9 protein comprises one or more of a nuclear localization sequence, cell penetrating peptide sequence, and/or affinity tag.

30. The method of claim 29, wherein the cell is a stem cell.

31. The method of claim 30, wherein the cell is an embryonic stem cell, mesenchymal stem cell, or induced pluripotent stem cell; is in a living non-human animal; or is in non-human embryo.

32. A method of altering a double stranded DNA (dsDNA) molecule, the method comprising contacting the dsDNA molecule with the isolated SpCas9 protein of claim 1, and a guide RNA having a region complementary to a selected portion of the dsDNA molecule.

33. The method of claim 32, wherein the dsDNA molecule is in vitro.

34. The method of claim 32, wherein the isolated SpCas9 protein and RNA are in a ribonucleoprotein complex.

35. The isolated SpCas9 protein of claim 1, wherein the SpCas9 further comprises one of the following sets of mutations:
(1) D1135L/S1136W/G1218K/E1219Q/R1335Q/T1337R,
(2) D1135V/R1335Q/T1337R
(3) D1135V/G1218R/R1335E/T1337R
(4) D1135M/S1136Q/G1218K/E1219S/R1335E/T1337R
(5) D1135V/G1218R/R1335Q/T1337R, or
(6) D1135V/S1136R/G1218A/E1219V/R1335Q/T1337L.

* * * * *

SEQUENCE LISTING

```
<160> NUMBER OF SEQ ID NOS: 19

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300
```

```
Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720
```

```
His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
                850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125
```

-continued

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 4
<212> TYPE: PRT
<213> ORGANISM: Artificial Sequence
<220> FEATURE:
<223> OTHER INFORMATION: linker

<400> SEQUENCE: 2

Gly Gly Gly Ser
1

<210> SEQ ID NO 3
<211> LENGTH: 5
<212> TYPE: PRT
<213> ORGANISM: Artificial Sequence
<220> FEATURE:
<223> OTHER INFORMATION: linker

<400> SEQUENCE: 3

Gly Gly Gly Gly Ser
1               5

<210> SEQ ID NO 4
<211> LENGTH: 20
<212> TYPE: DNA
<213> ORGANISM: Artificial Sequence

```
<220> FEATURE:
<223> OTHER INFORMATION: target site NGAA-1 in EMX1

<400> SEQUENCE: 4
gctgagctga gagcctgatg                                               20

<210> SEQ ID NO 5
<211> LENGTH: 20
<212> TYPE: DNA
<213> ORGANISM: Artificial Sequence
<220> FEATURE:
<223> OTHER INFORMATION: target site NGAC-1 in DNMT1

<400> SEQUENCE: 5
ggccagccca gcagccaacc                                               20

<210> SEQ ID NO 6
<211> LENGTH: 20
<212> TYPE: DNA
<213> ORGANISM: Artificial Sequence
<220> FEATURE:
<223> OTHER INFORMATION: target site NGAG-1 in VEGFA

<400> SEQUENCE: 6
gcgagcagcg tcttcgagag                                               20

<210> SEQ ID NO 7
<211> LENGTH: 20
<212> TYPE: DNA
<213> ORGANISM: Artificial Sequence
<220> FEATURE:
<223> OTHER INFORMATION: target site NGAT-1 in RUNX1

<400> SEQUENCE: 7
gcagagggga gaagaaagag                                               20

<210> SEQ ID NO 8
<211> LENGTH: 20
<212> TYPE: DNA
<213> ORGANISM: Artificial Sequence
<220> FEATURE:
<223> OTHER INFORMATION: target site NGCA-1 in FANCF

<400> SEQUENCE: 8
gcggctgcac aaccagtgga                                               20

<210> SEQ ID NO 9
<211> LENGTH: 20
<212> TYPE: DNA
<213> ORGANISM: Artificial Sequence
<220> FEATURE:
<223> OTHER INFORMATION: target site NGCC-1 in RUNX1

<400> SEQUENCE: 9
gactcaaata tgctgtctga                                               20

<210> SEQ ID NO 10
<211> LENGTH: 20
<212> TYPE: DNA
<213> ORGANISM: Artificial Sequence
<220> FEATURE:
<223> OTHER INFORMATION: target site NGCG-3 in FANCF

<400> SEQUENCE: 10
gcagaaggga ttccatgagg                                               20
```

```
<210> SEQ ID NO 11
<211> LENGTH: 20
<212> TYPE: DNA
<213> ORGANISM: Artificial Sequence
<220> FEATURE:
<223> OTHER INFORMATION: target site NGCT-1 in FANCF

<400> SEQUENCE: 11
gctcggaaaa gcgatccagg                                              20

<210> SEQ ID NO 12
<211> LENGTH: 20
<212> TYPE: DNA
<213> ORGANISM: Artificial Sequence
<220> FEATURE:
<223> OTHER INFORMATION: target site NGGA-2 in DNMT1

<400> SEQUENCE: 12
gagtgctaag ggaacgttca                                              20

<210> SEQ ID NO 13
<211> LENGTH: 20
<212> TYPE: DNA
<213> ORGANISM: Artificial Sequence
<220> FEATURE:
<223> OTHER INFORMATION: target site NGGC-1 in EMX1

<400> SEQUENCE: 13
gagtccgagc agaagaagaa                                              20

<210> SEQ ID NO 14
<211> LENGTH: 20
<212> TYPE: DNA
<213> ORGANISM: Artificial Sequence
<220> FEATURE:
<223> OTHER INFORMATION: target site NGGG-1 in VEGFA

<400> SEQUENCE: 14
ggtgagtgag tgtgtgcgtg                                              20

<210> SEQ ID NO 15
<211> LENGTH: 20
<212> TYPE: DNA
<213> ORGANISM: Artificial Sequence
<220> FEATURE:
<223> OTHER INFORMATION: target site NGGT-1 in DNMT1

<400> SEQUENCE: 15
gtcactctgg ggaacacgcc                                              20

<210> SEQ ID NO 16
<211> LENGTH: 20
<212> TYPE: DNA
<213> ORGANISM: Artificial Sequence
<220> FEATURE:
<223> OTHER INFORMATION: target site NGTA-1 in EMX1

<400> SEQUENCE: 16
gttccagaac cggaggacaa                                              20

<210> SEQ ID NO 17
<211> LENGTH: 20
<212> TYPE: DNA
<213> ORGANISM: Artificial Sequence
<220> FEATURE:
<223> OTHER INFORMATION: target site NGTC-1 in FANCF
```

```
<400> SEQUENCE: 17
ggcccggcgc acggtggcgg                                                20

<210> SEQ ID NO 18
<211> LENGTH: 20
<212> TYPE: DNA
<213> ORGANISM: Artificial Sequence
<220> FEATURE:
<223> OTHER INFORMATION: target site NGTG-1 in RUNX1

<400> SEQUENCE: 18
gtcccccgcc ttcagaagag                                                20

<210> SEQ ID NO 19
<211> LENGTH: 20
<212> TYPE: DNA
<213> ORGANISM: Artificial Sequence
<220> FEATURE:
<223> OTHER INFORMATION: target site NGTT-2 in RUNX1

<400> SEQUENCE: 19
gacttgtaat catatgcctc                                                20
```